(12) United States Patent
Varone et al.

(10) Patent No.: US 11,788,044 B2
(45) Date of Patent: Oct. 17, 2023

(54) RHEOLOGICALLY BIOMIMETIC FLUID SURROGATE

(71) Applicant: EMULATE, INC., Boston, MA (US)

(72) Inventors: Antonio Varone, West Roxbury, MA (US); Magdalena Kasendra, Boston, MA (US); Carolina Lucchesi, Westwood, MA (US); S. Jordan Kerns, Reading, MA (US); Riccardo Barrile, Boston, MA (US); Sonalee Barthakur, Boston, MA (US)

(73) Assignee: EMULATE, Inc., Boston, MA (US)

( * ) Notice: Subject to any disclaimer, the term of this patent is extended or adjusted under 35 U.S.C. 154(b) by 671 days.

(21) Appl. No.: 16/820,530

(22) Filed: Mar. 16, 2020

(65) Prior Publication Data

US 2020/0332240 A1 Oct. 22, 2020

Related U.S. Application Data

(63) Continuation of application No. PCT/US2018/052301, filed on Sep. 21, 2018.
(Continued)

(51) Int. Cl.
*C12M 3/06* (2006.01)
*B01L 3/00* (2006.01)
(Continued)

(52) U.S. Cl.
CPC ....... *C12M 23/16* (2013.01); *B01L 3/502715* (2013.01); *B01L 3/502761* (2013.01);
(Continued)

(58) Field of Classification Search
CPC ......... B01L 3/502715; B01L 3/502761; B01L 2200/16; B01L 2300/123; B01L 2300/16;
(Continued)

(56) References Cited

U.S. PATENT DOCUMENTS

| 8,647,861 B2 | 2/2014 | Ingber et al. ............. 435/289.1 |
| 2008/0167226 A1 | 7/2008 | Flink et al. .................. 514/11.7 |

(Continued)

FOREIGN PATENT DOCUMENTS

| WO | WO2010/009307 A2 | 1/2010 |
| WO | WO2012/118799 A2 | 9/2012 |

(Continued)

OTHER PUBLICATIONS

Avishay, et al., "The Rheologic Properties of Erythrocytes: A Study Using an Automated Rheoscope." *Rheologica Acta*, 46(5):621-627 (2007).
(Continued)

*Primary Examiner* — Dean Kwak
(74) *Attorney, Agent, or Firm* — Medlen & Carroll, LLP

(57) ABSTRACT

The present invention contemplates compositions, devices and methods of simulating biological fluids in a fluidic device, including but not limited to a microfluidic chip. In one embodiment, fluid comprising a colloid under flow in a microfluidic chip has a fluid density or viscosity similar to a bodily fluid, e.g. blood, lymph, lung fluid, or the like. In one embodiment, a fluid is provided as a Theologically biomimetic blood surrogate or substitute for simulating physiological shear stress and cell dynamics in fluidic device, including but not limited to immune cells.

11 Claims, 51 Drawing Sheets
(30 of 51 Drawing Sheet(s) Filed in Color)

Related U.S. Application Data

(60) Provisional application No. 62/561,513, filed on Sep. 21, 2017.

(51) Int. Cl.
    *C12M 1/12*    (2006.01)
    *C12N 5/071*   (2010.01)
    *G01N 33/50*   (2006.01)
    *C12M 1/00*    (2006.01)

(52) U.S. Cl.
    CPC ............ *C12M 23/26* (2013.01); *C12M 25/02* (2013.01); *C12N 5/069* (2013.01); *G01N 33/5047* (2013.01); *G01N 33/5064* (2013.01); *B01L 2200/16* (2013.01); *B01L 2300/123* (2013.01); *B01L 2300/16* (2013.01); *C12N 2500/00* (2013.01); *C12N 2501/052* (2013.01); *C12N 2501/2301* (2013.01); *C12N 2501/2306* (2013.01); *C12N 2501/25* (2013.01)

(58) Field of Classification Search
    CPC ............ B01L 2200/0647; C12M 23/16; C12M 23/26; C12M 25/02; C12M 29/04; C12N 5/069; C12N 2500/00; C12N 2501/052; C12N 2501/2301; C12N 2501/2306; C12N 2501/25; G01N 33/5047; G01N 33/5064; G01N 2015/0065
    See application file for complete search history.

(56) References Cited

U.S. PATENT DOCUMENTS

| | | | |
|---|---|---|---|
| 2009/0263468 A1 | 10/2009 | McAnulty et al. | 424/443 |
| 2010/0240132 A1 | 9/2010 | Lanza et al. | 435/455 |
| 2011/0171689 A1 | 4/2011 | Warren et al. | 435/70.4 |
| 2011/0105359 A1* | 5/2011 | Czerwinski | A01N 1/0284 506/10 |
| 2011/0250585 A1* | 10/2011 | Ingber | C12N 5/061 977/773 |
| 2017/0055522 A1 | 3/2017 | Levner et al. | |
| 2017/0058248 A1 | 3/2017 | Hinojosa et al. | |

FOREIGN PATENT DOCUMENTS

| | | |
|---|---|---|
| WO | PCT/US2014/071570 | 9/2015 |
| WO | PCT/US2014/071611 | 9/2015 |
| WO | WO 2016/123474 | 8/2016 |
| WO | WO 2016/123474 A1 | 8/2016 |
| WO | PCT/US2016/022928 | 9/2016 |
| WO | PCT/US2016/025228 | 10/2016 |
| WO | PCT/US2016/026831 | 10/2016 |
| WO | PCT/US2016/033686 | 12/2016 |
| WO | PCT/US2016/064179 | 6/2017 |
| WO | PCT/US2016/064795 | 6/2017 |
| WO | PCT/US2016/064813 | 6/2017 |
| WO | PCT/US2016/064814 | 6/2017 |
| WO | WO 2017/096297 A1 | 6/2017 |
| WO | PCT/US2017/016079 | 8/2017 |
| WO | PCT/US2017/017980 | 8/2017 |
| WO | PCT/US2017/024988 | 10/2017 |
| WO | PCT/US17/49115 | 3/2018 |

OTHER PUBLICATIONS

Benam, et al., "Small Airway-on-a-Chip Enables Analysis of Human Lung Inflammation and Drug Responses in Vitro." *Nat Methods*, 13(2):151-157 (2016).

Benam, et al., "Small Airway-on-a-Chip Enables Analysis of Human Lung Inflammation and Drug Responses in Vitro." *Nat Methods*, 13(2):151-157 (online methods) (2016).

Benam, et al., "Small Airway-on-a-Chip Enables Analysis of Human Lung Inflammation and Drug Responses in Vitro." *Nat Methods*, 13(2):151-157 (supplementary) (2016).

BioNumber Details Page (Date Edited: Aug. 24, 2017 12:47 PM; http://bionumbers.hms.harvard.edu/bionumber.aspx?id=100507). 2017.

Cucullo, et al., "The Role of Shear Stress in Blood-Brain Barrier Endothelial Physiology." *BMC Neurosci*, 12:40 (2011).

DeStefano, et al., "Effect of Shear Stress on iPSC-Derived Human Brain Microvascular Endothelial Cells (Dhbmecs)." *Fluids Barriers CNS*, 14(1):20 (2017).

Filippi "Mechanism of Diapedesis: Importance of the Transcellular Route." *Adv Immunol*, 129:25-53 (2016).

Launiere, et al., "Rheologically Biomimetic Cell Suspensions for Decreased Cell Settling in Microfluidic Devices." *Biomed Microdevices*, 13(3):549-557 (2011).

Nourshargh, et al., "Breaching Multiple Barriers: Leukocyte Motility through Venular Walls and the Interstitium." *Nat Rev Mol Cell Biol*, 11(5):366-378 (2010).

Tsai "Platelet Activation and the Formation of the Platelet Plug: Deficiency of Adamts13 Causes Thrombotic Thrombocytopenic Purpura." *Arterioscler Thromb Vasc Biol*, 23(3):388-396 (2003).

Vasilyeva, et al., "Serum Cytokine Profiles in Children with Crohn's Disease." *Mediators Inflamm*, 2016:7420127 (2016).

Wong, et al., "Directed Differentiation of Human Pluripotent Stem Cells into Mature Airway Epithelia Expressing Functional CFTR Protein." *Nat Biotechnol*, 30(9):876-882 (2012).

www.shenc.de/B3-Raedler-res.htm, downloaded Sep. 11, 2018.

Zipursky, et al., "Leukocyte Density and Volume in Normal Subjects and in Patients with Acute Lymphoblastic Leukemia." *Blood*, 48(3):361-371 (1976).

Adrian, et al., "Deoxycholate Is an Important Releaser of Peptide YY and Enteroglucagon from the Human Colon." *Gut*, 34(9):1219-1224 (1993).

Chin, et al., "The Role of Mechanical Forces and Adenosine in the Regulation of Intestinal Enterochromaffin Cell Serotonin Secretion." *Am J Physiol Gastrointest Liver Physiol*, 302(3):G397-405 (2012).

Kim, et al., "Contributions of Microbiome and Mechanical Deformation to Intestinal Bacterial Overgrowth and Inflammation in a Human Gut-on-a-Chip." *Proc Natl Acad Sci U S A*, 113(1):E7-15 (2016).

Ootani, et al., "Sustained in Vitro Intestinal Epithelial Culture within a Wnt-Dependent Stem Cell Niche." *Nat Med*, 15(6):701-706 (2009).

* cited by examiner

Bottom spiral channel   Vacuum Chamber

Figures 10A-G
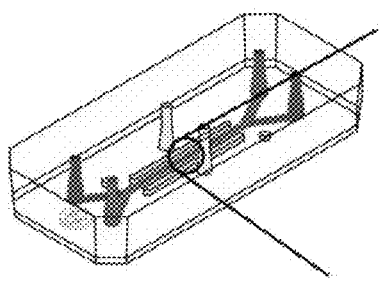
Figure 10A
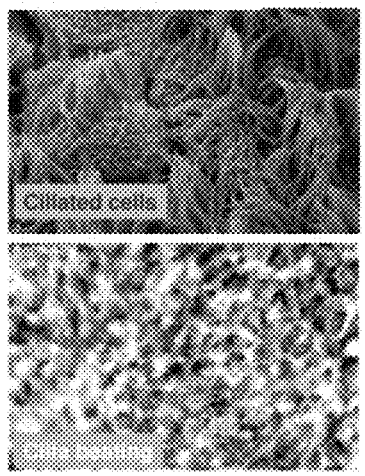
Figure 10B
Figure 10C
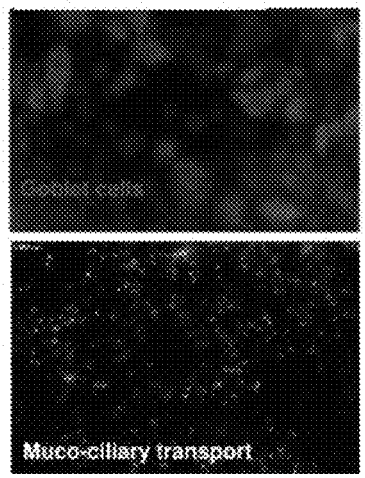
Figure 10D
Figure 10E
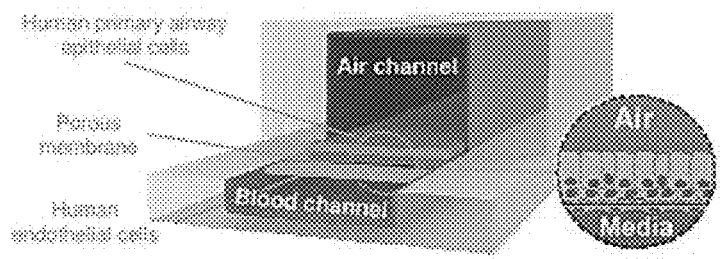
Figure 10F
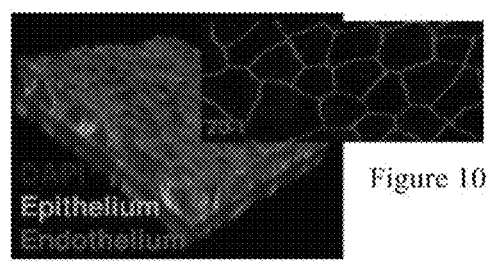
Figure 10G Figures 12A-D
Figure 12A
Figure 12B
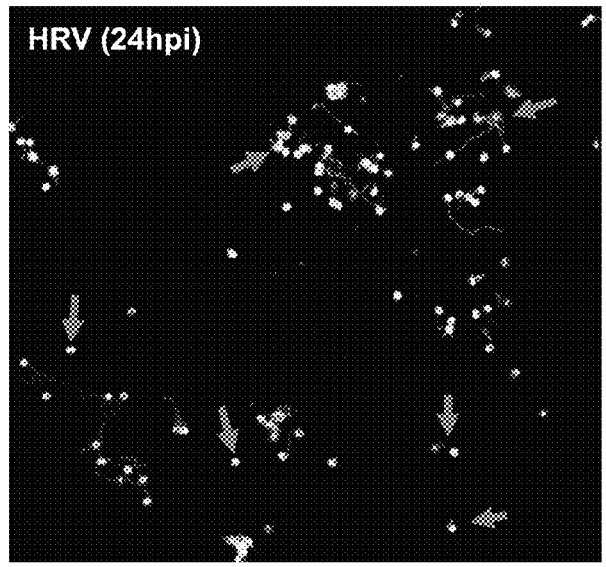
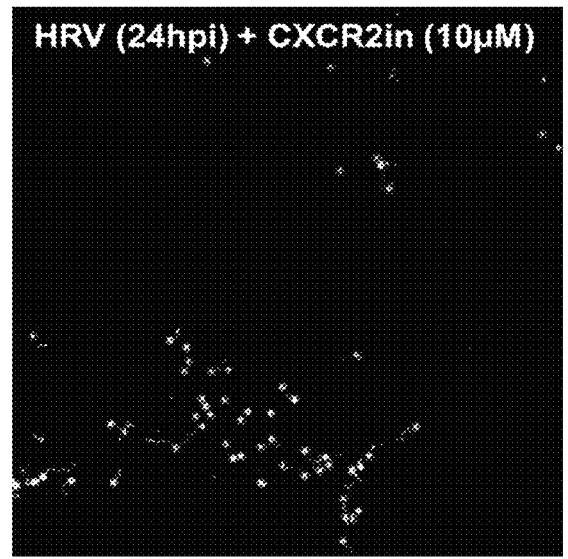
Figure 12C
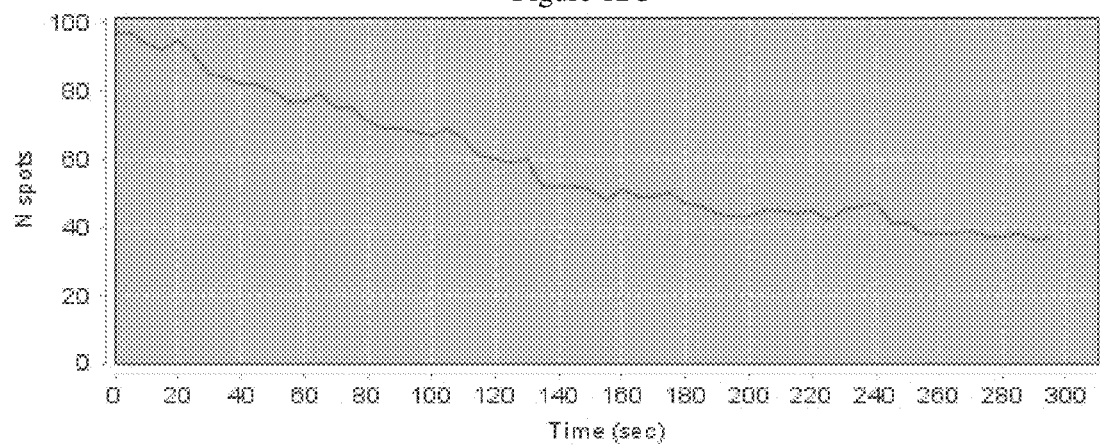

Figure 16 (Cont)
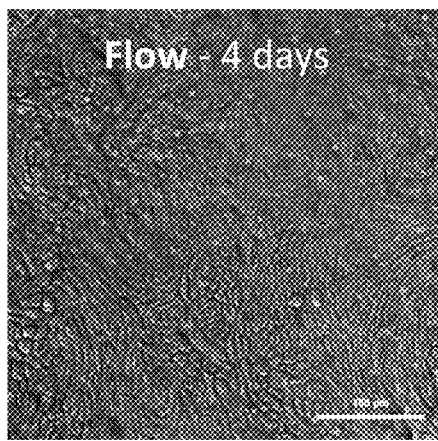
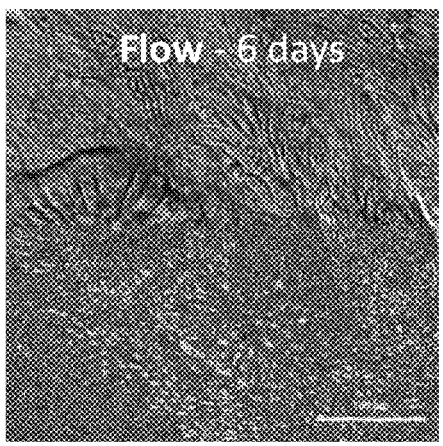
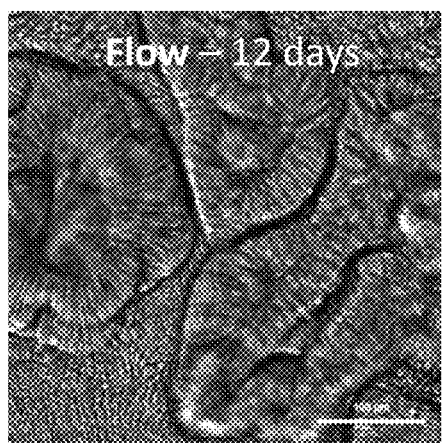
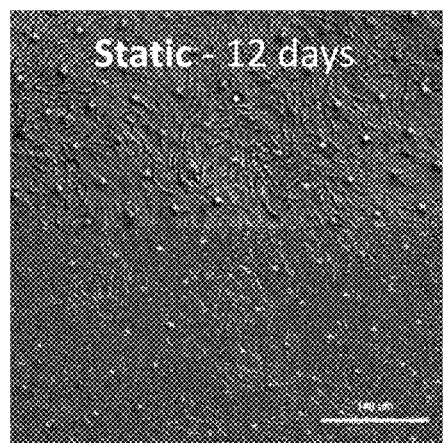

Figure 19A-H
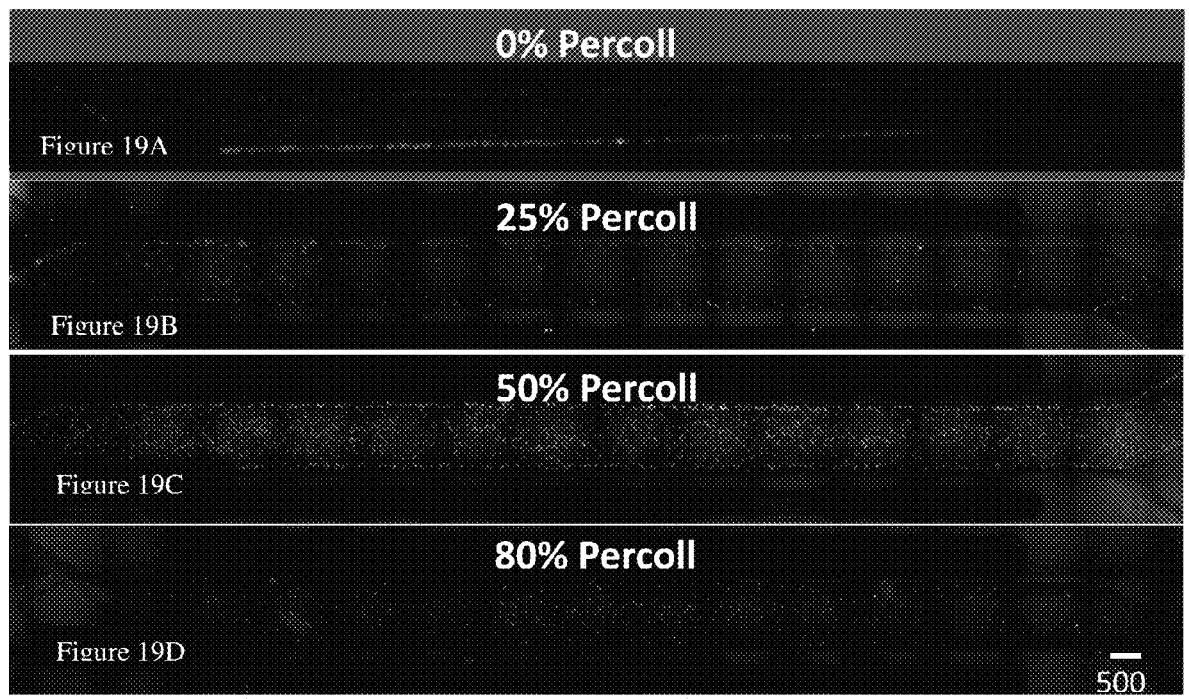
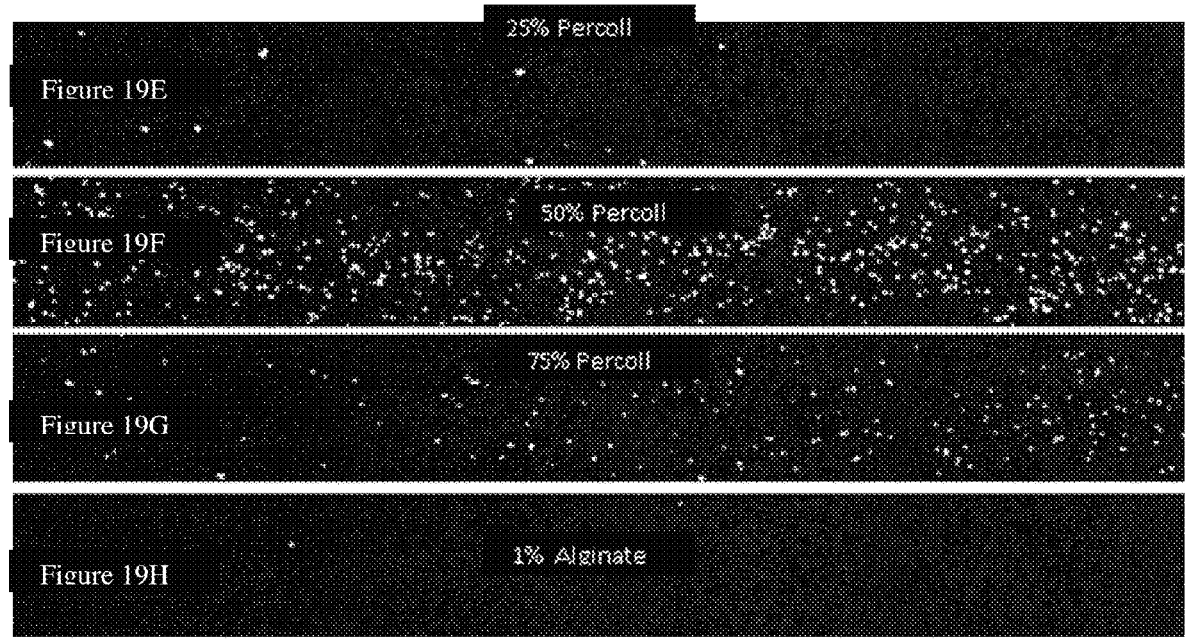

Figures 20A-E
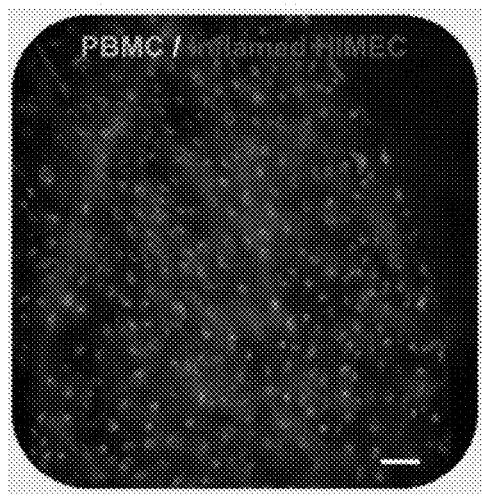
Figure 20A
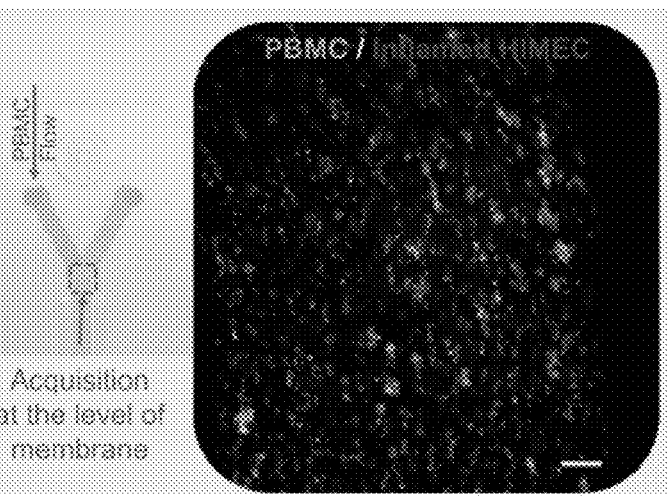
Figure 20C
Figure 20B
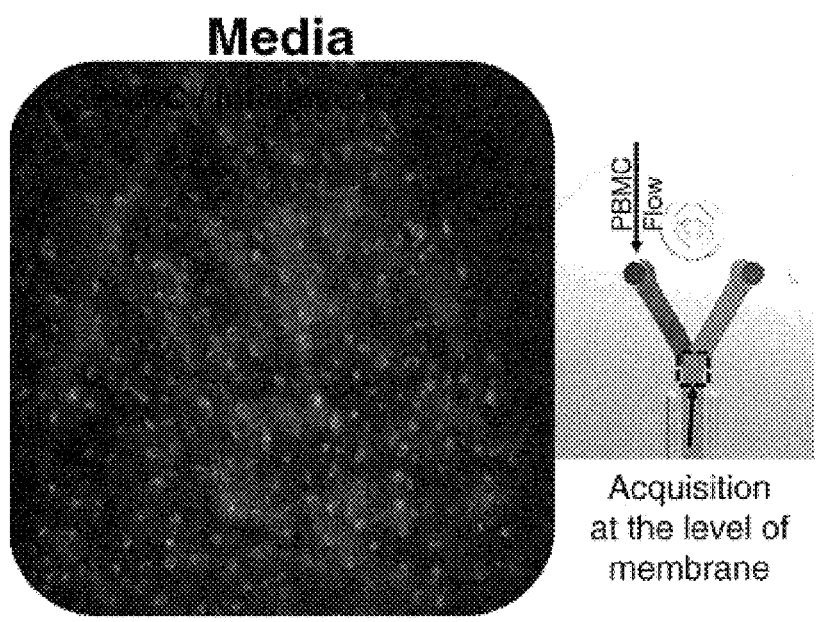
Figure 20D
Figure 20E

Figures 21A-B

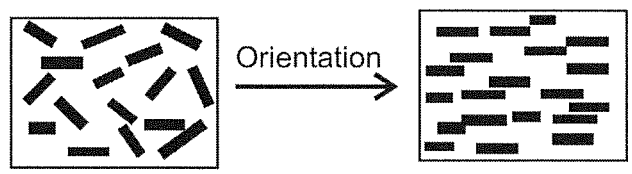
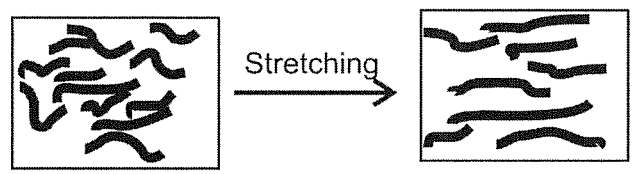
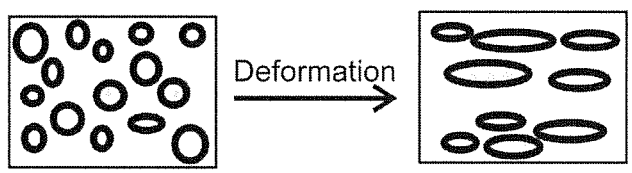
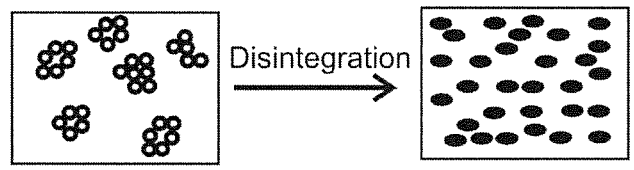
Figure 23A                Figure 23B

Figure 28A-D

Figure 31A-B
Figure 31A  Low shear stress
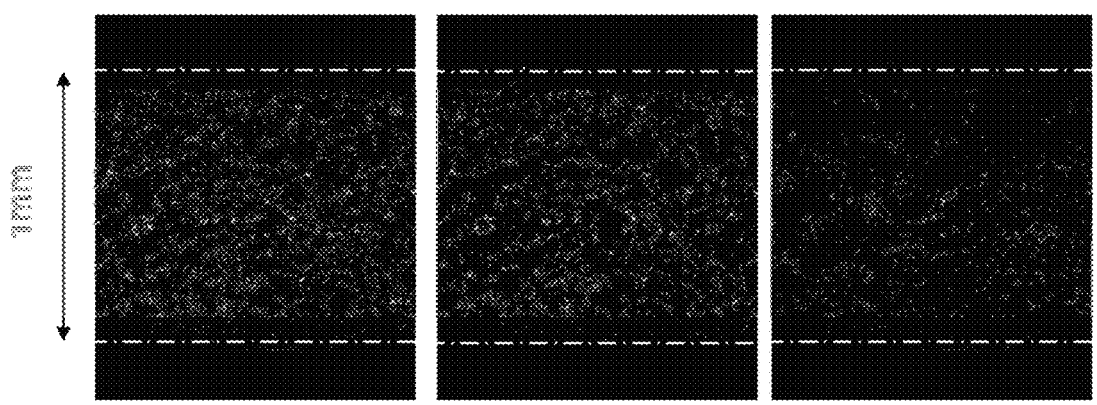
Figure 31B  Physiological relevant shear stress
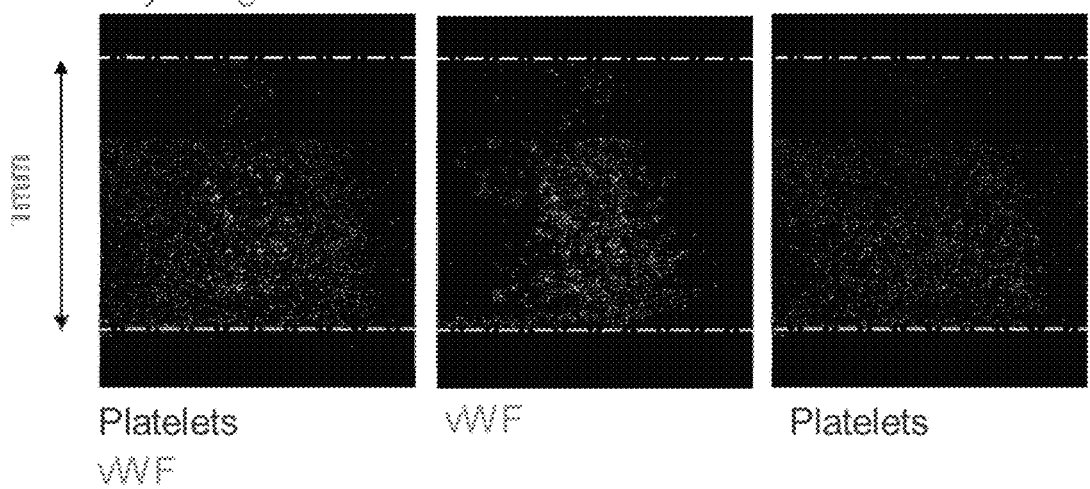
Platelets          vWF          Platelets
vWF

Figure 32A-C

Figure 33A-C
Figure 33A Whole channel (low magnification)  Figure 33B Magnified details
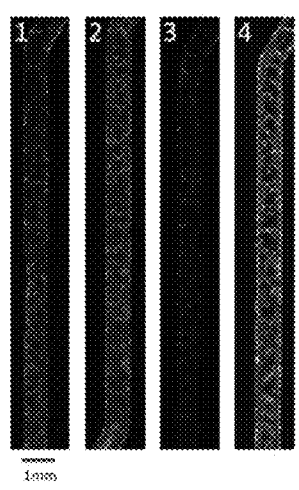
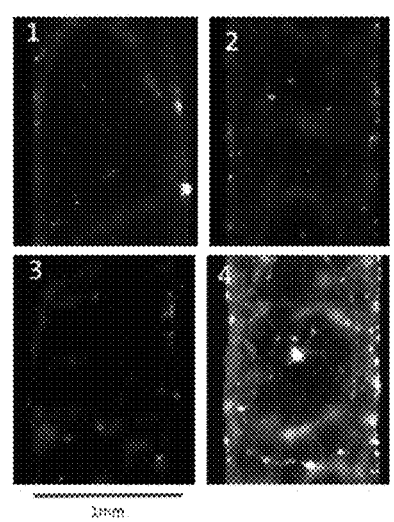
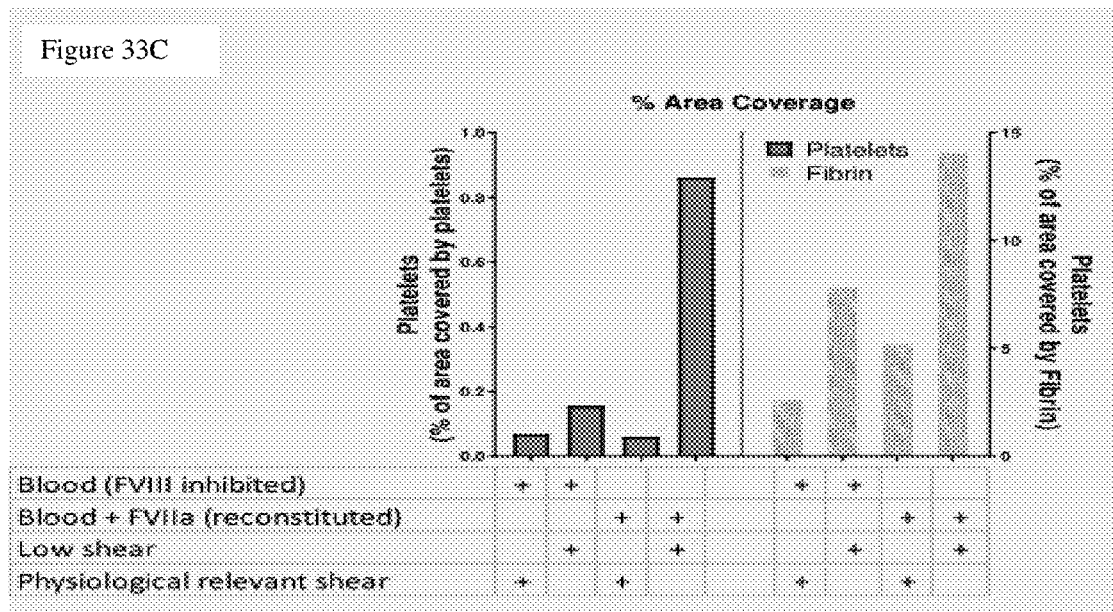

Figure 34
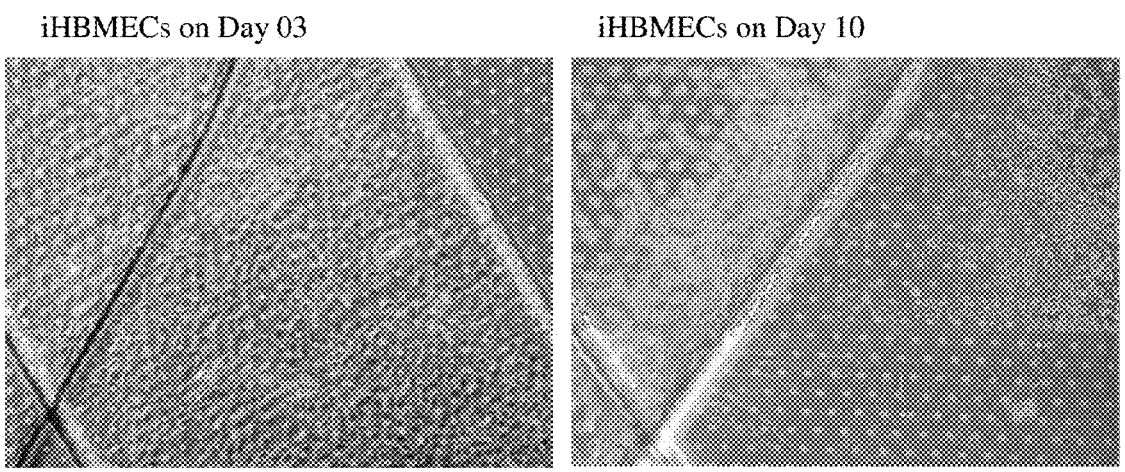
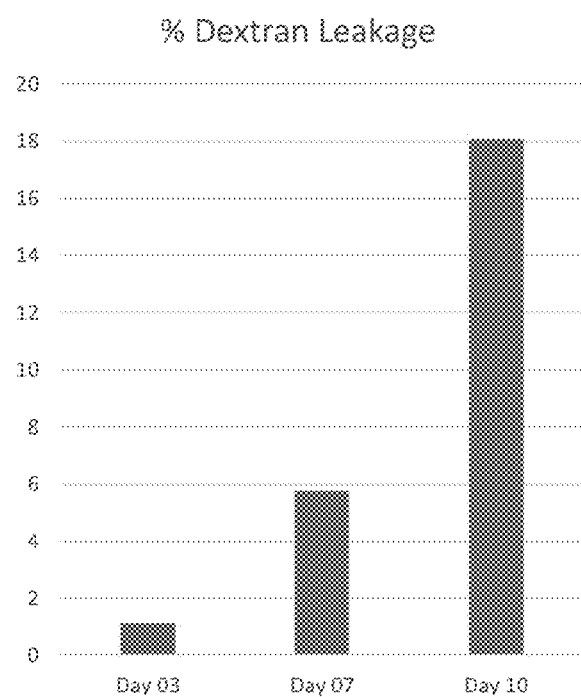

Figure 34 (cont)
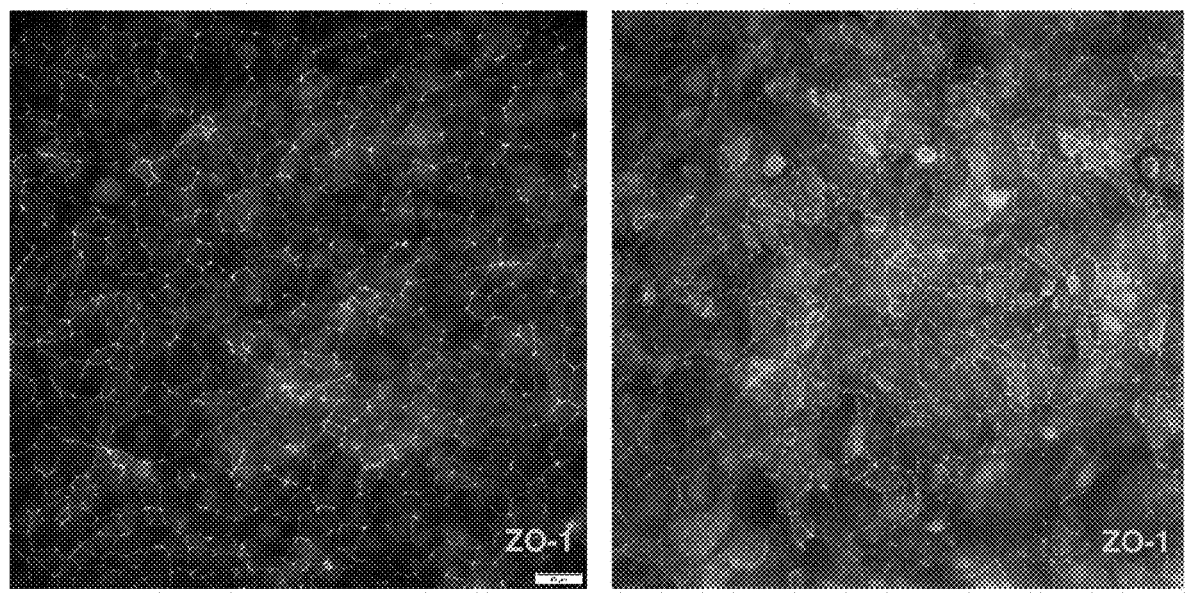
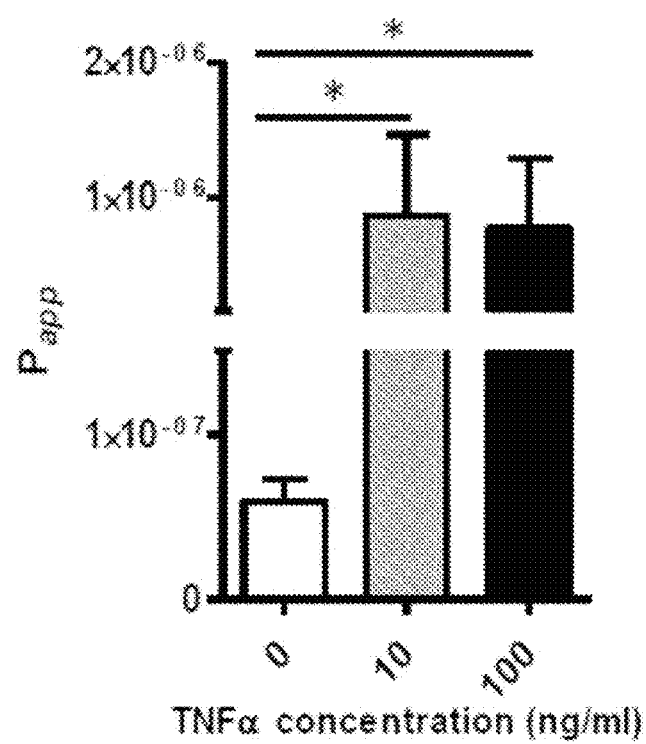

Figure 35
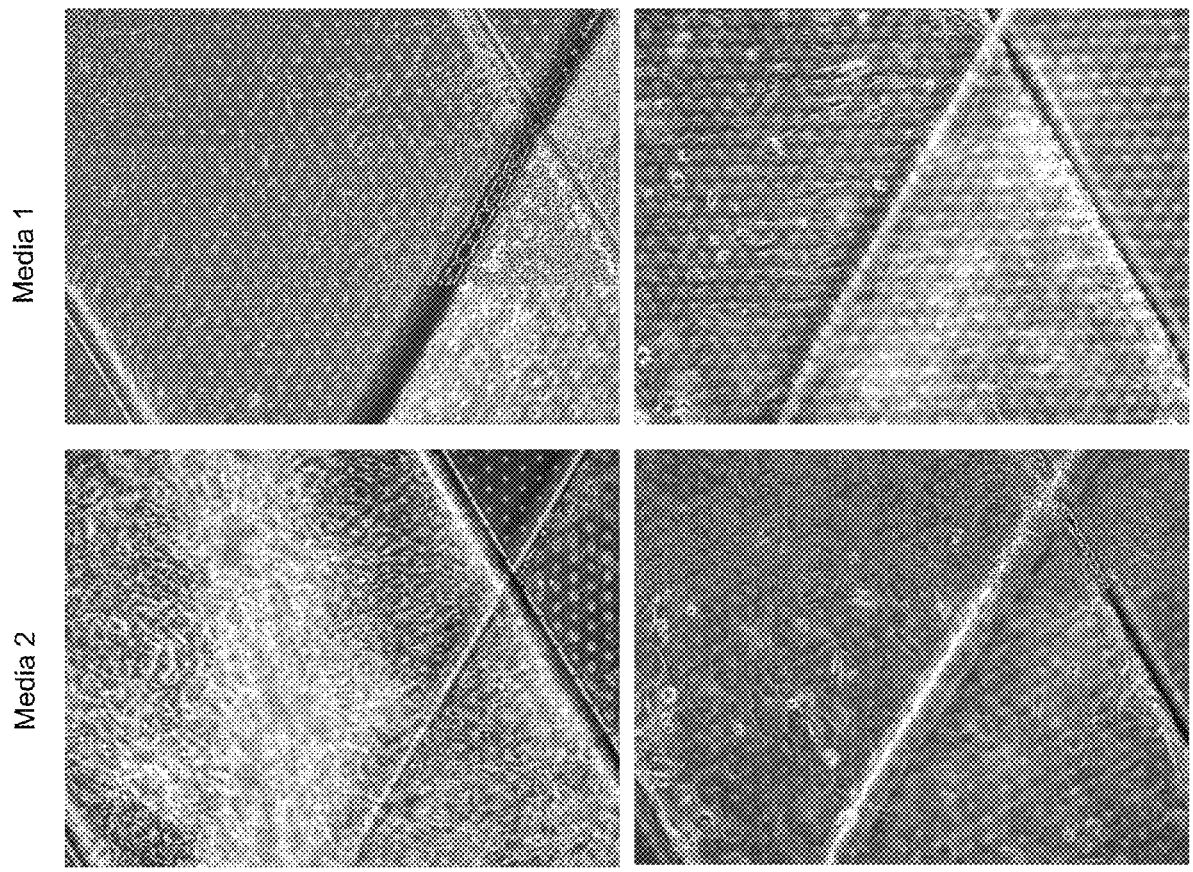
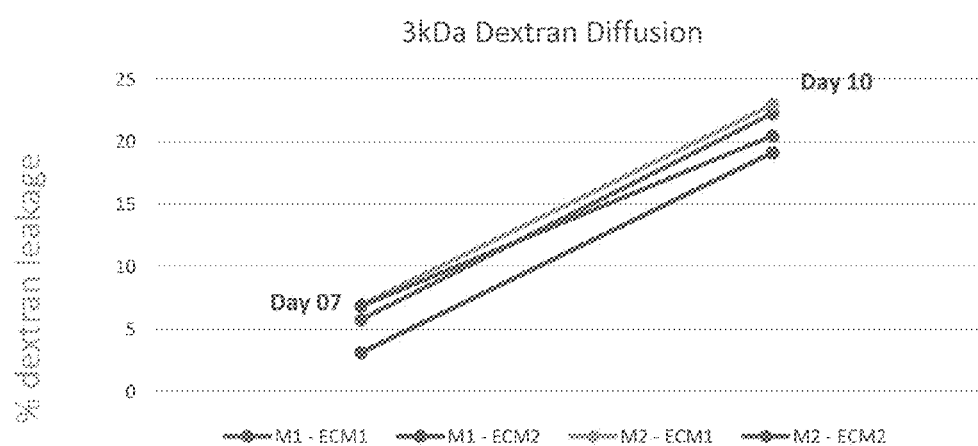

Figure 36
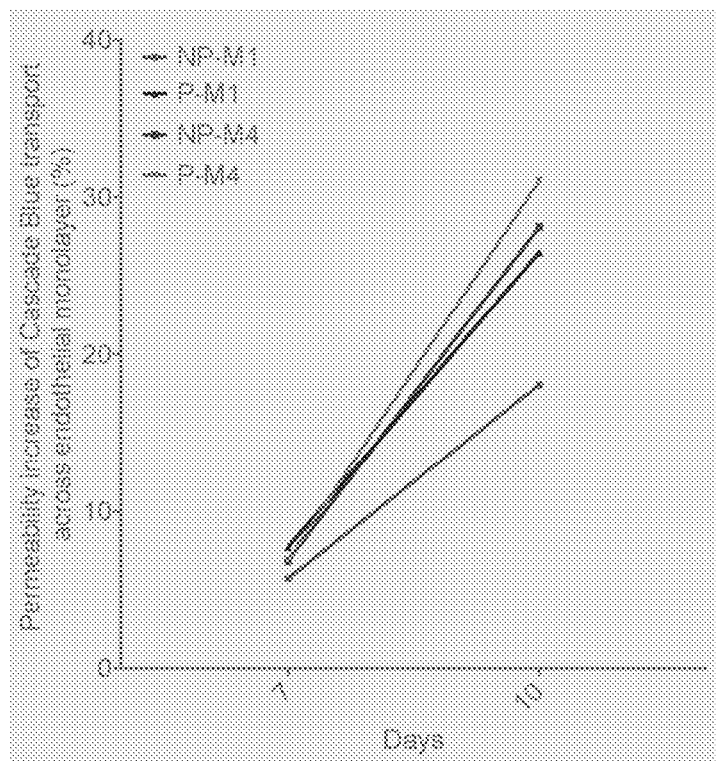
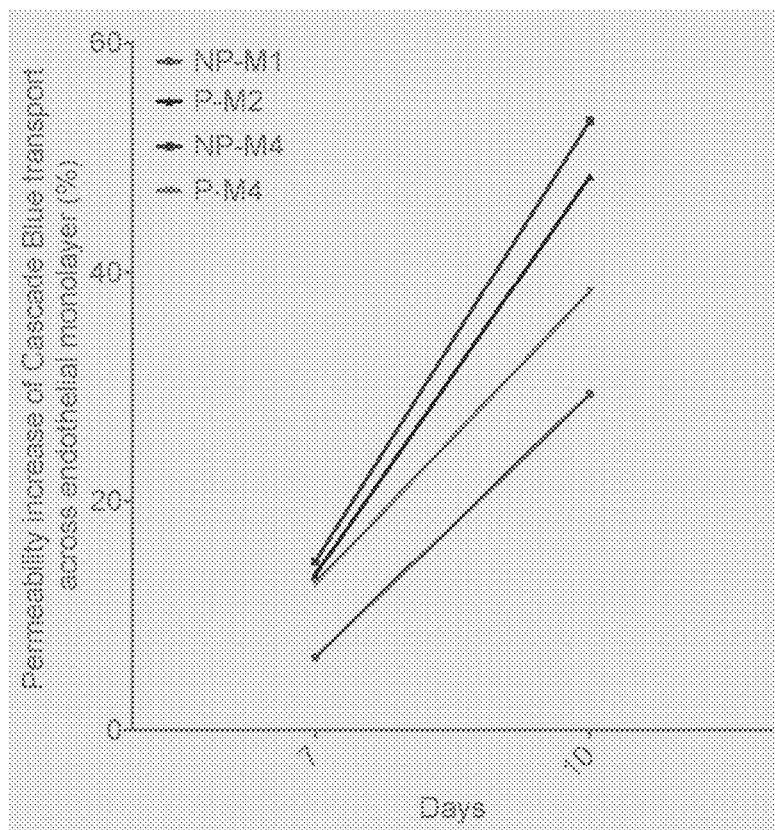

Figure 39
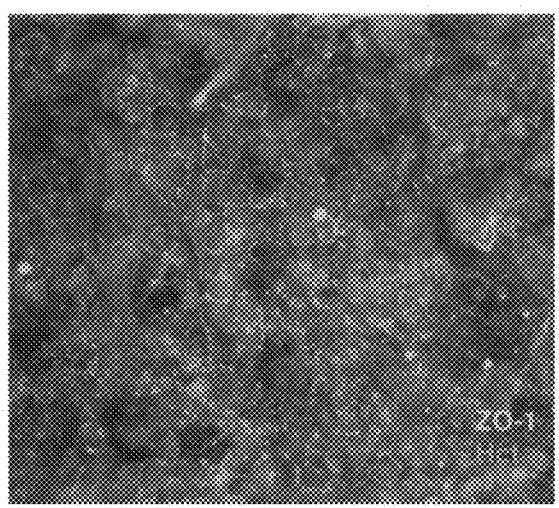
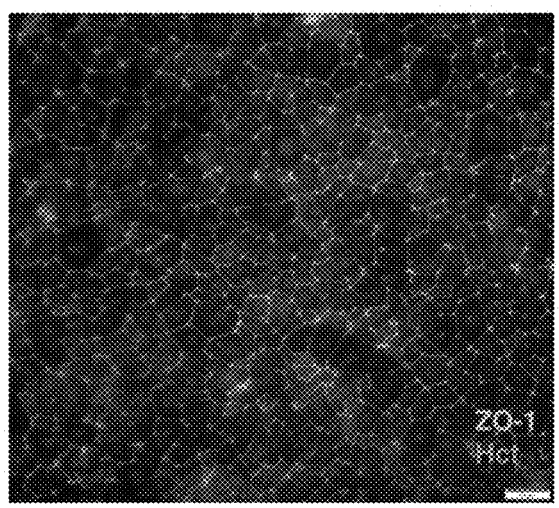
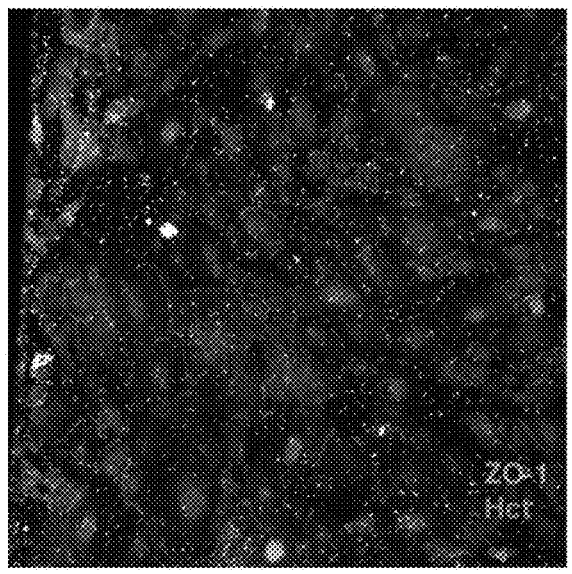
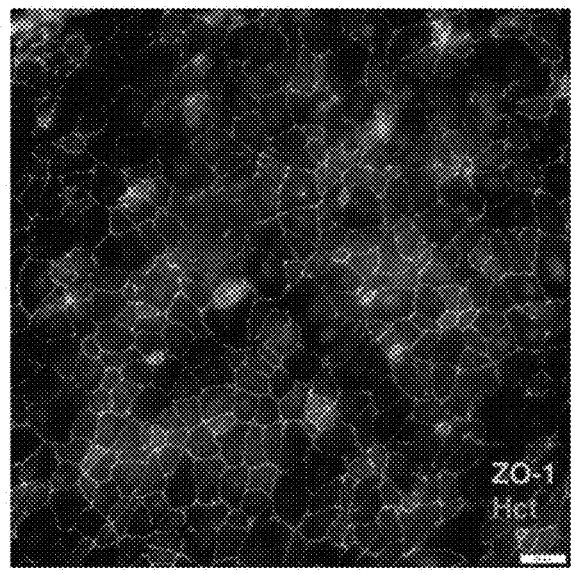

Figure 40
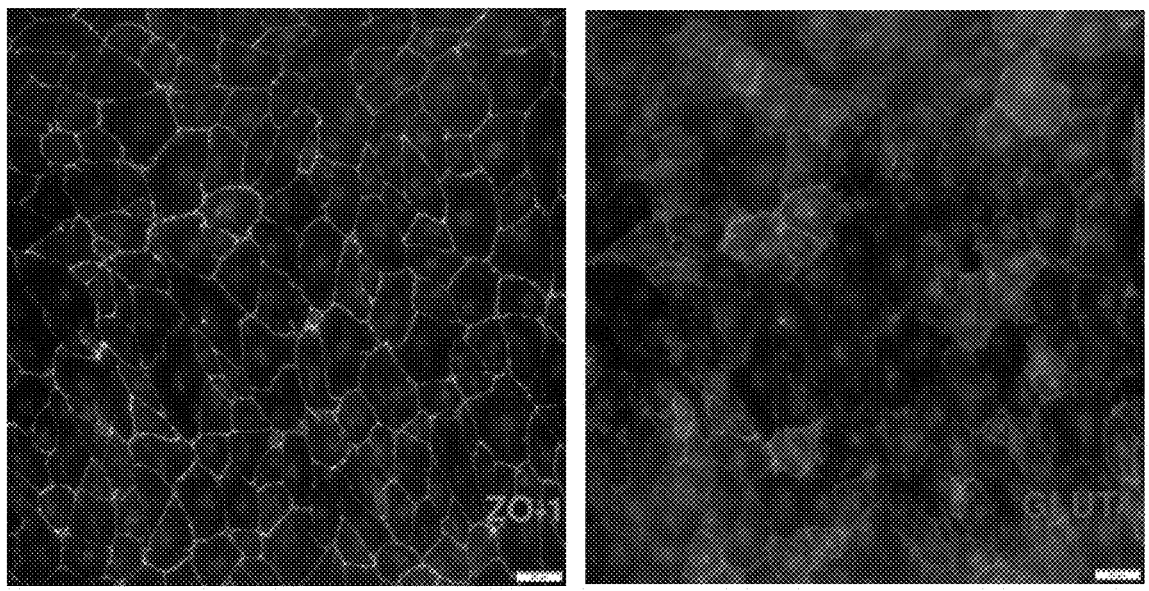
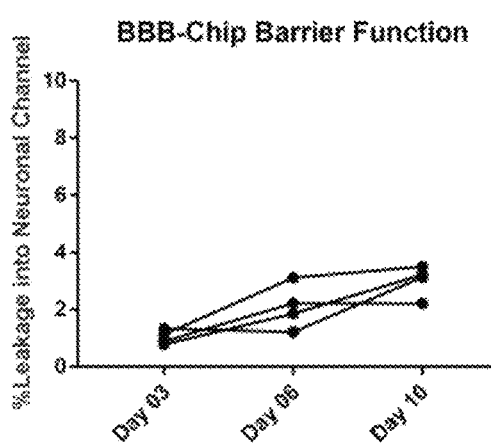
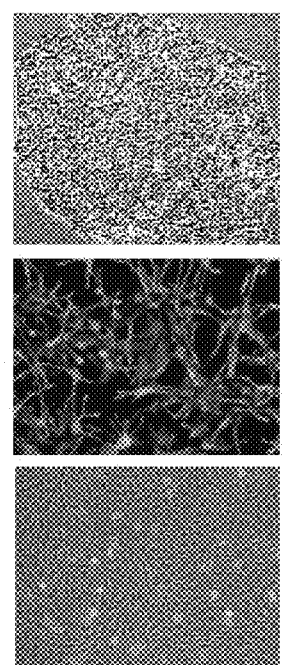

Figure 41A-B

RHEOLOGICALLY BIOMIMETIC FLUID SURROGATE

TECHNICAL FIELD

The present invention contemplates compositions, devices and methods of simulating biological fluids in a fluidic device, including but not limited to a microfluidic chip. In one embodiment, fluid comprising a colloid under flow in a microfluidic chip has a fluid density or viscosity similar to a bodily fluid, e.g. blood, lymph, lung fluid, or the like. In one embodiment, a fluid is provided as a rheologically biomimetic blood surrogate or substitute for simulating physiological shear stress and cell dynamics in fluidic device, including but not limited to immune cells.

BACKGROUND

Researchers who work with variables such as biological characteristics, including large cell types, fluidic channels larger than physiological dimensions (e.g. as compared to diameter of human blood vessels and capillaries), low viscosity medium (compared to human blood) and limited flow velocity pump systems (e.g. peristaltic or syringe pump) run into the problems with gravitational cell settling and/or fail to mimic rheology of human blood, e.g. mimic human physiologically relevant shear stress and pressure in vitro.

Many applications using cells suspended in buffer solution or media would benefit from having fluid conditions with physiologically relevant levels of shear stress, viscosity and/or pressure.

SUMMARY OF THE INVENTION

The present invention contemplates compositions, devices and methods of simulating biological fluids in a fluidic device, including but not limited to a microfluidic chip. In one embodiment, fluid comprising a colloid under flow in a microfluidic chip has a fluid density or viscosity similar to a bodily fluid, e.g. blood, lymph, lung fluid, or the like. In one embodiment, a fluid is provided as a rheologically biomimetic blood surrogate or substitute for simulating physiological shear stress and cell dynamics in fluidic device, including but not limited to immune cells.

The present invention also contemplates exposing differentiated cells in the microfluidic device to a variety of agents, whether naturally occurring on not, including drugs and drug candidates.

In one embodiment, the present invention contemplates the use of a density-modifying reagent (or a viscosity-modifying reagent or a buoyancy-modifying reagent) in a microfluidic chip to improve cell performance and/or interaction.

The present invention also contemplates devices. In one embodiment, the present invention contemplates a fluidic device comprising a membrane and a fluid, said fluid comprising a density-modifying reagent. In one embodiment, the present invention contemplates a fluidic device without a membrane and a fluid, said fluid comprising a density-modifying reagent. In one embodiment, said fluidic device comprises a microfluidic device wherein said membrane is positioned in a microchannel. In one embodiment, said fluid further comprises immune cells. In one embodiment, said density-modifying reagent comprises a colloid. In one embodiment, said density-modifying reagent comprises particles (e.g. beads). In one embodiment, said density-modifying reagent comprises silicone particles. In one embodiment, said wherein the density-modifying reagent comprises Percoll. In one embodiment, said wherein the density-modifying reagent comprises Ficoll. In one embodiment, said fluid comprises cell culture media. In one embodiment, said fluid comprises a buffer. In one embodiment, said fluid is a user-provided medium.

In one embodiment, the present invention contemplates a method comprising a) providing i) a fluid comprising a density-modifying reagent and ii) a fluidic device comprising a membrane, and b) contacting said fluidic device with said fluid. In one embodiment, the present invention contemplates a method comprising a) providing i) a fluid comprising a density-modifying reagent and ii) a fluidic device without a membrane, and b) contacting said fluidic device with said fluid. In one embodiment, said fluid further comprises immune cells. In one embodiment, said density-modifying reagent comprises a colloid. In one embodiment, said density-modifying reagent comprises particles (e.g. beads). In one embodiment, said density-modifying reagent comprises silicone particles. In one embodiment, said density-modifying reagent comprises Percoll. In one embodiment, said density-modifying reagent comprises Ficoll. In one embodiment, said fluid comprises cell culture media. In one embodiment, said fluid is a buffer. In one embodiment, said fluid is a user-provided medium. In one embodiment, said fluidic device comprises a microfluidic device, wherein said membrane is positioned in a microchannel. In one embodiment, first cells are adhered to a first surface of said membrane. In one embodiment, second cells are adhered to a second surface of said membrane. In one embodiment, said first cells are epithelial cells and said second cells are endothelial cells. In one embodiment, said fluid is introduced into said microchannel such that it is flowing at a flow rate. In one embodiment, said flowing fluid comprises immune cells and a portion of said immune cells adhere to said endothelial cells.

In one embodiment, the present invention contemplates a fluidic device comprising a membrane and a fluid, said fluid comprising a viscosity-modifying reagent. In one embodiment, the present invention contemplates a fluidic device without a membrane and a fluid, said fluid comprising a viscosity-modifying reagent. In one embodiment, said fluidic device comprises a microfluidic device wherein said membrane is positioned in a microchannel. In one embodiment, said fluid further comprises immune cells. In one embodiment, said viscosity-modifying reagent comprises a colloid. In one embodiment, said viscosity-modifying reagent comprises particles (e.g. beads). In one embodiment, said viscosity-modifying reagent comprises silicone particles. In one embodiment, said viscosity-modifying reagent comprises Percoll. In one embodiment, said viscosity-modifying reagent is comprises Ficoll. In one embodiment, said fluid is a cell media. In one embodiment, said fluid is a buffer. In one embodiment, said fluid is a user-provided medium.

In one embodiment, the present invention contemplates a method comprising a) providing i) a fluid comprising a viscosity-modifying reagent and ii) a fluidic device comprising a membrane, and b) contacting said fluidic device with said fluid. In one embodiment, the present invention contemplates a method comprising a) providing i) a fluid comprising a viscosity-modifying reagent and ii) a fluidic device without a membrane, and b) contacting said fluidic device with said fluid. In one embodiment, said fluid further comprises immune cells. In one embodiment, said viscosity-modifying reagent comprises a colloid. In one embodiment, said viscosity-modifying reagent comprises particles (e.g.

beads). In one embodiment, said viscosity-modifying reagent comprises silicone particles. In one embodiment, said viscosity-modifying reagent comprises Percoll. In one embodiment, said viscosity-modifying reagent comprises Ficoll. In one embodiment, said fluid is a buffer. In one embodiment, said fluid is a user-provided medium. In one embodiment, said fluidic device comprises a microfluidic device wherein said membrane is positioned in a microchannel. In one embodiment, first cells are adhered to a first surface of said membrane. In one embodiment, second cells are adhered to a second surface of said membrane. In one embodiment, said first cells are epithelial cells and said second cells are endothelial cells. In one embodiment, said fluid is introduced into said microchannel such that it is flowing at a flow rate. In one embodiment, said flowing fluid comprises immune cells and a portion of said immune cells adhere to said endothelial cells.

In one embodiment, the present invention contemplates a method, comprising: a) providing i) a microfluidic device comprising a body comprising a microchannel therein, said microchannel comprising cells; and ii) a fluid, said fluid comprising a density-modifying reagent and one or more immune cell types; and b) introducing said fluid into said microchannel under conditions such that the density-modifying reagent allows for said one or more immune cell types to interact with said cells in said microchannel. In one embodiment, said one or more immune cell types to interact with said cells in said microchannel without the use of gravity. In one embodiment, said cells in said microchannel comprise endothelial cells. In one embodiment, said density-modifying reagent promotes the attachment of one or more immune cell types to said endothelial cells in said microchannel. In one embodiment, said endothelial cells are in a layer on a membrane, the membrane disposed within at least a portion of the microchannel. In one embodiment, said membrane is coated with at least one attachment molecule that supports adhesion of a plurality of living cells. In one embodiment, said membrane is a porous membrane. In one embodiment, said membrane is at least partially flexible. In one embodiment, said membrane is configured to separate the microchannel into first and second microchannels. In one embodiment, endothelial cells are on the bottom of the membrane. In one embodiment, epithelial cells are on the top of the membrane. In one embodiment, said density modifying reagent is a colloid. In one embodiment, said density modifying reagent comprises particles (e.g. beads, microbeads, nanobeads, etc.) In one embodiment, said colloid is a silica-based colloid. In one embodiment, said silica-based colloid is Percoll. In one embodiment, said method further comprises, prior to step b), exposing said endothelial cells to an inflammatory cytokine. In one embodiment, said endothelial cells are from a healthy human patient. In one embodiment, said endothelial cells are from a human patient with symptoms of an inflammatory or autoimmune disorder.

In one embodiment, the present invention contemplates a method, comprising, a) providing i) a microfluidic device comprising a body comprising a membrane therein, said membrane comprising cells; and ii) a fluid, said fluid comprising a density-modifying reagent and one or more immune cell types; and b) introducing said fluid into said device under conditions such that the density-modifying reagent allows for said one or more immune cell types to interact with said cells on said membrane. In one embodiment, said one or more immune cell types to interact with said cells without the use of gravity. In one embodiment, said cells on said membrane comprise endothelial cells. In one embodiment, said density-modifying reagent promotes the attachment of one or more immune cell types to said endothelial cells. In one embodiment, said endothelial cells are in a layer on said membrane, the membrane disposed within at least a portion of a microchannel in said device. In one embodiment, said membrane is coated with at least one attachment molecule that supports adhesion of a plurality of living cells. In one embodiment, said membrane is a porous membrane. In one embodiment, said membrane is at least partially flexible. In one embodiment, said membrane is configured to separate the microchannel into first and second microchannels. In one embodiment, said endothelial cells are on the bottom of the membrane. In one embodiment, said epithelial cells are on the top of the membrane. In one embodiment, said density modifying reagent comprises a colloid. In one embodiment, said density modifying reagent comprises particles (e.g. beads, microbeads, nanobeads, nanoparticles, etc.). In one embodiment, said colloid is a silica-based colloid. In one embodiment, said silica-based colloid is Percoll. In one embodiment, said method further comprises, prior to step b), exposing said endothelial cells to an inflammatory cytokine. In one embodiment, said endothelial cells are from a healthy human patient. In one embodiment, said endothelial cells are from a human patient with symptoms of an inflammatory or autoimmune disorder.

In some embodiments, a microfluidic platform for the studies of immune cell recruitment and infiltration (e.g. in the context of chronic intestinal inflammation) is desired. Such a system allows for the assessment of the efficacy of drugs which are targeting important steps and components of this process (MadCAM1, integrins, e.g. alpha4beta7). In one embodiment, the present invention contemplates adhesion of immune cells (e.g. lymphocytes, PBMCs, etc.) to endothelial cells in a microfluidic device (e.g. endos mimicking vascular walls) under flow generated shear forces. In one embodiment, intestine-specific endos (e.g. HIMECs), as opposed to the generic HUVECs used previously, are employed. HIMECs express MadCAM, whereas HUVECs do not. While not limited to any particular theory, it is believed such specific cells are advantageous for drug development, including but not limited to therapies that increase immune recruitment to aid intestinal pathologies. Again, without being limited to any particular theory, it is believed that therapies that target immune recruitment through MadCAM can lead to recruitment that is specific to the intestine and potentially with fewer off target effects/toxicity.

Fluidic devices are not limited to having a membrane, in fact, fluidic devices comprising a wall of gel and pillars instead of a membrane are contemplated. In one embodiment, a rheologically biomimetic blood surrogate is added to cells for providing a cell suspension, i.e. cells floating in a fluid. In another embodiment, a blood substitute mimics physiological shear stress on cells in suspension.

In some embodiments, a method is provided, comprising: a) providing i) a microfluidic device comprising a body comprising a microchannel therein, said microchannel comprising cells; and ii) a fluid, said fluid comprising a buoyancy-modifying reagent and one or more immune cell types; and b) introducing said fluid into said microchannel under conditions such that the buoyancy-modifying reagent allows for said one or more immune cell types to interact with said cells in said microchannel.

In some embodiments, a method is provided, comprising: a) providing i) a microfluidic device comprising a body comprising a microchannel therein, said microchannel comprising cells; and ii) a fluid, said fluid comprising a shear-modifying and one or more immune cell types; and b)

introducing said fluid into said microchannel under conditions such that the shear-modifying reagent allows for said one or more immune cell types to interact with said cells in said microchannel. In one embodiment, shear is increased. In another embodiment, shear is decreased.

In some embodiments, a method is provided using a density-modifying reagent (including but not limited to Percoll) as a substitute for high flow rate. For example, when using Percoll, the flow rate can be decreased (and yet the cells do not settle out and can interact). In some embodiments, a method is provided using Percoll as a substitute for low flow rates, including but not limited to sedimentation.

In some embodiments, a method is provided using Percoll as a substitute or additive for preventing cells from settling in reservoirs, tubing and channels (and the like) thus allowing the majority of cells in a cell population to remain in suspension (permitting cell interaction including but not limited to specific cellular attachment).

In some embodiments, a method is provided using a fluid modifying reagent that does not affect expression of adhesion molecules in cells. For example, it is preferred that that the modifying reagent not activate cells or cause an inflammatory response (when compared to the same cells exposed to normal culture media).

In some embodiments, fluids comprising modifying agents as described herein, are contemplated for use in assays associated with neutrophil recruitment in small airway chips. Small-airway Lung-On-Chip include but are not limited to (COPD; asthma, etc.). In some embodiments, a method is provided, comprising: a) providing, i) a fluidic device comprising a body comprising a channel therein, said channel comprising respiratory cells; and ii) a fluid, said fluid comprising a density-modifying reagent and one or more immune cell types; and b) introducing said fluid into said channel under conditions such that the density-modifying reagent allows for said one or more immune cell types to interact with said respiratory cells in said channel. In one embodiment, said one or more immune cell types to interact with said respiratory cells in said channel is without the use of gravity (e.g. against the force of gravity). In one embodiment, said density-modifying reagent is a colloid. In one embodiment, said colloid is a silica-based colloid. In one embodiment, said silica-based colloid is Percoll. In one embodiment, said Percoll ranges from 25% to 80% of said fluid. In one embodiment, said respiratory cells are bronchial cells. In one embodiment, said bronchial cells are mucociliary bronchiolar airway epithelial cells. In one embodiment, said cells in said channel comprise endothelial cells. In one embodiment, said density-modifying reagent promotes the attachment of one or more immune cell types to said endothelial cells in said channel. In one embodiment, said endothelial cells are in a layer on a membrane, the membrane disposed within at least a portion of said channel. In one embodiment, said membrane is coated with at least one attachment molecule that supports adhesion of a plurality of living cells. In one embodiment, said attachment molecule is selected from the group consisting of collagen IV, Matrigel, and molecules isolated from patient biopsies. In one embodiment, said membrane is a porous membrane. In one embodiment, said membrane is at least partially flexible. In one embodiment, said membrane is configured to separate said channel into first and second channels. In one embodiment, said endothelial cells are located on the bottom of said membrane. In one embodiment, said respiratory cells are on the top of said membrane. In one embodiment, said method further comprises, prior to the step of b), exposing said respiratory cells to an inflammatory cytokine. In one embodiment, said inflammatory cytokine stimulates said respiratory cells. In one embodiment, said inflammatory cytokine is IL-13. In one embodiment, said endothelial cells are from a healthy human patient. In one embodiment, said endothelial cells are from a human patient with symptoms of an inflammatory or autoimmune disorder. In one embodiment, said method further comprises, prior to the step of b), exposing said endothelial cells to an inflammatory cytokine. In one embodiment, said endothelial cells are stimulated. In one embodiment, said cytokine is IL-13. In one embodiment, said respiratory cells have a respiratory disease phenotype. In one embodiment, said respiratory disease phenotype is an asthma phenotype. In one embodiment, said respiratory disease phenotype is a COPD phenotype or a CF phenotype. In one embodiment, said respiratory cell in said fluid is under flow conditions. In one embodiment, said flow conditions comprise flowing air and/or flowing said fluid. In one embodiment, said endothelial cells in said fluidic device are subject to flow conditions. In one embodiment, said flow conditions comprise flowing said fluid. In one embodiment, said flow conditions comprise flowing blood and/or a blood substitute. In one embodiment, said method further comprising the step of measuring the extent of recruitment of said immune cells into said respiratory cells. In one embodiment, said method further comprising the step of measuring the extent of recruitment of said immune cells into said endothelium and/or epithelium. In one embodiment, said immune cells comprise neutrophils. In one embodiment, said respiratory cells of step b) are contacted by bacteria in step c). In one embodiment, said bacteria is *P. aeruginosa*. In one embodiment, said respiratory cells of step b) are contacted by fungi in step c). In one embodiment, said respiratory cells of step b) are contacted by a virus in step c). In one embodiment, said respiratory cells of step b) are contacted by a respiratory virus in step c). In one embodiment, said respiratory virus is selected from the group consisting of parainfluenza virus, influenza virus, rhinovirus, coronaviruses, human respiratory syncytial virus, and adenoviruses. In one embodiment, said hyperplasia is detected by counting cells. In one embodiment, said hyperplasia is detected by measuring cell size. In one embodiment, said method further comprising measuring cell size and/or number for at least one population of cells present in said fluidic device. In one embodiment, said method further comprising the step of c) exposing said respiratory cells to a test agent. In one embodiment, said test agent comprises a candidate drug. In one embodiment, said_test agent comprises a CXCR2 inhibitor. In one embodiment, said candidate drug reduces or prevents a severe respiratory disease phenotype. In one embodiment, said test agent is a steroid. In one embodiment, said method further comprising the step of c) measuring the concentration of at least one cytokine. In one embodiment, said method further comprising the step of c) detecting hyperplasia. In one embodiment, said hyperplasia is goblet cell hyperplasia. In one embodiment, said method further comprising the step of c) imaging the respiratory cells after step b). In one embodiment, said method further comprising the step of c) measuring the concentration of at least one cytokine after step b). In one embodiment, said fluidic device is a microfluidic device. In one embodiment, said channel is a microchannel.

A method, comprising: a) providing, i) a fluidic device comprising a body comprising a channel therein, said channel comprising lung epithelial cells; and ii) a fluid, said fluid comprising a density-modifying reagent and one or more immune cell types; and b) introducing said fluid into said channel under conditions such that the density-modifying reagent allows for said one or more immune cell types to interact with said lung epithelial cells in said channel. In one embodiment, said lung epithelial cells comprise alveolar type I cells and alveolar type II cells.

In some embodiments, a method is provided, comprising: a) providing, i) a fluidic device comprising a body comprising a channel therein, said channel comprising lung parenchymal cells; and ii) a fluid, said fluid comprising a density-modifying reagent and one or more immune cell types; and b) introducing said fluid into said channel under conditions such that the density-modifying reagent allows for said one or more immune cell types to interact with said lung parenchymal cells in said channel.

In some embodiments, a microfluidic device is provided comprising at least one microfluidic channel and a population of living cells positioned in at least a region of said microfluidic fluid channel, at least a portion of said cells capable of differentiating into terminally differentiated lung parenchyma cells. In one embodiment, said population of cells is selected from the group consisting of, organ-restricted adult stem cells (aSCs), embryonic stem cells (ESCs), pluripotent stem cells (PSCs), induced pluripotent stem cells (iPSCs), organoids and stem cells isolated from lung parenchyma biopsies. In one embodiment, said organoid is derived in vitro from cell populations selected from the group consisting of primary cells; primary respiratory tissues; primary lung tissues; stem cells; embryonic stem cells (ESCs); and induced pluripotent stem cells (iPS cells). In one embodiment, said organoid is selected from the group consisting of a tracheosphere, a bronchosphere, and an alveolosphere. In one embodiment, said device further comprising a membrane in said at least one fluid channel, said population of living cells positioned in at least a region of said membrane. In one embodiment, said population of cells are partially differentiated into progenitor cells. In one embodiment, said progenitor cell population comprises SOX17+ cells. In one embodiment, said progenitor cell population comprises NKX2-1+ cells. In one embodiment, said progenitor cells are selected from the group consisting of proximal progenitor cells and distal progenitor cells. In one embodiment, said progenitor cells comprise SOX9+ cells. In one embodiment, said progenitor cells comprise SOX2+ cells. In one embodiment, said terminally differentiated lung parenchyma cells are selected from the group consisting of alveolar type I cells, alveolar type II cells, ciliated epithelial cells, basal cells, goblet cells, and club cells. In one embodiment, said population of cells does not contain a terminally differentiated lung parenchyma cell. In one embodiment, said membrane comprises one or more types of extracellular matrix proteins attached to said membrane. In one embodiment, said cells are positioned at an air-liquid interface.

In one embodiment, a method is provided, comprising: a) providing; i) a population of living cells, wherein at least a portion of said cells have the capability to differentiate into a terminally differentiated lung parenchyma cell; ii) a microfluidic device comprising at least one microfluidic channel; and iii) a fluid, said fluid comprising a density-modifying reagent and one or more immune cell types; and b) introducing said cells into said at least one microfluidic channel under conditions such that said cells are positioned in at least a region of said microfluidic device so as to create positioned cells; and c) exposing said positioned cells to conditions that cause at least a portion of said cells to differentiate into terminally differentiated lung parenchyma cells, and d) introducing said fluid into said microchannel under conditions such that the density-modifying reagent allows for said one or more immune cell types to interact with said terminally differentiated lung parenchyma cells in said microchannel. In one embodiment, said microfluidic device further comprises a membrane positioned in at least a region of said microfluidic device, said cells positioned after step b) on at least a region of said membrane. In one embodiment, said population of cells of step a) is selected from the group consisting of organ-restricted adult stem cells (aSCs), embryonic stem cells (ESCs), pluripotent stem cells (PSCs), induced pluripotent stem cells (iPSCs), organoids and stem cells isolated from lung parenchyma biopsies. In one embodiment, said organoid is derived in vitro from cell populations selected from the group consisting of primary cells; primary respiratory tissues; primary lung tissues; stem cells; embryonic stem cells (ESCs); and induced pluripotent stem cells (iPS cells). In one embodiment, said organoid is selected from the group consisting of a tracheosphere and a bronchosphere, and an alveolosphere. In one embodiment, said population of cells of step a) are partially differentiated into progenitor cells. In one embodiment, said progenitor cell population comprises SOX17+ cells. In one embodiment, said progenitor cell population comprises NKX2-1+ cells.

In some embodiments, fluids comprising modifying agents as described herein, are contemplated for use in assays associated with T cell recruitment assays in Intestine Chips.

In some embodiments, fluids comprising modifying agents as described herein, are contemplated for use in assays associated with peripheral blood mononuclear cell (PBMC) recruitment assays in Intestine Chips.

In one embodiment, a method is provided comprising: a) providing, i) a fluidic device comprising a body comprising a channel therein, said channel comprising intestinal cells; and ii) a fluid, said fluid comprising a density-modifying reagent and one or more immune cell types; and b) introducing said fluid into said channel under conditions such that the density-modifying reagent allows for said one or more immune cell types to interact with said intestinal cells in said channel. In one embodiment, said one or more immune cell types to interact with said cells in said microchannel without the use of gravity (e.g. against the force of gravity). In one embodiment, said density-modifying reagent is a colloid. In one embodiment, said colloid is a silica-based colloid. In one embodiment, said silica-based colloid is Percoll. In one embodiment, said cells in said channel comprises endothelial cells. In one embodiment, said endothelial cells are in a layer on a membrane, the membrane disposed within at least a portion of said channel. In one embodiment, said density-modifying reagent promotes the attachment of one or more immune cell types to said endothelial cells in said channel. In one embodiment, said membrane is coated with at least one attachment molecule that supports adhesion of a plurality of living cells. In one embodiment, said membrane is a porous membrane. In one embodiment, said membrane is at least partially flexible. In one embodiment, said membrane is configured to separate said channel into first and second channels. In one embodiment, said endothelial cells are on the bottom of the membrane. In one embodiment, said epithelial cells are on the top of the membrane. In one embodiment, said method further comprises, prior to step b), exposing said endothelial cells to an inflammatory cytokine. In one embodiment, said endothelial cells are from a healthy human patient. In one embodiment, said endothelial cells are from a human patient with symptoms of an inflammatory or autoimmune disorder.

In one embodiment, said fluidic device is a microfluidic device. In one embodiment, said channel is a microchannel.

In one embodiment, a method is provided comprising: a) providing, i) a fluidic device comprising a body comprising a channel therein, said channel comprising brain cells; and ii) a fluid, said fluid comprising a density-modifying reagent and one or more immune cell types; and b) introducing said fluid into said channel under conditions such that the density-modifying reagent allows for said one or more immune cell types to interact with said brain cells. In one embodiment, said brain cells are endothelial cells, e.g. human brain endothelial cells. In one embodiment, said brain cells are neurons. In one embodiment, said brain cells comprise a layer of neurons and a layer of endothelial cells so as to mimic the blood brain barrier.

In one embodiment, a method is provided comprising: a) providing, i) a fluidic device comprising a body comprising a channel therein, said channel comprising kidney epithelial cells; and ii) a fluid, said fluid comprising a density-modifying reagent and one or more immune cell types; and b) introducing said fluid into said channel under conditions such that the density-modifying reagent allows for said one or more immune cell types to interact with said kidney epithelial cells in said channel. In one embodiment, said one or more immune cell types to interact with said cells in said microchannel without the use of gravity (e.g. without using gravity to force the cells in a particular direction or, more preferably, allowing for the cells to move in a direction against the force of gravity). In one embodiment, said density-modifying reagent is a colloid. In one embodiment, said colloid is a silica-based colloid. In one embodiment, said silica-based colloid is Percoll. In one embodiment, said cells in said channel comprises endothelial cells. In one embodiment, said endothelial cells are in a layer on a membrane, the membrane disposed within at least a portion of said channel. In one embodiment, said density-modifying reagent promotes the attachment of one or more immune cell types to said endothelial cells in said channel. In one embodiment, said membrane is coated with at least one attachment molecule that supports adhesion of a plurality of living cells. In one embodiment, said membrane is a porous membrane. In one embodiment, said membrane is at least partially flexible. In one embodiment, said membrane is configured to separate said channel into first and second channels. In one embodiment, said endothelial cells are on the bottom of the membrane. In one embodiment, said epithelial cells are on the top of the membrane. In one embodiment, said method further comprises, prior to step b), exposing said endothelial cells to an inflammatory cytokine. In one embodiment, said endothelial cells are from a healthy human patient. In one embodiment, said endothelial cells are from a human patient with symptoms of an inflammatory or autoimmune disorder. In one embodiment, said fluidic device is a microfluidic device. In one embodiment, said channel is a microchannel.

In one embodiment, a method is provided, comprising: a) providing, i) a fluidic device comprising a body comprising a channel therein, said channel comprising hepatocyte cells; and ii) a fluid, said fluid comprising a density-modifying reagent and one or more immune cell types; and b) introducing said fluid into said channel under conditions such that the density-modifying reagent allows for said one or more immune cell types to interact with said hepatocyte cells in said channel. In one embodiment, said one or more immune cell types to interact with said cells in said microchannel without the use of gravity (e.g. without using gravity to force the cells in a particular direction or, more preferably, allowing for the cells to move in a direction against the force of gravity). In one embodiment, said density-modifying reagent is a colloid. In one embodiment, said colloid is a silica-based colloid. In one embodiment, said silica-based colloid is Percoll. In one embodiment, said cells in said channel comprises endothelial cells. In one embodiment, said cells in said channel comprises endothelial cells. In one embodiment, said endothelial cells are Liver Sinusoidal Endothelial Cells ("LSEC"). In one embodiment, said endothelial cells are in a layer on a membrane, the membrane disposed within at least a portion of said channel. In one embodiment, said density-modifying reagent promotes the attachment of one or more immune cell types to said endothelial cells in said channel. In one embodiment, said membrane is coated with at least one attachment molecule that supports adhesion of a plurality of living cells. In one embodiment, said membrane is a porous membrane. In one embodiment, said membrane is at least partially flexible. In one embodiment, said membrane is configured to separate said channel into first and second channels. In one embodiment, said endothelial cells are on the bottom of the membrane. In one embodiment, said epithelial cells are on the top of the membrane. In one embodiment, said method further comprises, prior to step b), exposing said endothelial cells to an inflammatory cytokine. In one embodiment, said endothelial cells are from a healthy human patient. In one embodiment, said endothelial cells are from a human patient with symptoms of an inflammatory or autoimmune disorder. In one embodiment, said fluidic device is a microfluidic device. In one embodiment, said channel is a microchannel.

In one embodiment, a method is provided comprising: a) providing, i) a fluidic device comprising a body comprising a channel therein, said channel comprising epithelial skin cells; and ii) a fluid, said fluid comprising a density-modifying reagent and one or more immune cell types; and b) introducing said fluid into said channel under conditions such that the density-modifying reagent allows for said one or more immune cell types to interact with said epithelial skin cells in said channel.

In one embodiment, a method is provided comprising: a) providing, i) a fluidic device comprising a body comprising a channel therein, said channel comprising cancer cells; and ii) a fluid, said fluid comprising a density-modifying reagent and one or more immune cell types; and b) introducing said fluid into said channel under conditions such that the density-modifying reagent allows for said one or more immune cell types to interact with said cancer cells in said channel.

In some embodiments, a fluid comprising a modifying reagent is contemplated for use in Kidney Chips, not associated with recruitment of immune cells.

However, it is not intended that the present invention be limited to these embodiments. For example, the present invention contemplates combining features from different embodiments (as discussed below). In addition, the present invention contemplates removing features from the embodiments (as discussed below). Furthermore, the present invention contemplates substituting features in the embodiments (as discussed below).

Definitions

As used herein, the terms "particles" and "particulates" refers broadly to a constituents of matter, both viable (living) and non-viable (non-living). As one example, a particle refers to a cell, such as a cell within a fluid, including both cells normally present in the blood of healthy patient (white cell, red cell, platelets, etc.), cells not normally present into the bloodstream such as circulating tumor cells. However, the fluid is not limited to blood, i.e. cells are found in fluids, such as macrophages found in lung fluid, etc. As another example, a particle refers to microorganisms, e.g., spores, virions, bacterium, such as found in normal flora or present in diseased states, and microscopic physical particles/particulates, including but not limited to pollutants, as well as any physical particles/particulates that could enter the blood stream or other bodily fluid. Particles also include beads and the like, which can be conveniently used in some embodiments in place of cells in order to take measurements or otherwise evaluate a parameter, e.g. flow rate, buoyancy, viscosity, shear, etc.

As used herein, the term "sediment" refers to a piece of matter, such as a particle, that settles to a surface, such as when particles or cells settle onto the bottom of a container of liquid or are deposited on a surface (i.e. barrier), such as the bottom of a microchannel.

As used herein, the term "settling out" or "sedimentation" refers to the process or action as a piece of matter, such as a particle, that is settling, or being deposited as sediment, onto a surface. As one non-limiting example, settling out refers to when a particle in solution moves to the bottom of a fluid channel, reservoir or containment tank, when the particle's density is greater than the density of the fluid in which it is immersed.

As used herein, the term "rheology" refers to the flow and deformation of fluids, gases and solids under the influence of mechanical forces. In other words, rheology may be referred to as physics relating to non-Newtonian flow and Newtonian flow of liquids, soft solids, solids and gases.

As used herein, the term "Newtonian" in reference to a fluid refers to viscosity (i.e. Newtonian viscosity) relating to temperature of the fluid, that is primarily independent of shear (strain) rate, time, etc., at a constant temperature, e.g. water, mineral oil, gasoline, alcohol, etc. These "Newtonian" fluids have a linear relationship between viscosity and shear stress. Examples, such as water, ethanol, air, may be considered Newtonian fluids.

In contrast, when shear is applied to "non-Newtonian fluids", the viscosity of the fluid changes, either up or down depending upon the fluid. Fluids such as slurries, suspensions, gels, colloids, etc., are considered "non-Newtonian" fluids. As used herein, the term "non-Newtonian" in reference to a fluid refers to a fluid that does not follow Newton's law of viscosity, as one example, non-linear rheology of blood in microchannels.

As used herein, the term "blood rheology" refers to flow properties of blood and its elements of plasma and cells.

As used herein, the term "biomimetic" or "biomimicry" refers to materials, e.g. fluids, membranes, etc., synthetic systems, synthetic devices, machines etc., that have functions that mimic a biological process or biological component, e.g. blood, intestinal contents, lung fluid, etc.

As used herein, the term "blood surrogate" used to mimic at least one function (e.g. supporting cells) or parameter (e.g. viscosity) of biological blood, including but not limited to blood in a device such as in a microfluidic chip.

As used herein, the term "fluid-modifying reagent" refers to a compound for altering one or more characteristics of a fluid, including but not limited to density, viscosity, flowability, buoyancy, shear rate, etc. For one example, a particle(s) in a fluid sample comprising a fluid-modifying reagent exhibits characteristics that are different when compared to the characteristic of duplicate particle(s) in an identical fluid sample but without fluid-modifying reagent. Non-limiting examples of particle characteristics may include a faster or a slower sedimentation rate under identical conditions. Examples of a fluid-modifying reagent include but are not limited to: a density-modifying reagent, a viscosity-modifying reagent, a buoyancy-modifying reagent, etc.

As used herein, the term "colloid" refers to a homogeneous, noncrystalline substance consisting of large molecules or ultramicroscopic particles of one substance dispersed through a second substance. Colloids include gels, sols, and emulsions; the particles do not settle and cannot be separated out by ordinary filtering or centrifuging like those in a suspension.

As used herein, the term "density-modifying reagent" refers to a compound, such as colloidal silica coated with polyvinyl-pyrrolidine (e.g. Percoll), for use in changing the density of a fluid (i.e. liquid). For one example, a cell may sink to the bottom of a tube containing cell media, whereas the addition of a density-modifying reagent to the cell media may slow the downward movement of a cell in the density-modified fluid. When the density of the media is modified to be substantially equal to the density of a specific type of particulate solid, i.e. a lymphocyte, then the downward movement may be almost stopped without the influence of other downward acting forces.

As used herein, the term "viscosity" or "n" refers to the resistance of a liquid or gas to flow, i.e. more particularly to internal forces within a substance, also a measure of fluid friction. In other words, liquids and gases with low internal friction will flow very easily while high internal friction reduces flowability. Thus, increasing viscosity causes a gas or liquid to be less capable of flowing. Further, the viscosity value of a liquid is related to it's density, and the density of a fluid is related to its buoyancy.

As used herein, "thickening agent" or "thickener" or "viscosity modifying reagent" or "VMA" refers to a substance for changing the viscosity of the fluid, e.g. addition of a thickening agent increases the viscosity of a liquid without substantially changing its other properties.

As used herein, the term "shear stress" in general refers to an applied force per unit area, acting parallel to a surface element. Shear stress is primarily caused by friction between fluid particles, related to fluid viscosity, and a component of shear strain. τ (Greek: tau) refers to a combined effect of viscosity and relative velocities where the stress is parallel to the surface of the material, as opposed to normal stress when the stress is perpendicular to the surface. Shear stress is relevant to the motion of fluids upon surfaces, which result in the generation of shear stress.

As used herein, the term "shear rate" or "shear strain" refers to the rate of change of velocity at which one layer of fluid passes over an adjacent layer. "Shear rate" is also referred to as γ, (Greek: gamma G) or "rate of shear". In a non-Newtonian fluid, such as blood, the relationship between shear stress and shear rate is different.

As used herein, the term "buoyancy" refers to a phenomenon where an object less dense than the fluid it rests upon or within will float in the fluid. In other words, the ability of particulate matter to float in fluid, e.g. water, cell media, etc. More specifically, buoyancy (or "upthrust") refers to Archimedes' principle where a fluid will exert an upward force on an object immersed in it equal to the weight of the fluid displaced by the object, thus an object that is immersed in a fluid is buoyed up by a force equal to the weight of the fluid displaced by the object. An object that has neutral buoyancy will neither sink nor rise, unless impacted by other forces.

As used herein, "buoyancy-modifying reagent" refers to a substance for changing the density of a fluid. Thus, in one embodiment, a buoyancy modifying reagent added to a fluid may alter a suspended particle's sedimentation rate. In other words, after adding a buoyancy-modifying reagent to a fluid for increasing the fluid density, a suspended particle's sedimentation rate may be reduced. In another embodiment, after adding a buoyancy modifying reagent to a fluid for decreasing the fluid density, a suspended particle's sedimentation rate may be increased. Exemplary nonlimiting examples include but are not limited to agents used for differential centrifugation, such as Percoll and Ficoll, alginic acid type III, carrageenan type I, carrageenan type II, cellulose type 20, 50, and i00, guar gum, locust gum, xanthan gum, apple pectin, citrus pectin, xylan (all obtained from Sigma Chem. Co., St. Louis, Mo.), SeaKem HGT agarose (FMC Corp., Rockland, Me.), Gelrite gellan gum (Kelco Div. of Merck & Co., San Diego, Calif.), and Bacto-agar (Difco Labs, Detroit, Mich.). The concentration of agent tested ranges approximately 0.0002%. to 0.4%, 0.4%-1%, 1%-80%.

As used herein, "Peripheral blood mononuclear cells" or "PBMCs" refers to any peripheral (circulating) blood cell having a round or single lobed nucleus. "PBMCs" include lymphocytes (T cells, B cells, NK cells) and monocytes, (i.e. agranulocytes) whereas erythrocytes and platelets, which are not considered PBMCs, have no nuclei. In contrast to PBMCs, granulocytes, such as "polymorphonuclear leukocytes" or "PMN" or "PML" or "PMNL" refers to white blood cells having varying shapes of the nucleus, which is usually lobed into three segments (e.g. neutrophils, basophils, eosinophils, and mast cells) have multi-lobed nuclei.

As used herein, "White blood cells" or "WBCs" or "leukocytes" refers to cells that lack hemoglobin, including but not limited to: neutrophils, eosinophils, basophils, lymphocytes, monocytes, and macrophages.

As used herein, "Mononuclear leukocytes" refers to PBMCs and WBCs having a round or single lobed nucleus, such as lymphocytes, monocytes, macrophages, and dendritic cells.

As used herein, "lymphocytes" refer to white blood cells including T-cells, B-cells, Natural Killer (NK) cells, and their differentiated cell types such as cytotoxic T cells. Although some differentiated lymphocyte cell types contain granules, such as cytotoxic T cells, plasma cells, etc., they are not considered granulocytes.

As used herein, the term "biopsy" refers to a sample of the tissue that is removed from a body.

As used herein, the term "inflammation" refers to an in vivo physical condition in which a part of tissue or cells may become activated, reddened, swollen (enlarged), or damaged (ulcerated) especially as a reaction to injury or an irritant. In the body, areas of inflammation can have increased blood flow and capillary permeability, i.e. changes in endothelial cells lining capillaries resulting in capillary dilation and leukocyte infiltration into the irritated and/or inflamed tissues, along with activated immune cells, including white blood cells, leukocytes, lymphocytes, etc., including substances produced by activated immune cells. Inflammation may occur suddenly (acute) or gradually over time (chronic). Inflammation may be local, i.e. in one location as a "patch" or "spot" or may be in several areas as numerous patches, including ulcers, or contiguous involving a large area of tissue. Inflammation may be limited to epithelial regions and underlying endothelium or stromal regions (for example, mucosal areas), or may extend to the submucosa, or extend to the muscularis propria and may further extent to the outermost layer, adventitia, in contact with other parts of the body. Inflammation may also refer to a physiological condition in vitro, as described herein for cells in microfluidic devices.

The term "microfluidic" as used herein relates to components where moving fluid is constrained in or directed through one or more channels wherein one or more dimensions are 1 mm or smaller (microscale). Microfluidic channels may be larger than microscale in one or more directions, though the channel(s) will be on the microscale in at least one direction. In some instances the geometry of a microfluidic channel may be configured to control the fluid flow rate through the channel (e.g. increase channel height to reduce shear). Microfluidic channels can be formed of various geometries to facilitate a wide range of flow rates through the channels (and some of these designs are shown by way of example, in the figures).

"Channels" are pathways (whether straight, curved, single, multiple, in a network, etc.) through a medium (e.g., silicon) that allow for movement of liquids and gasses. Channels thus can connect other components, i.e., keep components "in communication" and more particularly, "in fluidic communication" and still more particularly, "in liquid communication." Such components include, but are not limited to, liquid-intake ports and gas vents. Microchannels are channels with dimensions less than 1 millimeter and greater than 1 micron. Some embodiments shown in the figures, by way of example, show two microchannels in a microfluidic device.

As used herein, the phrases "connected to," "coupled to," "in contact with" and "in communication with" refer to any form of interaction between two or more entities, including mechanical, electrical, magnetic, electromagnetic, fluidic, and thermal interaction. For example, in one embodiment, channels in a microfluidic device are in fluidic communication with cells and (optionally) a fluid reservoir. Two components may be coupled to each other even though they are not in direct contact with each other. For example, two components may be coupled to each other through an intermediate component (e.g. tubing or other conduit).

Other than in the operating examples, or where otherwise indicated, all numbers expressing quantities of ingredients or reaction conditions used herein should be understood as modified in all instances by the term "about." The term "about" when used to describe the present invention, in connection with percentages means ±5%.

As used herein, the term "substantially" is a relative term that can be used to indicate similar dimensions (e.g. height, width, etc.) or similar features (e.g. porosity, linearity, etc.) that need not be identical to a reference, e.g. preferably at least 80% of the dimension or feature, more typically, at least 90%, or at least 95%, or at least 97% or at least 99% or more.

BRIEF DESCRIPTION OF THE DRAWINGS

The patent application file contains at least one drawing executed in color. Copies of this patent or patent application publication with color drawing (s) will be provided by the office upon request and payment of the necessary fee.

(16) inserted. The chip (16) can be seeded with cells and then placed in a carrier (17) for insertion into the perfusion disposable.

Figure 2A:
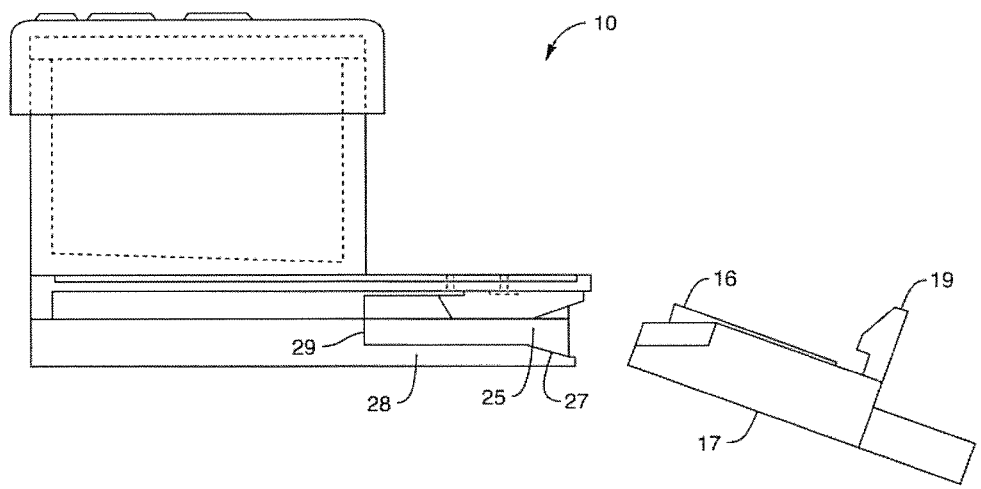

FIG. 2A shows a side view of one embodiment of a chip carrier (17) (with the chip inside) approaching (but not yet engaging) a side track (25) of a skirt of one embodiment of the perfusion manifold assembly (10), the carrier aligned at an angle matching an angled front end portion of the side track, angled slide (27) which provides a larger opening for easier initial positioning, followed by a linear or essentially linear portion (28), the carrier comprising a retention mechanism (19) configured as a upwardly protecting clip. Without being bound by theory, a suitably large angle permits chip engagement without smearing or premature engagement of liquid droplets present on the chip and/or the perfusion manifold assembly during the insertion and alignment processes.

Figure 2B:
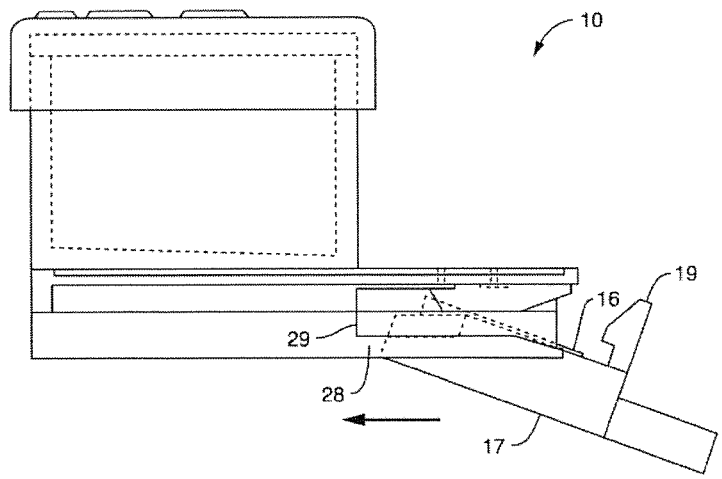

FIG. 2B shows a side view of one embodiment of a chip carrier (with the chip (16) inside) engaging a sidetrack of a skirt of one embodiment of (but not yet linked to) the perfusion manifold assembly.

Figure 2C:
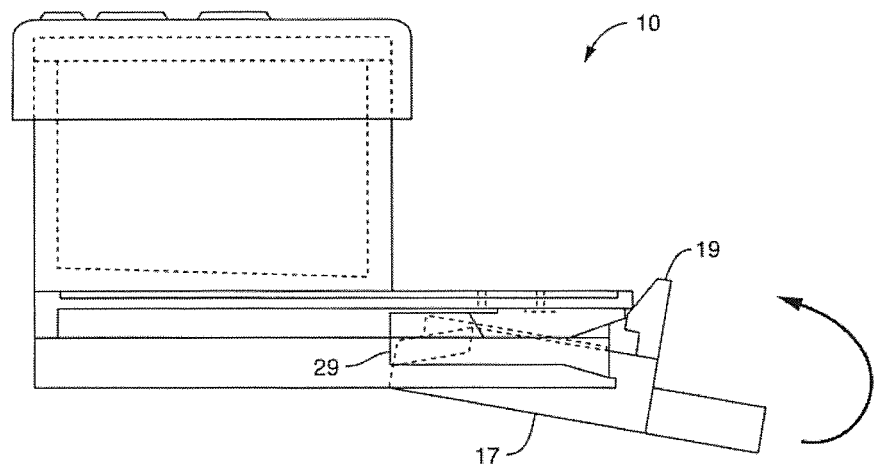

FIG. 2C shows a side view of one embodiment of a chip carrier (with the chip inside) fully engaging a side track of a skirt of one embodiment of (but not yet linked to) the perfusion manifold assembly (with an arrow showing the necessary direction of movement to get a snap fit whereby the retention mechanism will engage to prevent movement).

Figure 2D:
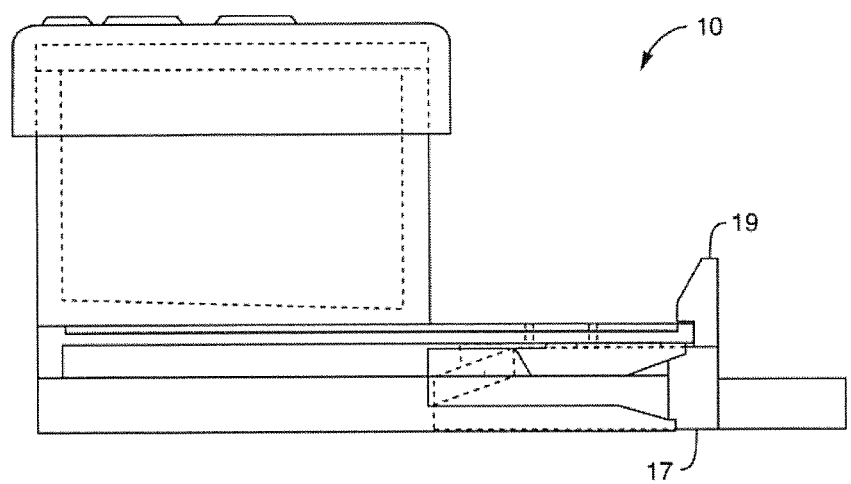

FIG. 2D shows a side view of one embodiment of a chip carrier (with the chip inside) detachably linked to the perfusion manifold assembly, where the retention mechanism is engaged to prevent movement.

Figure 3:
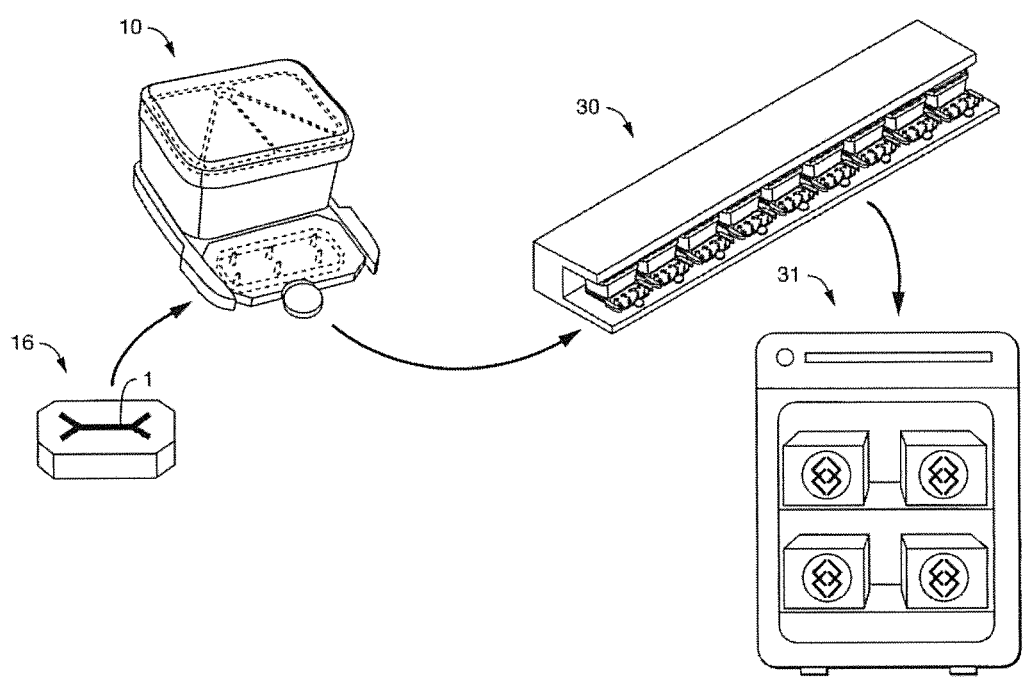

FIG. 3 is a schematic of one embodiment of a work-flow (with arrows showing each progressive step), where the chip (16) is linked (e.g. snapped in) to a disposable perfusion manifold assembly ("perfusion disposable") (10), which in turn is positioned with other assemblies on a culture module (30), which is placed in an incubator (31).

Figure 4:
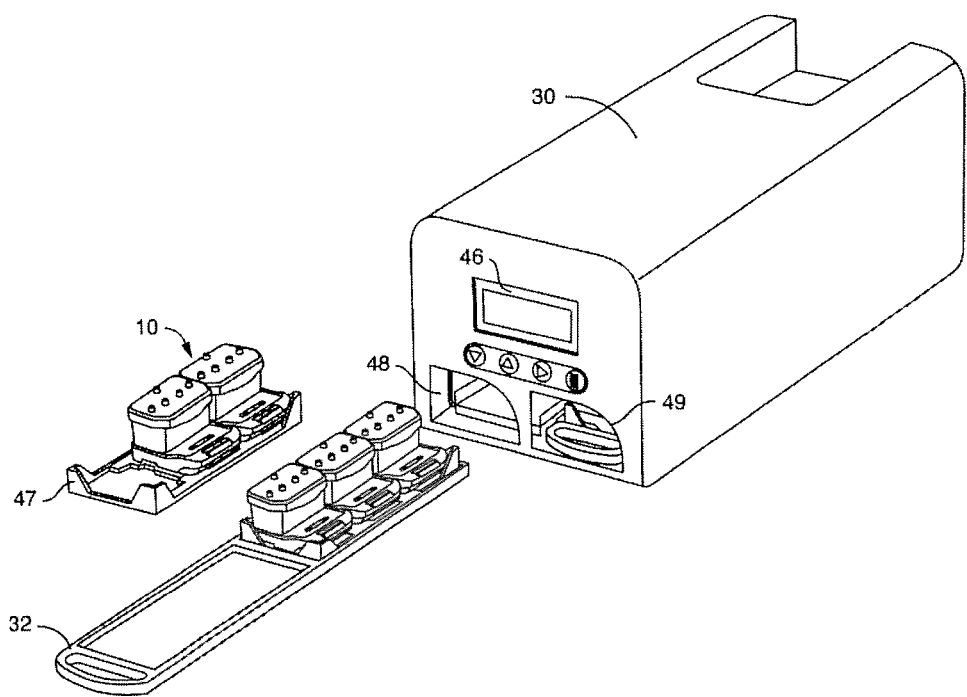

FIG. 4 is a schematic of another embodiment of the culture module (30) showing the tray (or rack) (32) and sub-tray (or nest) for transporting and inserting the perfusion disposables (10) into the culture module, which has two openings (48, 49) in the housing to receive the trays, and a user interface (46) to control the process of engaging the perfusion disposables and applying pressure. A typical incubator (not shown) can hold up to six modules (30).

Figure 5A:
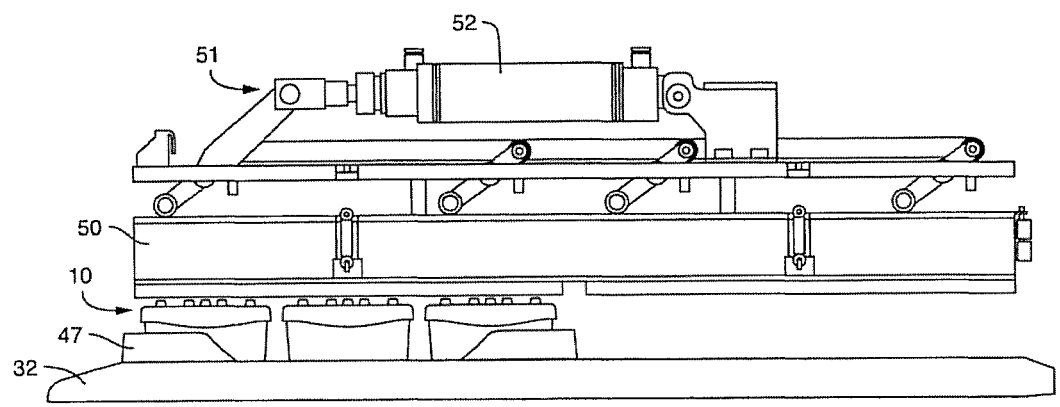

FIG. 5A is a schematic of the interior of one embodiment of the module (i.e. the housing has been removed), showing the pressure manifold (50) is in an open position, positioning of the tray (or rack) (32), sub-tray (or nest) (47), perfusion disposables (PDs) (10) under a pressure manifold (50) (but not engaging it, so the clearance is sufficient to remove them), with the actuation assembly (51) (including the pneumatic cylinder) (52) above. Three microfluidic devices or perfusion disposables are shown to illustrate, although more (e.g. 6, 9 or 12) are typically used at once.

Figure 5B:
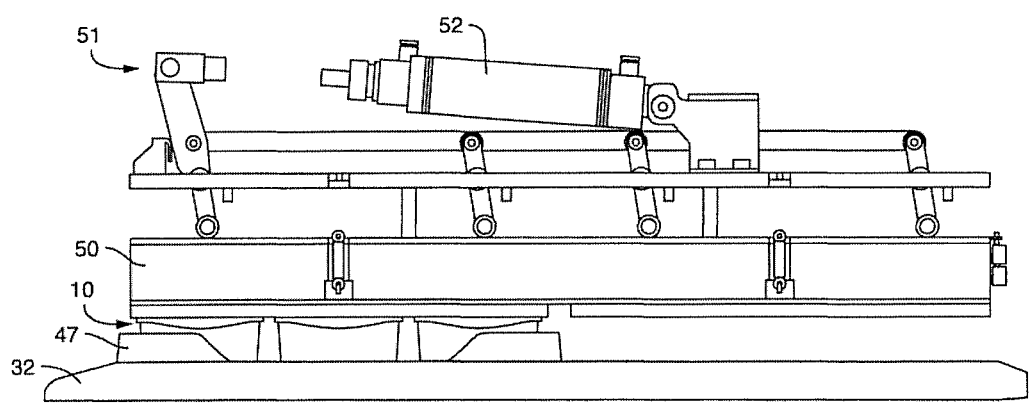

FIG. 5B is a schematic of the interior of one embodiment of the module (in an open position, i.e. the housing has been removed), showing the pressure manifold (50) in a closed position, with the positioning of the tray or rack (32), sub-tray or nest (47), perfusion disposables (10) under the pressure manifold (50) and engaging it, with the actuation assembly (51) including the pneumatic cylinder (52) above. The pressure manifold (50) simultaneously engages all of the perfusion disposables (10) while media perfusion is required or needed. Independent control of the flow rate in the top and bottom channels of the chip (16) can be achieved. The pressure manifold (50) can disengage (without complicated fluid disconnects) as desired to allow removal of the trays (32) or nests (47) for imaging or other tasks. In one embodiment, the pressure manifold (50) can simultaneously disengage from a plurality of perfusion manifold assemblies. In one embodiment, the perfusion disposables (10) are not rigidly fixed inside the nests (47), allowing them to locate relative to the pressure manifold (50) as it closes. In a preferred embodiment, integrated alignment features in the pressure manifold (50) provide guidance for each perfusion disposable (10). Again, three microfluidic devices or perfusion disposables are shown to illustrate, although more (e.g. 6, 9 or 12) are typically used at once.

Figure 6A:
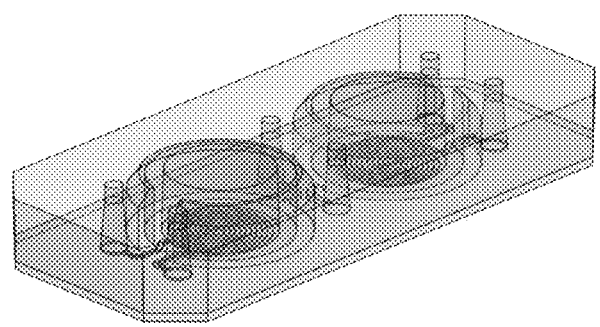

FIG. 6A illustrates a perspective view of one embodiment of a microfluidic device with enclosed microfluidic channels as a CAD (computer-aided design) image.

Figure 6B:
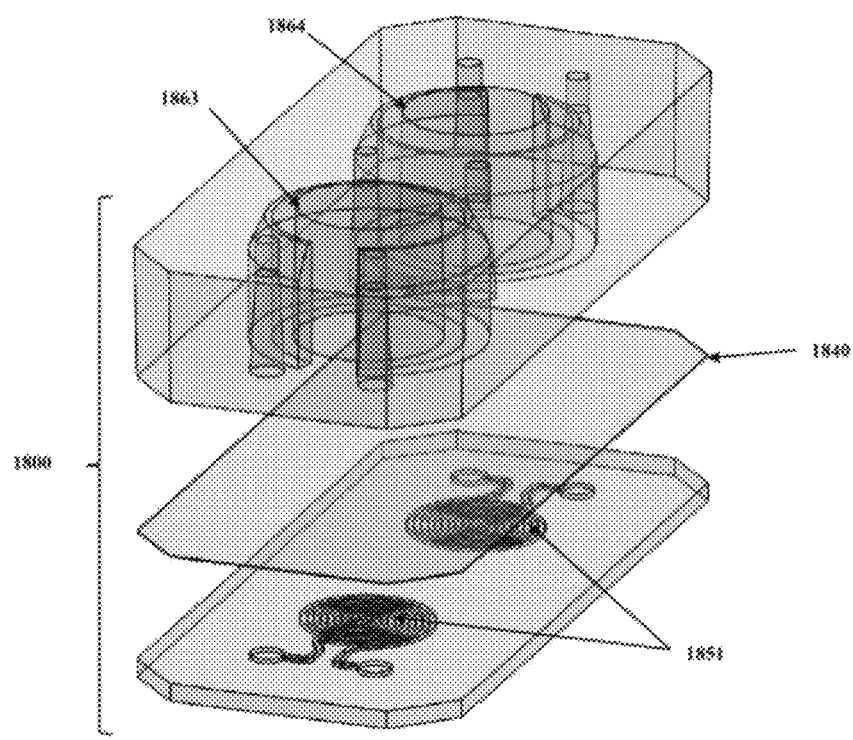

FIG. 6B illustrates an exploded view of one embodiment of a microfluidic device 1800 (showing a first chamber 1863 microfluidic channel in a top piece and a second chamber 1864 microfluidic channel in a bottom piece, separated by a membrane 1840) and the at least two spiral microchannels 1851.

Figure 7A:
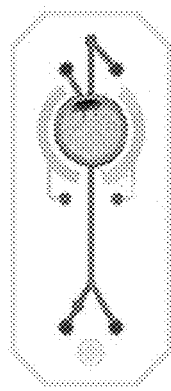
Figure 7C:
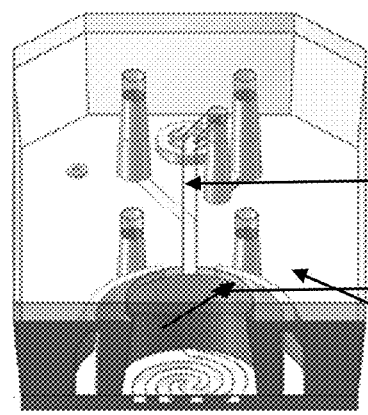
Figure 7B:
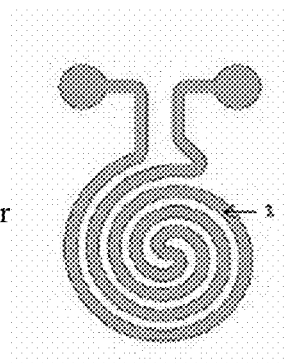
Figure 7D:
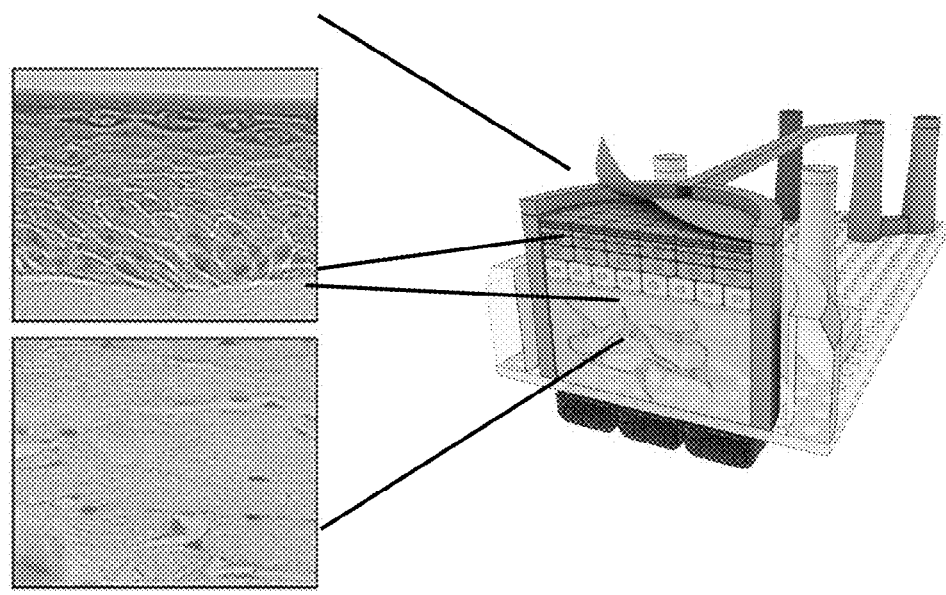

FIG. 7A-D shows schematic drawings and exemplary micrographs of cell growing in an exemplary open top chip. In one embodiment, a skin on-chip is an exemplary open top chip. FIG. 7A shows a schematic of one embodiment of an open top chip. FIG. 7B shows a side view schematic as a cross section of one embodiment of an open top chip. FIG. 7C shows a schematic of one embodiment of a lower circular channel simulating a blood vessel located in the bottom of the chip. FIG. 7D shows a schematic of one embodiment of an open top chip comprising a keratinocyte layer in the top fluidic channel (micrograph of keratinocyte layer on the upper left) and a lower dermal area underneath (micrograph of growing cells in the dermal area (layer) on the lower left).

Figure 8A:
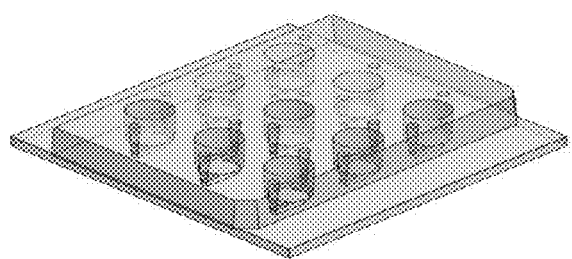
Figure 8B:
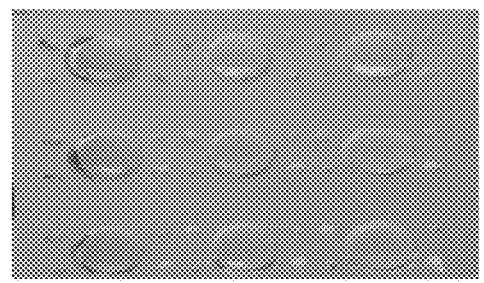
Figure 8C:
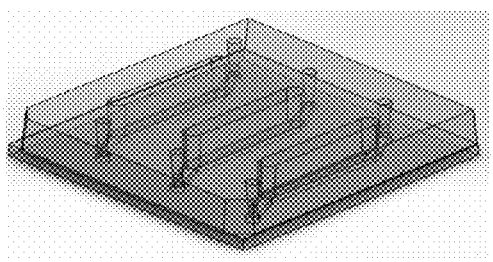
Figure 8D:
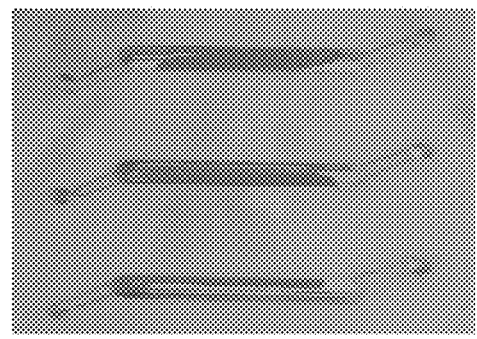

FIG. 8A-D shows exemplary schematic illustrations of additional types of chips (i.e. geometries) that may be used with fluids comprising fluid modifying reagents. FIG. 8A shows an exemplary schematic illustration of a circular format (geometry) for a microfluidic chip. FIG. 8B shows exemplary photographs of a side view (upper) and top view (lower) circular chip. FIG. 8C shows an exemplary schematic illustration of a rectangular format (geometry) for a microfluidic chip. FIG. 8D shows exemplary photograph of a top view of a rectangular chip.

Figure 9A:
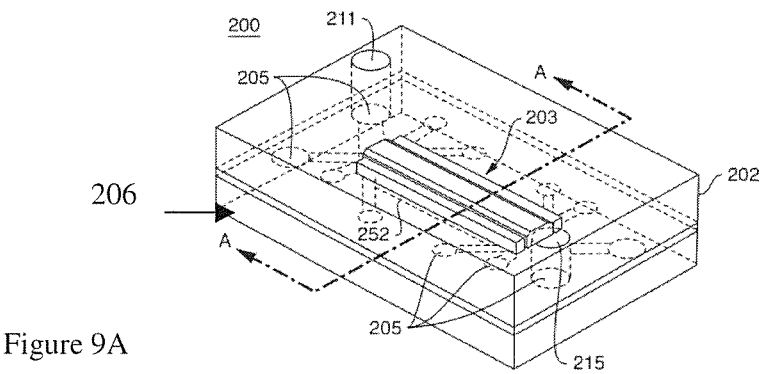
Figure 9B:
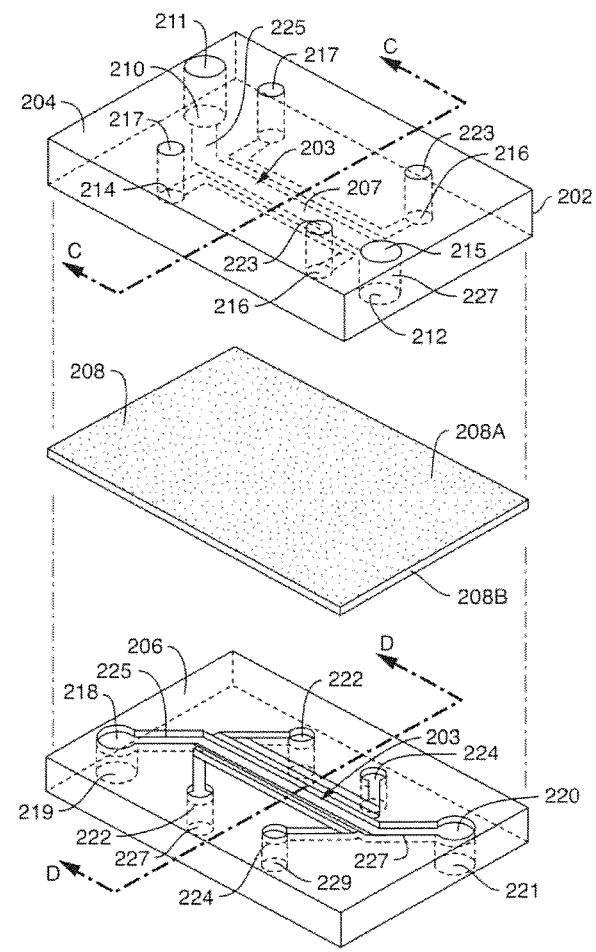

FIG. 9A-B illustrates a perspective view of the tissue interface device in accordance with an embodiment. In particular, as shown in FIG. 9A, the device or chip 200 preferably includes a body 202 having a branched microchannel design 203, showing input and output ports (211; 215), including a plurality of ports 205; in fluidic communication with an active region or experimental region (A) a tissue-tissue interface simulation region (membrane 208 in FIG. 9B) of microchannels (203) with optional vacuum chambers (252) in accordance with an embodiment.

FIG. 9B illustrates an exploded view of the microfluidic device of FIG. 9A. See further information on device numbers described herein.

FIGS. 10A-G illustrates contemplated embodiments of Airway-on-Chip fluidic devices for use with fluid modifying agents. As shown here, exemplary embodiments of human primary airway cells are cultured in a microfluidic Airway-on-Chip. FIG. 10A is a schematic representation of one embodiment of an Airway-on-Chip where cells seeded in the upper channel and grown with an air interface (blue), on top of a lower channel under media flow (red). FIG. 10B shows a colored scanning electron micrograph of ciliated cells, where cilia are artificially colored blue with non-ciliated cells artificially colored brown. FIG. 10C shows a still shot (video frame) of cilia beating (blurry cilia). FIG. 10D shows an immunofluorescent micrograph of Goblet cells (red stained mucine proteins with blue colored nuclei). FIG. 10E shows a still shot from a video micrograph of mucociliary transport (i.e. mucociliary escalator) where the white dots are fluorescent microbeads moving across the upper surface of the epithelium. FIG. 10F illustrates a perspective view of one embodiment of a cross section through the Airway Chip microfluidic device with showing its two hollow linear channels (air channel above; blood channel below) separated by a porous membrane which supports growth and differentiation of human primary airway epithelial cells on its upper surface and human pulmonary microvascular endothelial cells underneath (FIG. 10G).

Figure 11A:
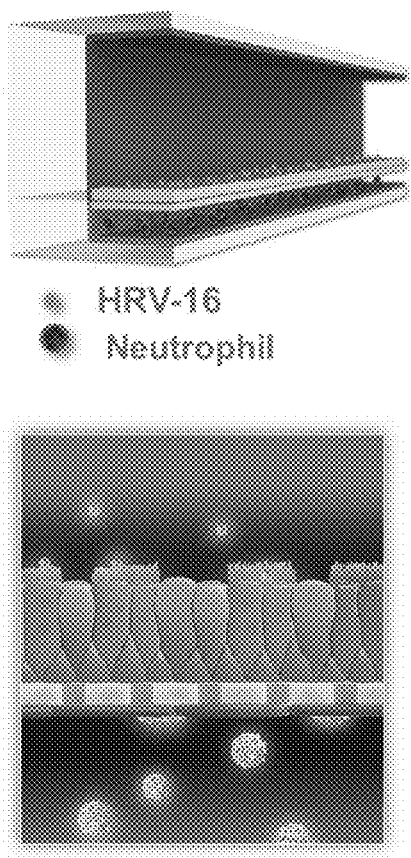
Figure 11B:
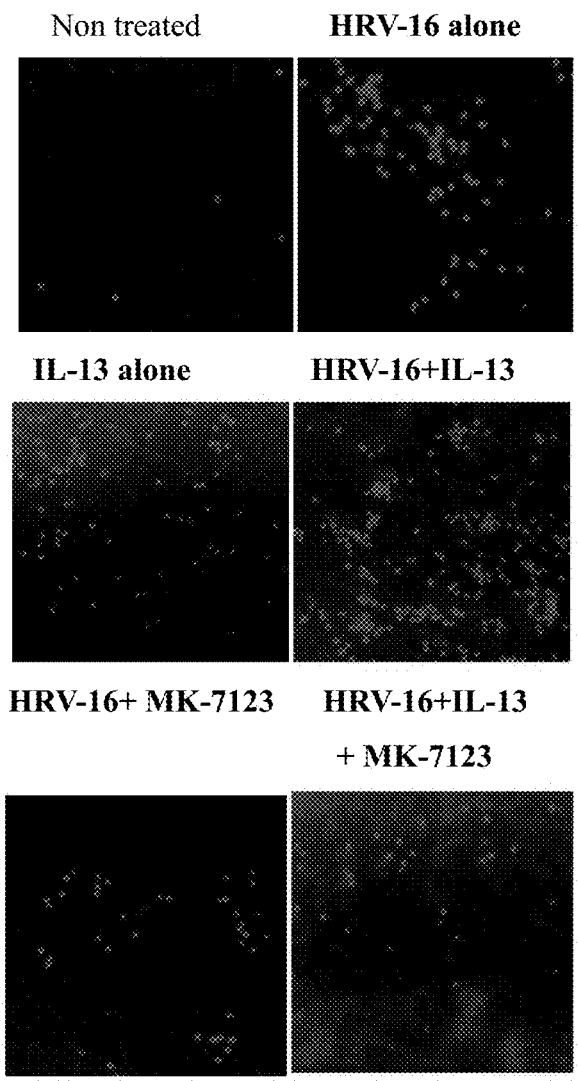
Figure 11C:
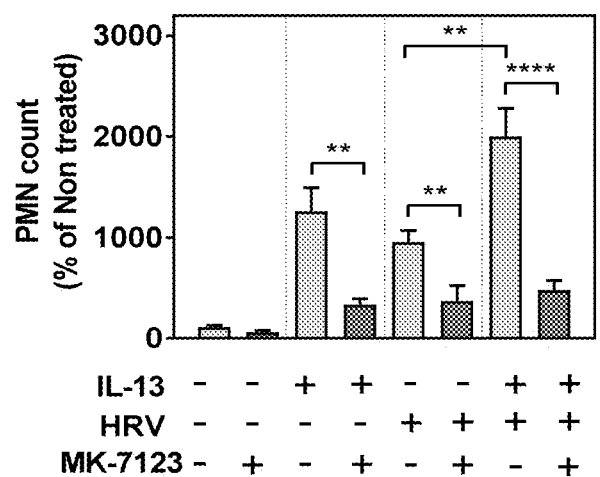

FIGS. 11A-C demonstrates contemplated embodiments of inflamed Airway-on-Chip fluidic devices with fluid modifying agents for use in immune recruitment assays. As shown here, exemplary embodiments of an inflamed Airway-on-Chip emulating acute asthma exacerbation by combining Rhinovirus infection with IL-13 stimulation in the presence of an exemplary immuno-modulatory compound. In some embodiments, neutrophil recruitment following exacerbation with HRV can be reduced by an exemplary CXCR2 antagonist MK-7123, however these experiments were done by flipping chips. FIG. 11A (upper image) shows one embodiment of an Airway-on-Chip that enables testing of immuno-modulatory compounds, e.g. for neutrophil recruitment, in a model of acute asthma exacerbation. HRV-16 is represented as small green dots in the upper channel while neutrophil cells (also described as polymorphonuclear leukocytes (PMN)) are represented as large purple spots in the lower channel. An enlarged schematic is demonstrated schematically in the lower image showing a HRV-infected Airway Chip during perfusion in the vascular channel of freshly isolated human neutrophil. FIG. 11B shows a series of fluorescent micrographs showing comparisons of stained neutrophil cells (red) recruited to the endothelium and attached to non-treated cells. Treatments included HRV-16 alone infected cells, IL-13 alone treated cells, HRV-16 and (+) IL-13 treated cells, HRV-16+CXCR2in (inhibitor) treated cells, and HRV-16+IL-13+CXCR2in. Non-stimulated chips are showing limited neutrophil recruitment while HRV infected and IL-13-treated chips show increased neutrophil recruitment. IL-13+HRV induce an additive increase in neutrophil recruitment, while treatment with a CXCR2 antagonist. MK-7123 (10 microM) significantly reduced neutrophil recruitment under three stimulation conditions. FIG. 11C is a graphical comparison showing PMN (neutrophil) cells counts as % of untreated cells and cells treated with combinations shown for IL-13, HRV, and CXCR2 (in) treatments. Quantification of neutrophil recruitment (p<0.01; **p<0.001).

Figure 11D:
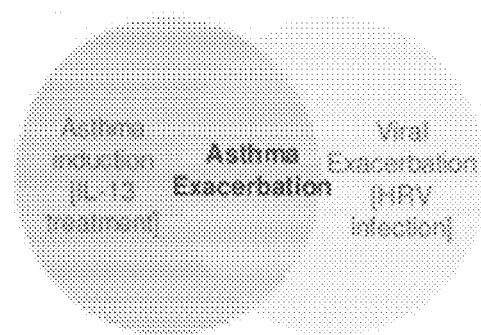
Figure 11E:
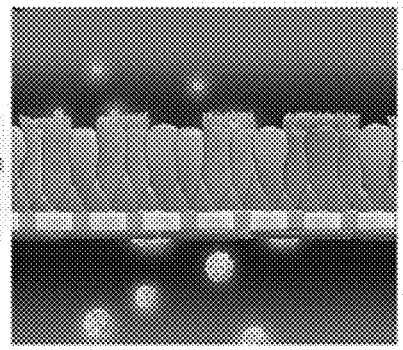
Figure 11F:
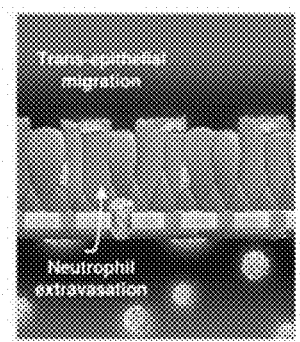
Figure 11G:
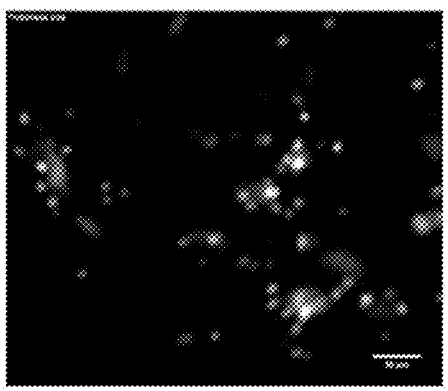
Figure 11H:
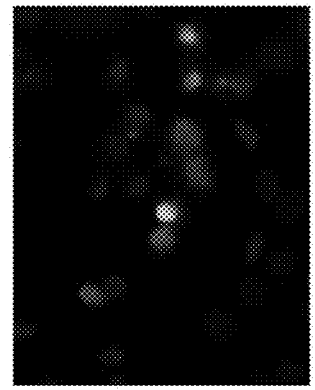
Figure 11I:
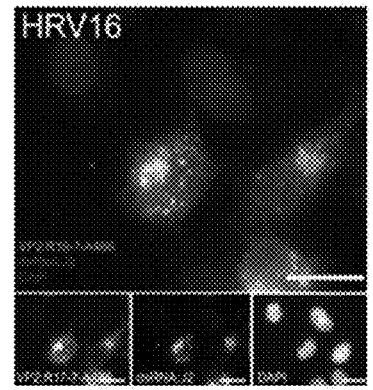

FIGS. 11D-I show exemplary schematics and data, showing viral-induced exacerbation on-chip inducing neutrophil transmigration, for use in on-chip testing of prophylactic treatments for reducing incidents of severe asthma attacks and for treatments during severe asthma attacks to reduce at least one symptom. FIG. 11D shows an exemplary schematic (as a Venn Diagram) where asthma induction as an inflamed airway is represented by IL-13 treatment (left circle) and viral exacerbation of asthma is represented by a rhinovirus (HRV) infection (right circle). The area of overlap represents asthma exacerbation in a patient or on-chip when both conditions are present. FIG. 11E shows an exemplary schematic of one embodiment of asthma exacerbation where a virus is infecting ciliated epithelial cells in the airway channel (green dots and green ciliated cells) which induces neutrophil (bumpy round cells) recruitment (attachment) and movement through the endothelium on the vascular channel, then as shown in FIG. 11F, neutrophils show extravasation through the porous membrane then into the airway side of the membrane, i.e. trans-epithelial migration. FIG. 11G shows one embodiment of a severe asthma chip enabling neutrophil diapedesis: HRV16 (24 hpi) infected cells visualized by immunofluorescent staining of Myeloperoxidase (MPO) stained neutrophils showing a Z-stack confocal microscopic image. FIG. 11H shows a colorized immunofluorescent image of HRV16 (24 hpi) infected cells stained with Myeloperoxidase (MPO) (green)/ mAbJ2 (red)/DAPI (blue) where MPO+ cells are located near virally infected cells. And FIG. 11I shows a monoclonal antibody (mabJ2) (mouse) detecting double-strand RNA as an RNA replication-center assay for one embodiment of a high content image-based quantification of human rhinovirus and Coxsackie virus infections.

Figure 12D:
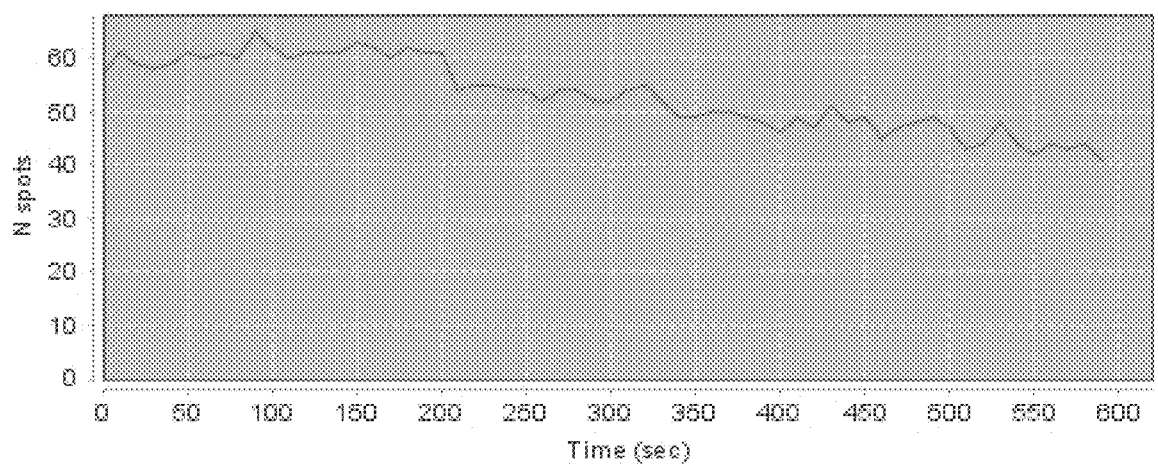

FIGS. 12A-D shows an example of an assay contemplated for measuring immune cell recruitment, neutrophil crawling (diapedesis) and transmigration of cells out of the endothelial channel, in fluidic devices comprising a fluid modifying agent. In one embodiment, an Airway-on-Chip infected with HRV, with and without a CXCR2 antagonist (inhibitor of neutrophil cell recruitment) demonstrating the effect of a CXCR2 antagonist on neutrophil crawling and transmigration of cells out of the endothelial channel in a device without a fluid modifying agent, where chip inversion was used for allowing neutrophil attachment. FIG. 12A is a micrograph showing effects of HRV-16 infected cells (24 hpi) on cell attachment and FIG. 13B shows effects of HRV-16 infected cells (24 hpi) treated with CXCR2 in (10 µM) on cell attachment. FIG. 12C shows a graph of the number of spots (i.e. neutrophil cells: N spots) counted over time (up to 300 seconds) for HRV-16 infected cells (24 hpi). FIG. 12D shows a graph of N spots counted over time (up to 600 seconds) for HRV-16 infected cells (24 hpi) treated with CXCR2in (10 µM).

FIGS. 13A-D shows exemplary embodiments for linking together microfluidic chips contemplated for use with fluids comprising reagents.

Figure 13A:
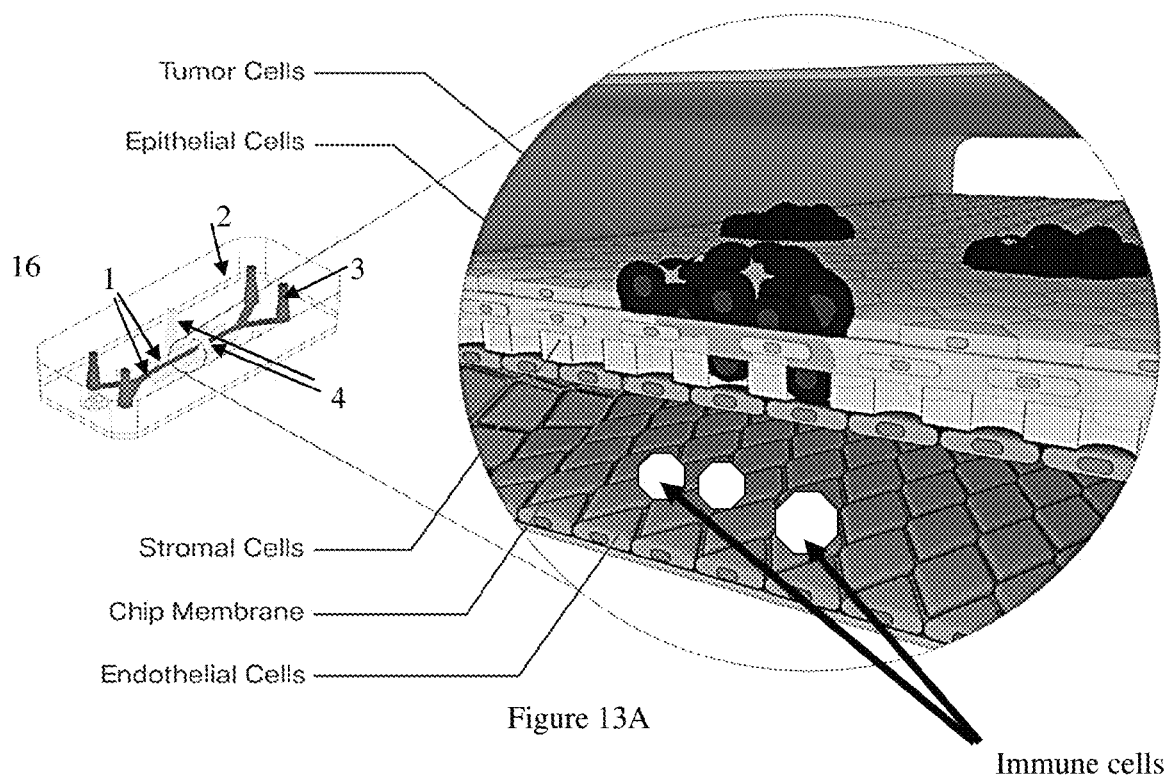
Figure 13B:
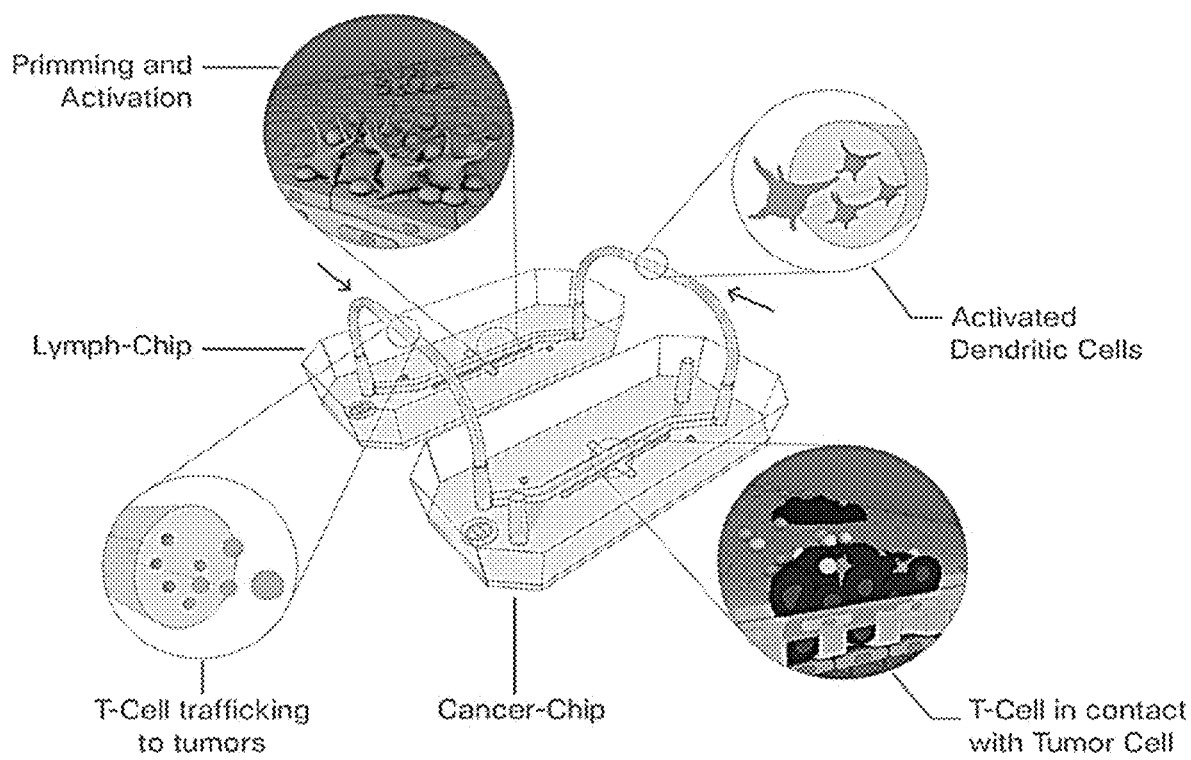

FIG. 13A shows an exemplary schematic illustration of one embodiment for providing a Tumor-On-Chip (Tumor On-Chip or Cancer On-Chip) and one embodiment for incorporation of a tumor microenvironment. On the left, a schematic illustration shows one embodiment of a microfluidic Tumor-On-Chip (16), having two microfluidic channels (1), with an upper channel port (2) and lower channel port (3), with optionally used vacuum chambers (4). On the right, a schematic illustration shows one embodiment of a microfluidic Tumor-On-Chip with four cell types, in the upper channel, tumor cells and epithelial cells on top of a stromal cell layer separated by a chip membrane from the lower channel with endothelial cells. Immune cells (white) are added to chips in the lower vascular channel (shown) and/or immune cells are added to the upper channel.

FIG. 13B shows an exemplary schematic illustration of one embodiment for providing a Cancer-Chip (Cancer-On-Chip) linked to a Bone-Marrow Chip.

Figure 13C:
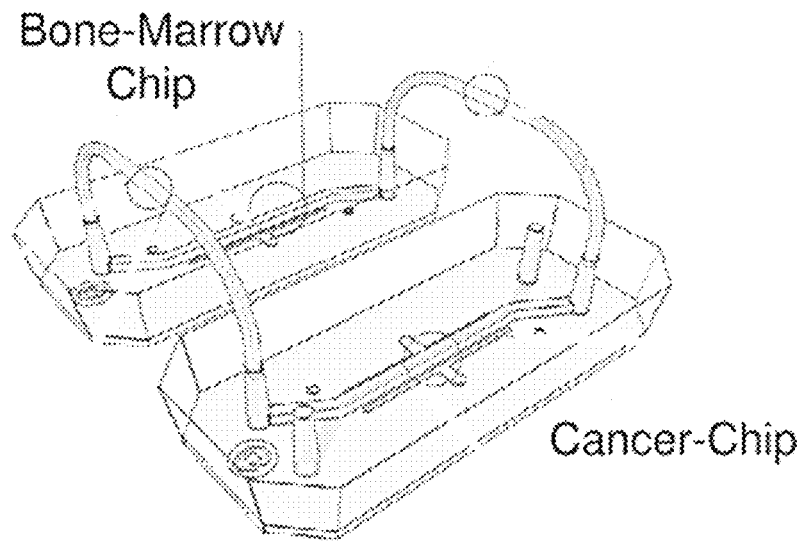

FIG. 13C shows an exemplary schematic illustration of a Cancer-Chip (Cancer-On-Chip) linked to a Lymph Chip (Lymph Node-on-chip).

Figure 13D:
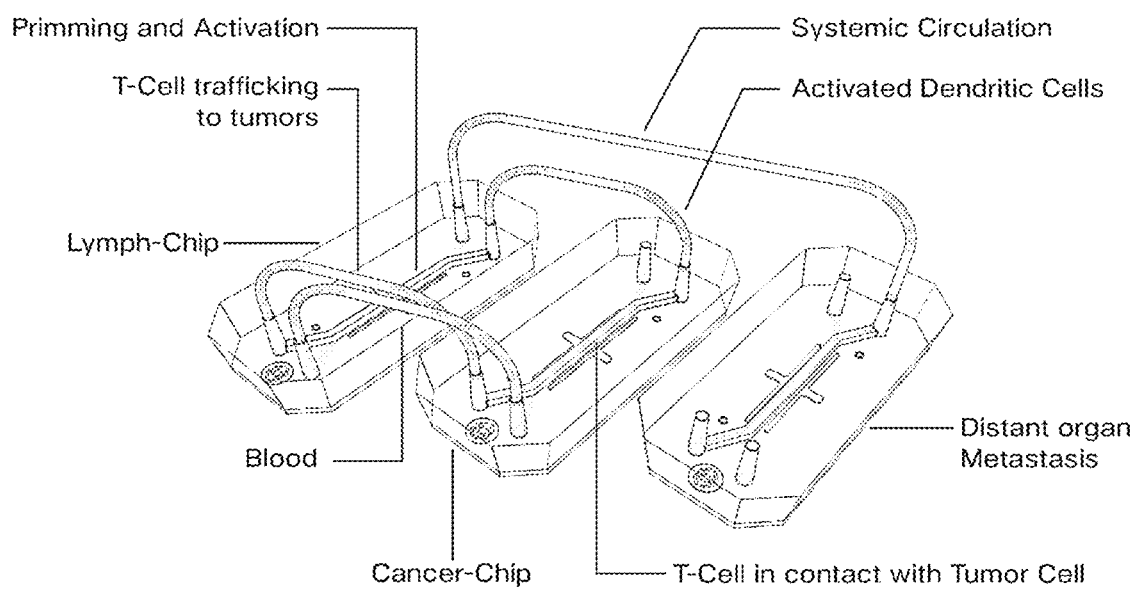

FIG. 13D shows an exemplary schematic illustration for providing a Metastasis-Chip (System) for one embodiment, a Cancer-Chip (Cancer-On-Chip) linked to a Lymph Chip (Lymph Node-on-chip) with at least one additional Organ-chip fluidically attached to the Lymph Chip. In one embodiment, there is an incorporation of a vascular component the Lymph Chip.

Figure 14:
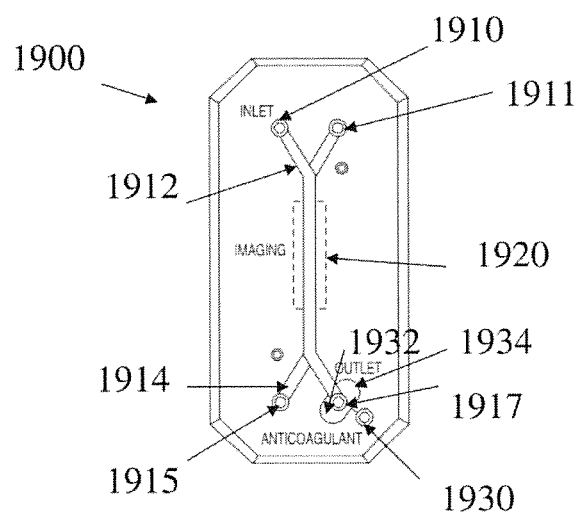

FIG. 14 demonstrates one contemplated embodiment of fluidic device or chip (1900) having an anticoagulant ports (1932 and 1934) for use with a fluid-modifying agent, such as a blood substitute. Shown is a schematic of one embodiment of a microfluidic device, as in FIG. 9A, with the addition of an anticoagulant ports as additive channels (1932 and 1934 surrounding the OUTLET port 1917) (one on either side near at least one inlet or outlet port for which effluent anti-coagulation is desired). Arrows pointing to INLET ports 1910 and 1911 for upper and lower channels while other arrows point to OUTLET ports 1917 and 1915, respectively attached to inlet ports. The upper channel 1912 emerges from one INLET 1910. The lower channel 1914 emerges from underneath the upper channel attached to the lower Inlet 1911. Each of two microchannels terminates at a single port. Each microchannel attached to an anticoagulant port is in fluidic communication with two additive channels, each pair of additive channel connecting to a separate port (e.g. for adding the additive to the additive channel, i.e. ANTICOAGULANT port 1930). attached to the top microfluidic channel where the upper channel is also marked with an OUTLET at one end. In other embodiments, the lower vascular chamber has an anticoagulant port near the vascular outlet. An arrow points to the IMAGING area (active region) 1920 outlined with dotted lines.

Figure 15:
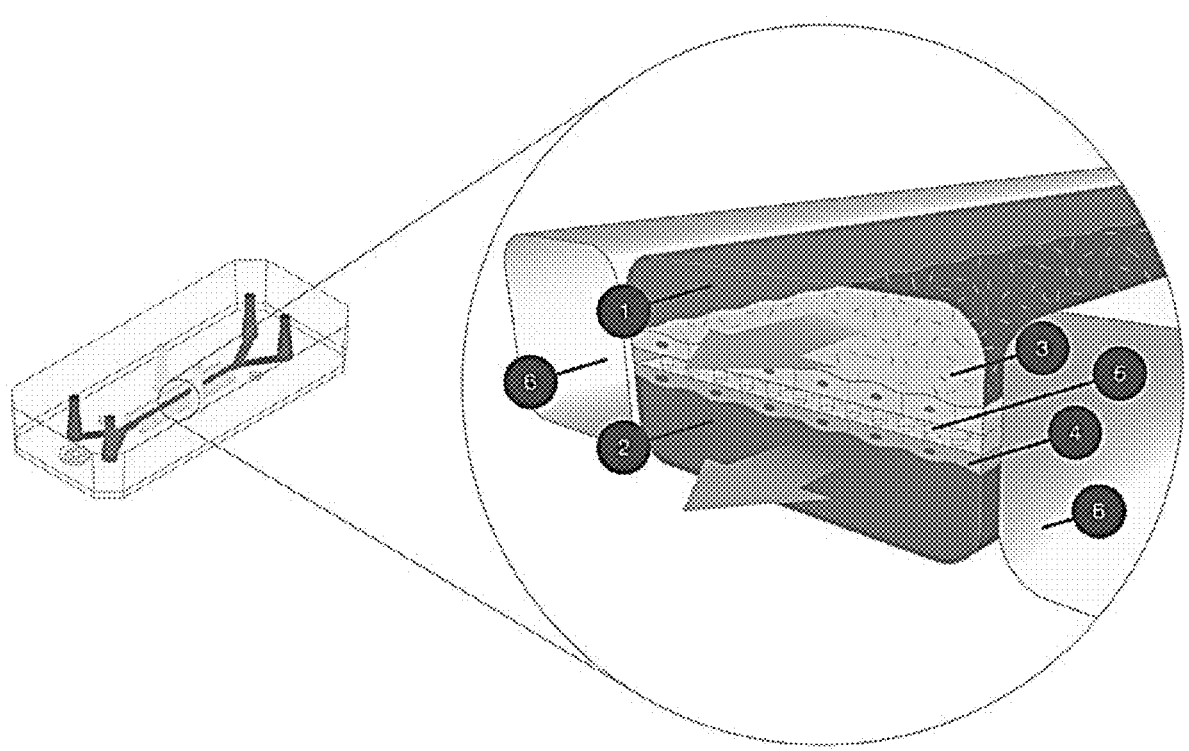

FIG. 15 demonstrates one contemplated embodiment of fluidic device for use with a fluid-modifying agent, showing an exemplary schematic representation of an Intestine On-Chip: 1. Epithelial Channel; 2. Vascular Channel; 3. Human Primary Intestinal Epithelial Cells; 4. Human Intestinal Microvascular Endothelial Cells (HIMEC) or iHIMEC, etc.); 5. Membrane; and 6. Vacuum Channels.

Figure 16:
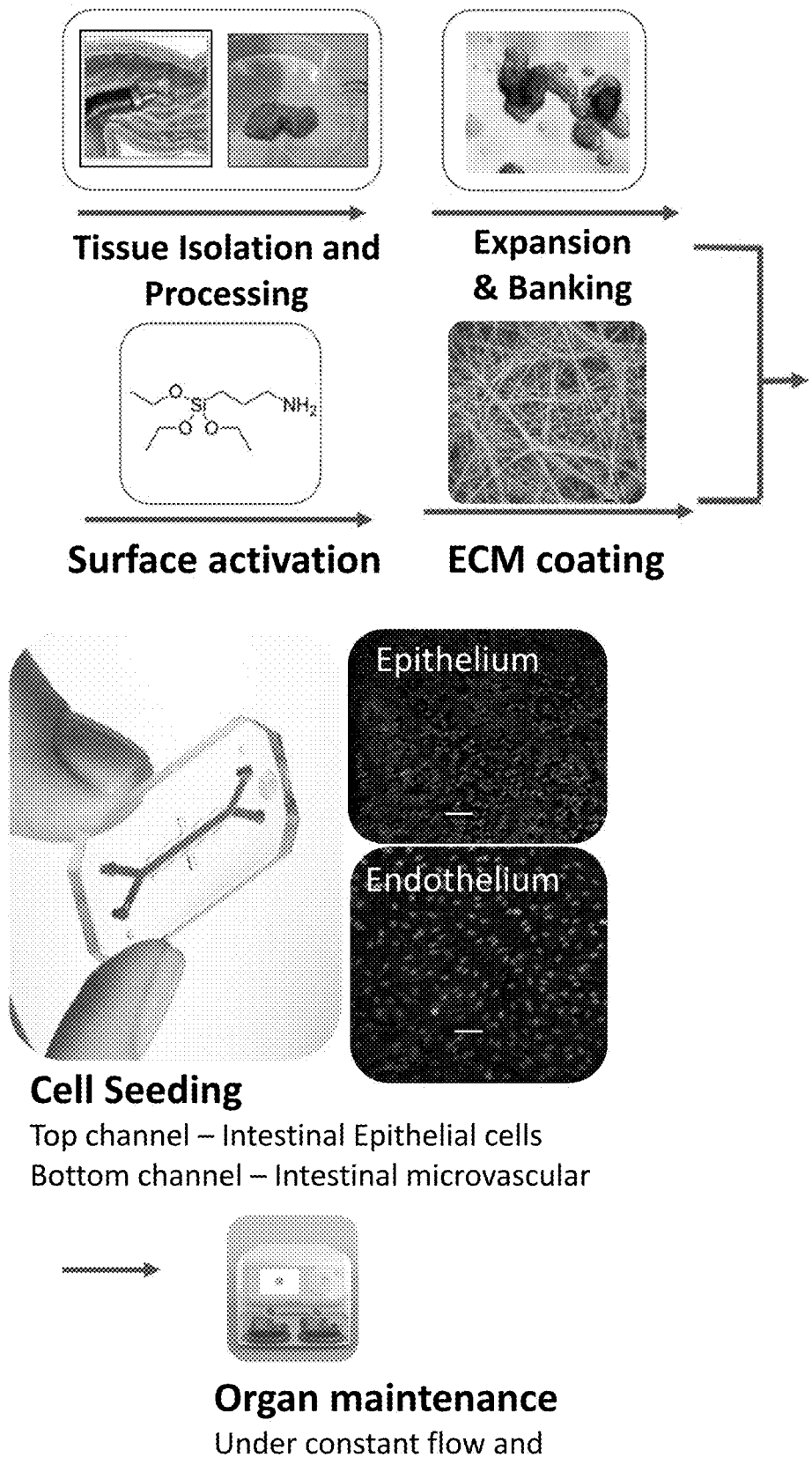

FIG. 16 shows an exemplary schematic representation along with representative photographs and micrographs for preparing one embodiment of a fluidic Intestine-on-Chip for use with a fluid-modifying agent where methods of (left to right) tissue isolation and processing; expansion & banking provide cells used to seed: Top channel—Intestinal epithelial cells forming an epithelium and Bottom channel—Intestinal microvascular endothelium (HIMEC) incubated (organ maintenance) under constant flow and certain membrane stretch conditions. Prior to cell seeding, the chip membrane was surface activated then ECM coated. Lower images show morphology by phase contrast microscopy of the epithelial cell layer exposed to flow over time (left 3 images) compared to the same time period, 12 days of incubation, under static culture (right image). Thus, in this co-culture setup we observed the spontaneous 3D villa formation that doesn't occur in the static culture. We have successfully maintained this microfluidic co-cultures for over 3 wk with no loss of phenotype.

Figure 17A:
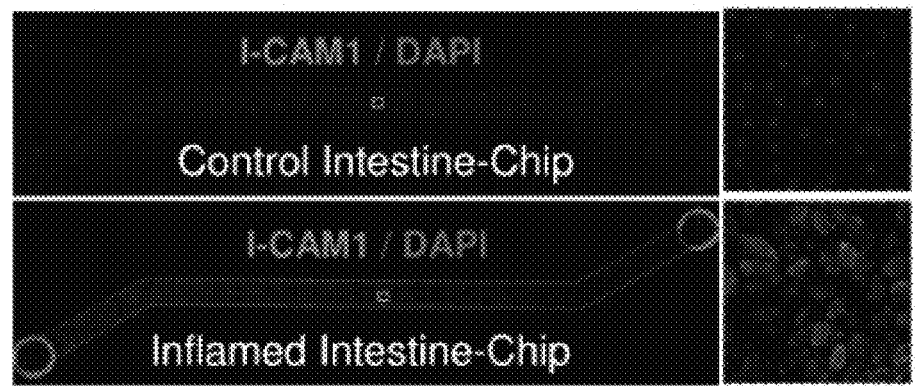
Figure 17B:
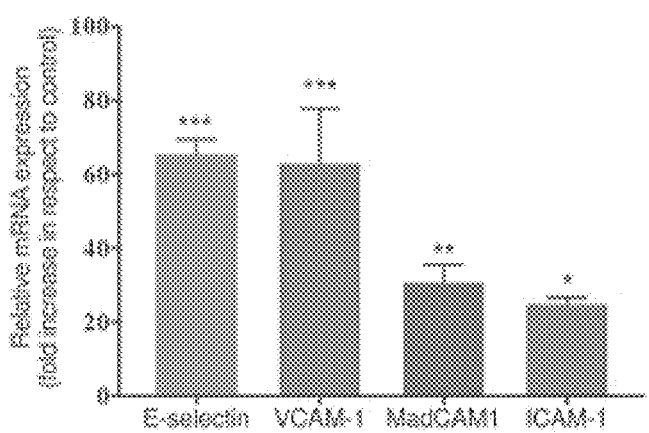

FIG. 17A-B shows exemplary florescent microscope images and graphs demonstrating induction of adhesion molecule expression in intestinal endothelial cells on-chip 24 hours after induction of inflammation using clinically relevant levels of cytokines. FIG. 17A shows images of induced ICAM-1 (pink) and nuclei (blue) stained channels (left) and under higher magnification (right) for control (upper) and inflamed (lower) channels. FIG. 17B shows a graphical comparison of relative mRNA expression for E-selectin, VCAM1, MadCAM1 and ICAM-1. Cells on-chip were treated for 24 hours with a Cytomix Formulation (e.g. Miltenyi Biotec, Cambridge, Mass., USA): TNF-alpha 10 U/ml (approximately 215 pg/ml), IL-1β 50 U/ml (approximately 50 pg/ml), IL-6 20 U/ml (approximately 200 pg/ml). U=units.

Figure 18A:
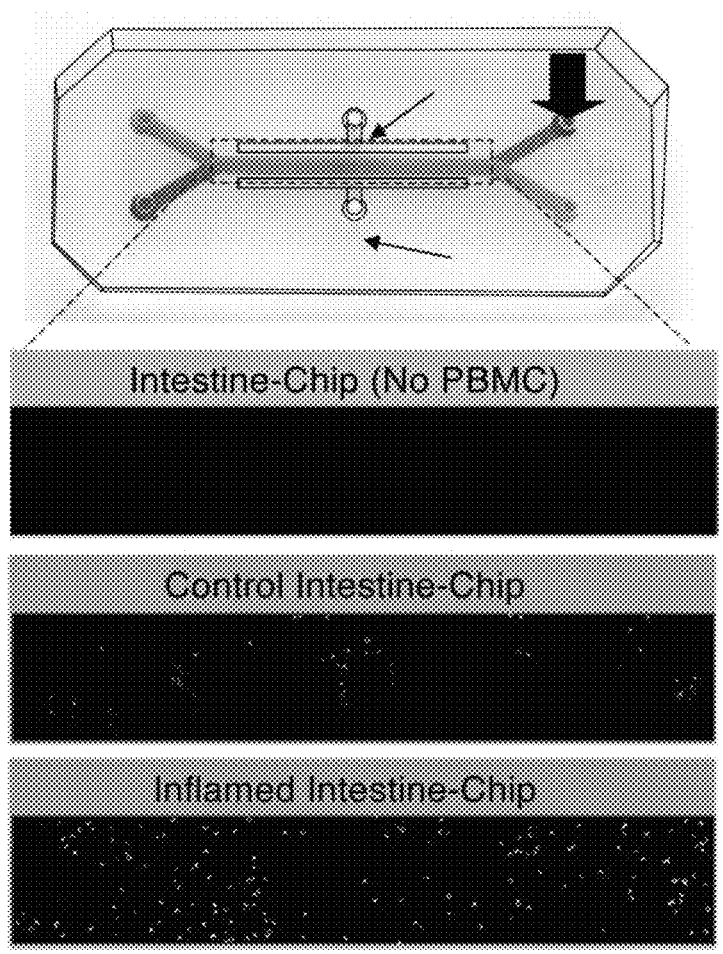
Figure 18B:
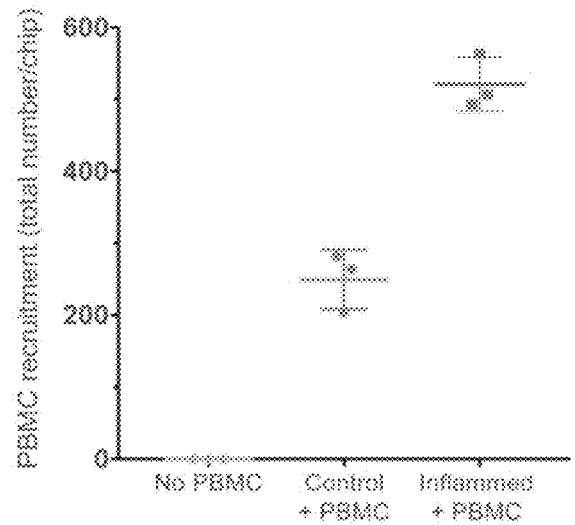

FIG. 18A-B shows exemplary increased PBMC recruitment after cytokines-induce inflammation of the endothelium of an inflamed intestine-Chip. FIG. 18A shows a larger arrow where PBMCs may be added to flow into the main vascular channel. Alternatively, small arrows point to ports where PBMCs may be added to the center area of the channel. Images on the right show white dots representing PBMCs attached to the endothelial layer for no PBMCs added to a chip that was not treated by cytokines, center control with PBMCs but no cytokine treatment and right panel where an inflamed endothelium has numerous attached PBMCs. Attached PBMCs are shown numerically as a total number/chip in an exemplary graph in FIG. 18B.

Figure 19I:
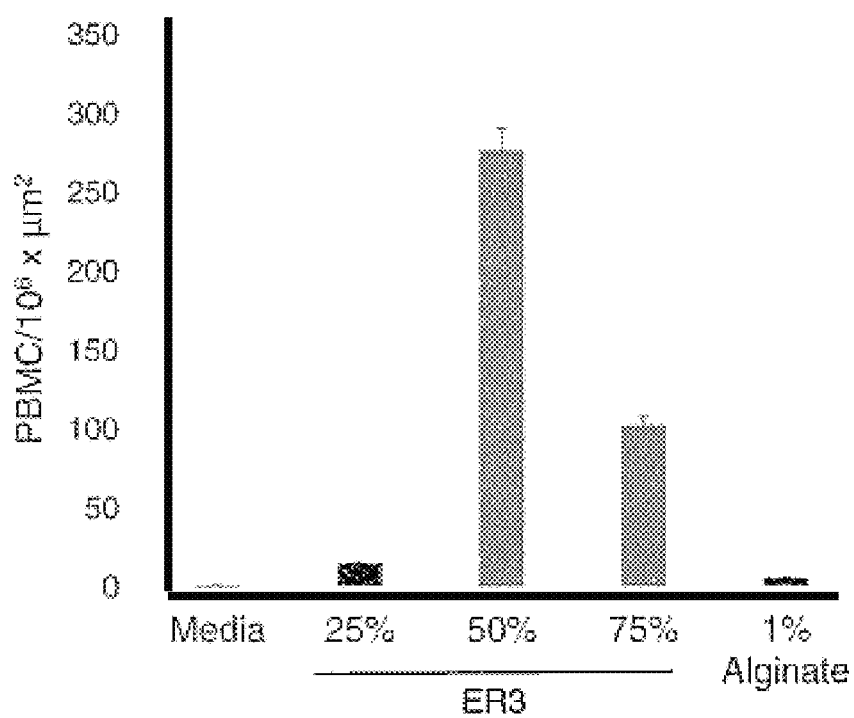
Figure 25:
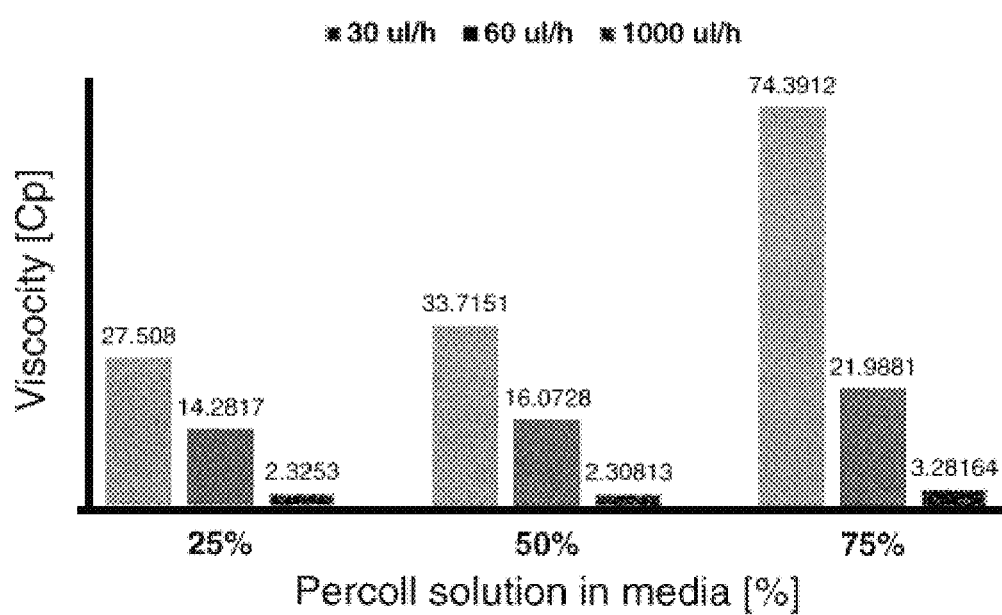

FIG. 19A-I shows an exemplary demonstration that increased media viscosity improves immune cell recruitment to the endothelial layer by improving the interaction of immune cells with endothelium. Exemplary florescent microscope images, focused on the endothelial plane, showing green labeled PBMC (peripheral mononuclear blood cells) (each green dot or white dot represents one cell) attached to inflamed endothelium, under liquid flow where the liquid contained FIG. 19A 0% Percoll; FIGS. 19B and 19E 25% Percoll; FIGS. 19C and 19F 50% Percoll; FIG. 19D 80% Percoll; FIG. 19G 75% Percoll, and FIG. 19H 1% Alginate but no Percoll. Addition of Percoll increases media viscosity and improves immune cell—endothelium interaction. At 50% Percoll there is clear cell attachment and 50% Percoll showed the highest immune cells recruitment to inflamed endothelium, FIGS. 19C and 19F. Increased media viscosity is achieved by addition of Percoll that consists of colloidal silica particles of 15-30 nm diameter coated with polyvinylpyrrolidone (PVP). FIG. 19I shows graphically that the addition of 50% Percoll allows a higher number of PBMCs to attach as compared to the results obtained using 25% and 75% Percoll. While not intending to limit the invention to any particular mechanism, it is believed that the increase in shear by the addition of Percoll allows increased numbers of immune cells to interact with endothelial cells.

FIG. 20A-C shows embodiments of an intestine on chip emulating Immune Cell Recruitment on-Chip through providing physiological level of shear and fluid viscosity to emulate immune cell recruitment at epithelial-endothelial tissue interfaces. Embodiments of intestine on chip showing a florescent micrograph of stained cells FIG. 20A under non-physiological shear in vascular channel and non physiological fluid viscosity. FIG. 20B under physiological shear in vascular channel and physiological fluid viscosity. PBMCs (green) and inflamed HIMEC (red). FIG. 20C shows flow directions (arrows) on a chip schematic and the acquisition area and level where images were taken. Scale bar=100 micrometers. Physiological levels of shear and fluid viscosity emulate immune cell recruitment at the epithelial-endothelial (tissue-tissue) interface.-FIG. 20D-E shows one embodiment of an intestine on chip where flowing media without the addition of Percoll does not induce PBMC attachment at the same level of imaging as in FIG. 20C.

Figure 21A:
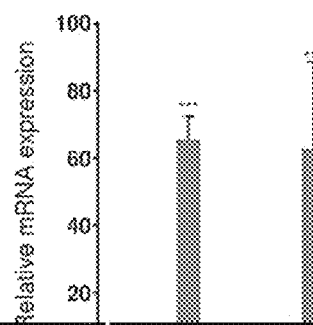

FIG. 21A chart showing relative mRNA expression between standard media (left, grey bars), viscous media (50% Percoll) (blue, middle bars) and inflammatory inducing media containing Cytomix cytokines (right, pink bars), after 24 hours of treatment.

Figure 21B:
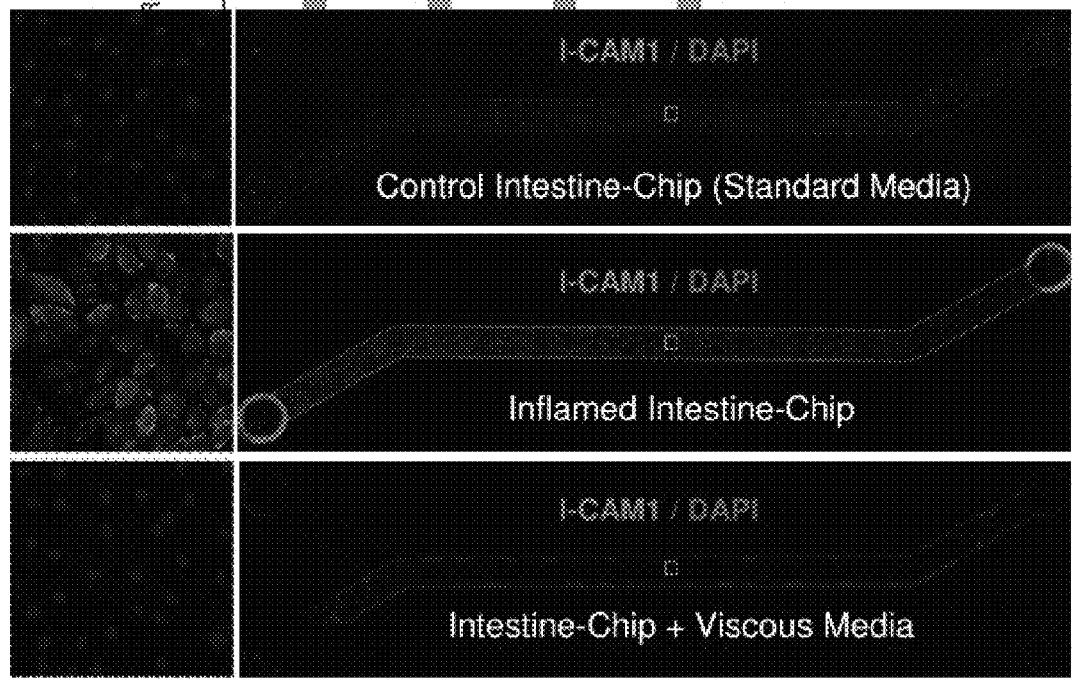

FIG. 21A-B shows that a change in the media viscosity does not affect the expression of adhesion molecules on endothelial cells (vascular compartment) on-chip.

FIG. 21A is a chart showing relative mRNA expression between standard media (left, grey bars), viscous media (50% Percoll) (blue, middle bars) and inflammatory inducing media containing Cytomix cytokines (right, pink bars), after 24 hours of treatment.

FIG. 21B shows micrographs of cells (left) corresponding to lower power micrographs of the channels (right). Stained ICAM-1 (pink) and nuclei (blue). Upper is a control intestine on-chip, middle is an inflamed intestine on-chip and lower is a chip treated with viscous media, 50% Percoll, intestine on-chip.

FIG. 21B showing micrographs of cells (left) corresponding to lower power micrographs of the channels (right). Stained ICAM-1 (pink) and nuclei (blue). Upper is a control intestine on-chip, middle is an inflamed intestine on-chip and lower is a chip treated with viscous media, 50% Percoll, intestine on-chip.

Figure 21C:
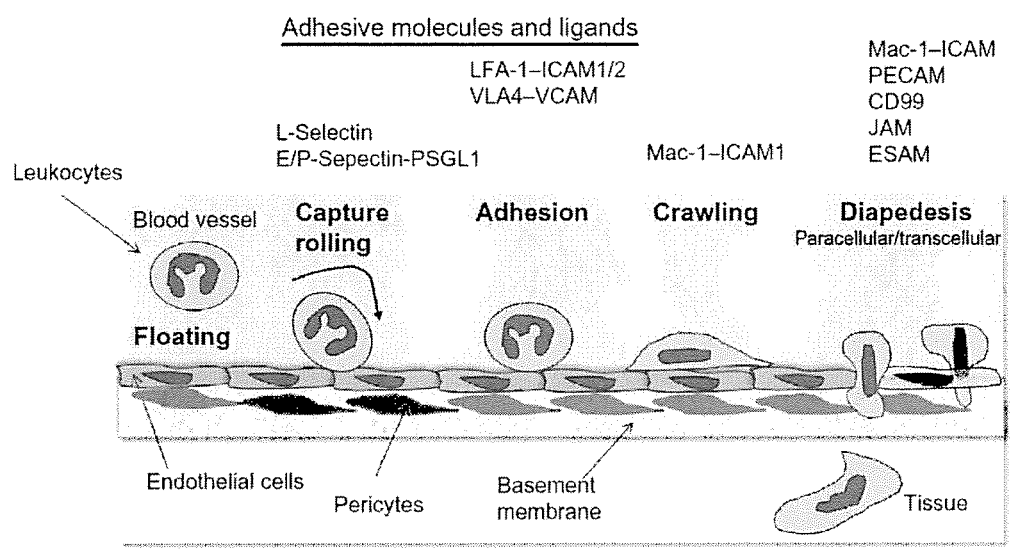

FIG. 21C shows a schematic image of representative blood vessel endothelial tissue as a candidate for white blood cell interactions, e.g. PBMCs, neutrophils, lymphocytes, etc., illustrating exemplary cell surface adhesion molecules associated with stages of white blood cell interactions with endothelium. Starting with blood cells floating in a fluid comprising an fluid modifying agent, white blood cells undergo capturing (tethering), and rolling, then when appropriate adhesion molecules are present (e.g. inflammation) white blood cell rolling becomes arrest of movement along the endothelial cell(s) then followed by diapedesis through the endothelial layer.

Figure 22A:
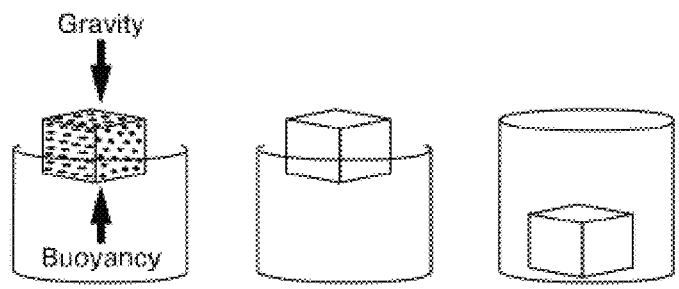
Figure 22B:
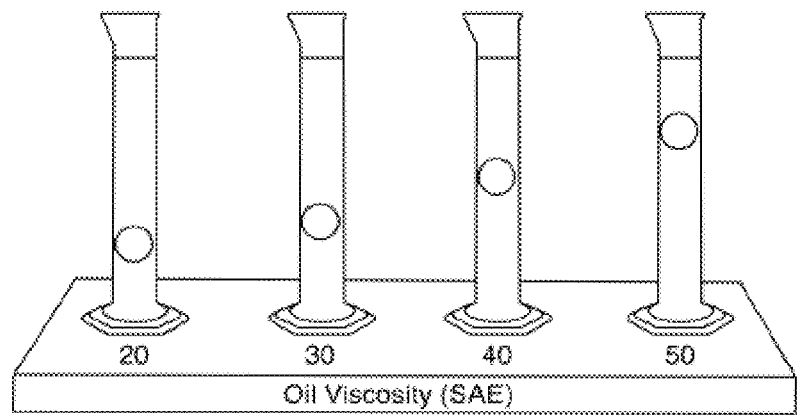
Figure 22C:
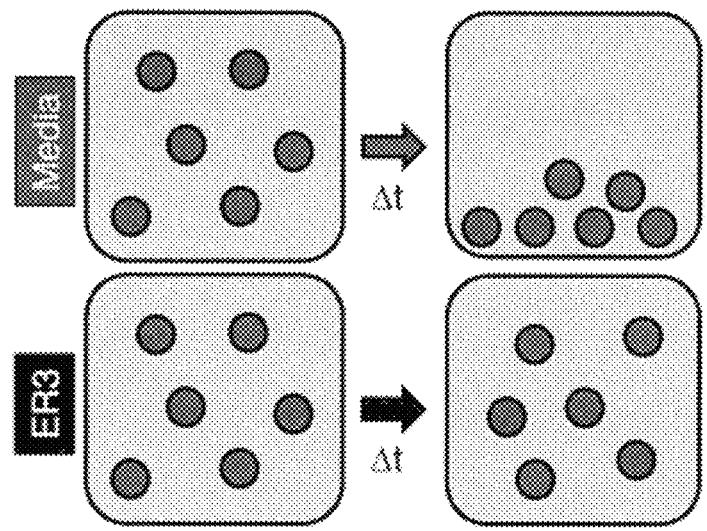

FIGS. 22A-C shows an exemplary illustration of Archimedes Principle related to buoyancy. FIG. 22A shows an exemplary illustration of Archimedes Principle where a floating object must displace a greater mass of solution than the mass of itself in order to float. FIG. 22B shows an exemplary illustration where the more dense the solution (in mass, such as adding oil (SAE) at 20%, 30%, 40% and 50%, left to right) for increasing viscosity) demonstrating that less of a denser solution needs to be displace for the same object to stay afloat. FIG. 22C shows an exemplary illustration of media with Percoll (lower cubes) Prohibits Cell Settling and solves the problem of cells settling within Emulate Chips and POD reservoirs.

FIG. 23A-B shows exemplary schematic diagrams of structures in non-Newtonian dispersions at rest (FIG. 23A) and under shear (FIG. 23B) showing exemplary shape changes of particles undergoing a change in orientation under flow (upper squares); stretching second down); deformation (third down) and disintegration (bottom). (Chhabra, "Non-Newtonian Fluids: An Introduction." Mercury.;1 (10):3 downloaded 1-22-18).

Figure 24A:
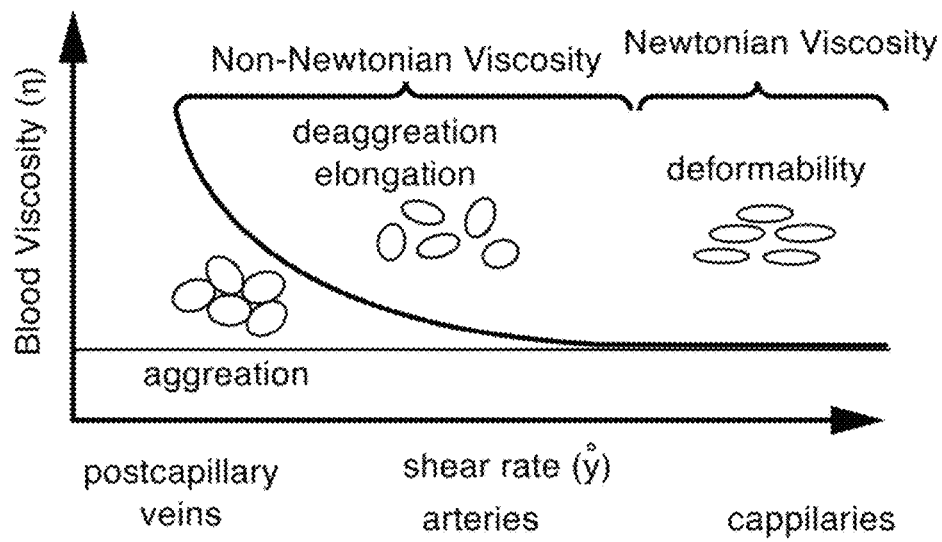
Figure 24B:
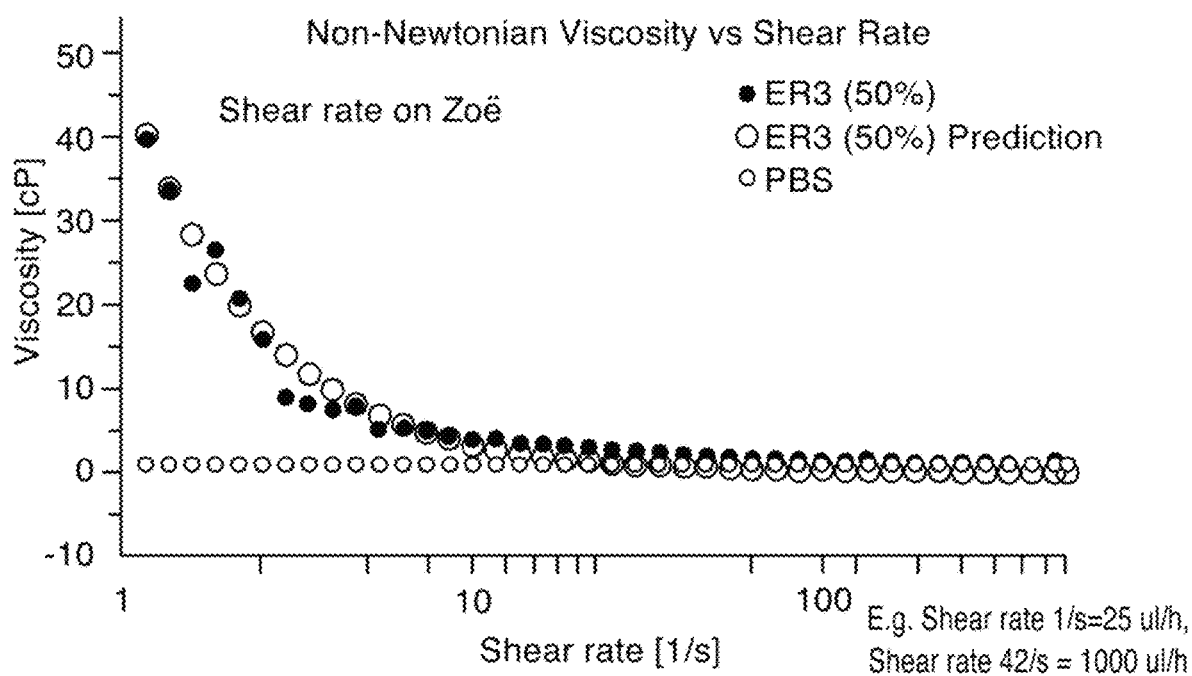
Figure 24C:
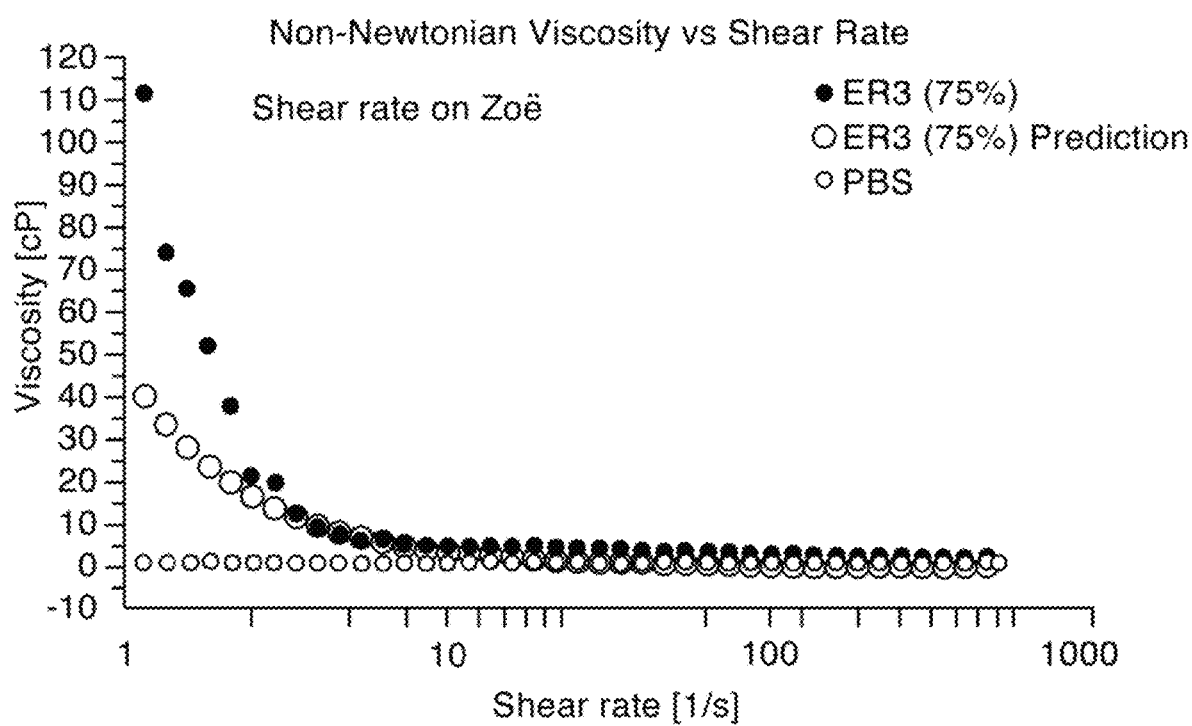

FIG. 24A-C shows an exemplary illustration of and viscosity measurements using a fluid-modifying reagent, e.g. Percoll, for emulating rheological properties of human blood (ER3-Percoll at 50%). Percoll (50%) similar to blood, exhibits shear-thinning properties. FIG. 24A illustrates a shear-viscosity curve for blood as changes in blood viscosity in relation to shear rate. From left to right along the x-axis, at lower shear rates and lower blood viscosity, exemplary cells as red blood cells in post-capillary veins, undergo aggregation. As shear rates increase at non-Newtonian viscosity, such as in arteries, cells disaggregate and elongate. At yet higher shear rates, such as in capillaries; Newtonian viscosity results in deformability, which for physiological reasons are contemplated to result in ease of flow through the small diameters of capillaries. FIG. 24B illustrates Non-Newtonian Viscosity vs Shear Rate in a pod using fluid containing ER3-Percoll at 50%. The lower line represents PBS, while the upper lines show predicated values (open circles) vs. viscosity measurements (closed circles). E.g. Shear rate 1/s=25 ul/h, Shear rate 42/s=1000 ul/h. FIG. 24C illustrates Non-linear behavior at low shear rates using Percoll at 75%. Percoll (75%) emulates rheological properties of blood (e.g. shear dependent viscosity).

FIG. 25 shows an exemplary illustration of viscosity of Percoll Depends on Density of Particles and Flow Rate. Percoll solution in media [%] is 25%; 50% and 75%. At low flow rate: 30 ul/h viscosity of ER3 increases with the increased partition of Percoll particles in the solution. At high flow rate: 1000 ul/h no significant differences in the viscosity of different Percoll solutions are observed at the high flow rates due to the shear thinning effect.

Figure 26A:
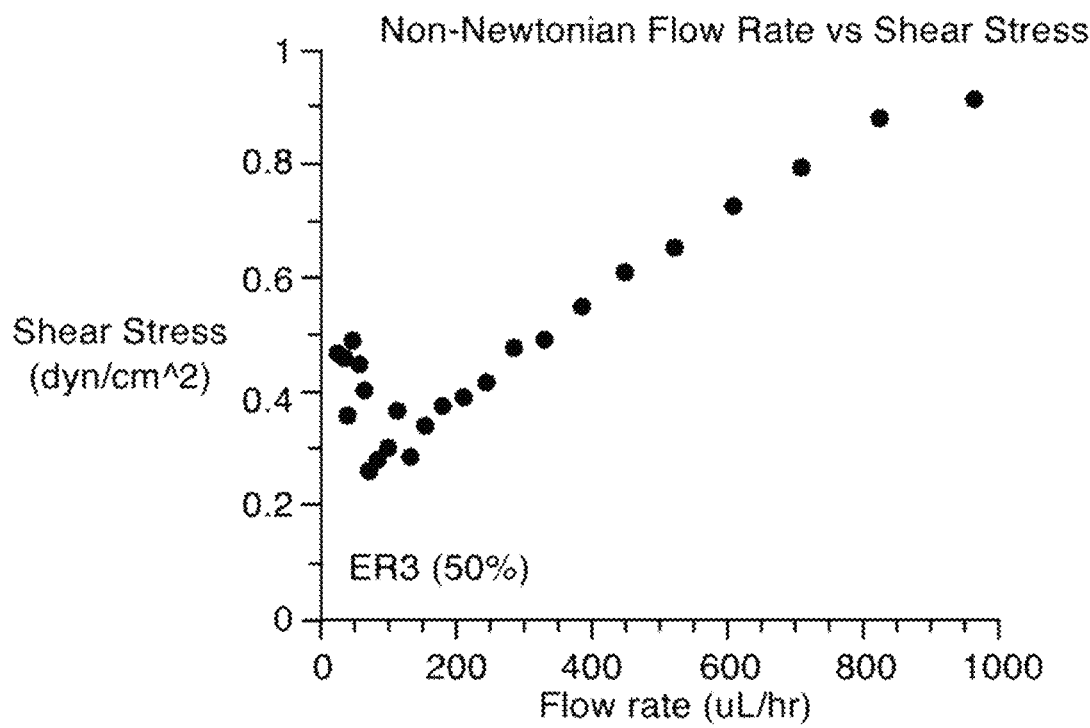
Figure 26B:
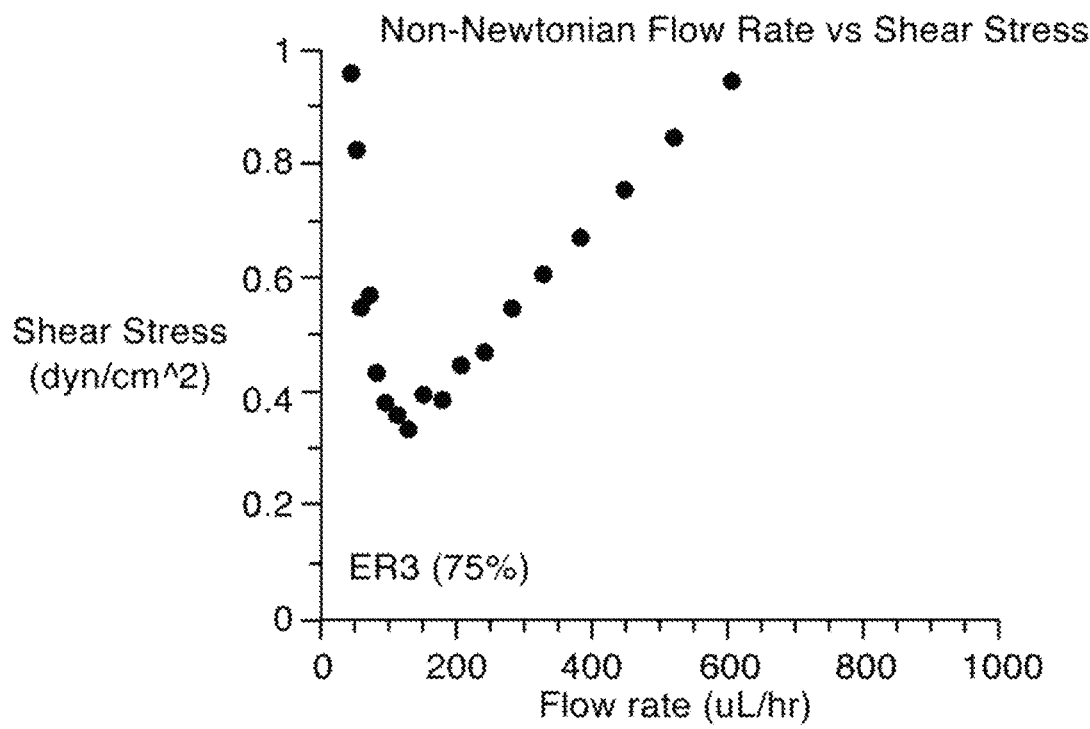

FIG. 26A-B shows an exemplary illustration where the addition of Percoll Enables Higher Shear Stress at Lower Flow Rates. Non-Newtonian Flow Rate vs Shear Stress. Flow Rate (microL/hr). To achieve Shear Stress of 1 dyn/cm2: media–3.5 ml/h flow rate comparing (50%)–1000 ul/h to ER3 (75%)–30 ul/h flow rate. Percoll enables achievement of higher shear stress using a pressure manifold system. FIG. 26A Percoll added at 50%. FIG. 26B Percoll added at 75%.

Figure 27:
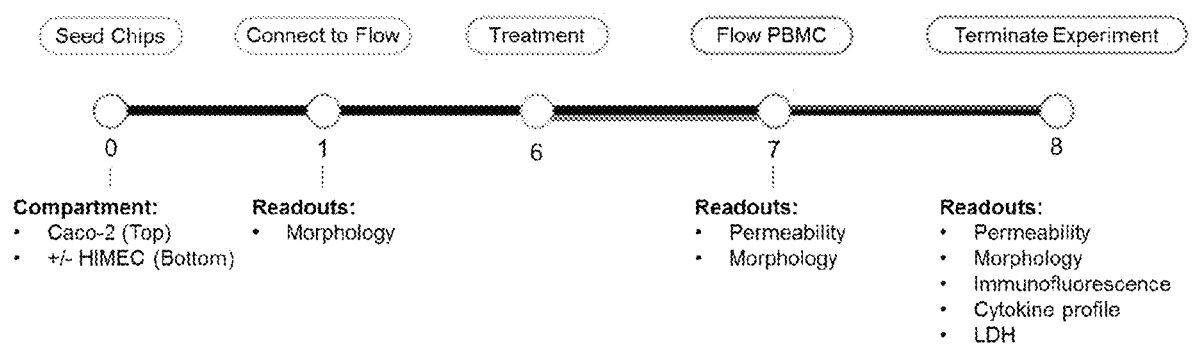

FIG. 27 shows a schematic of an exemplary timeline for assessing T-cell recruitment in Caco-2 Intestine on-Chip. Exemplary Chip Set-up: Day 0—Seed Chips Compartment: Caco-2 (Top)+/– HIMEC (Bottom); see exemplary Table X. Day 1—Connect to Flow. Day 6—Treatment: see exemplary Table X. Day 7—Flow PBMC Exemplary Readouts: Permeability; Morphology; etc. Day 8—Terminate Experiment: Exemplary Readouts: Permeability; Morphology; Immunofluorescence; Cytokine profile; LDH, etc.

Figures 28A, 28B, 28C, 28D:
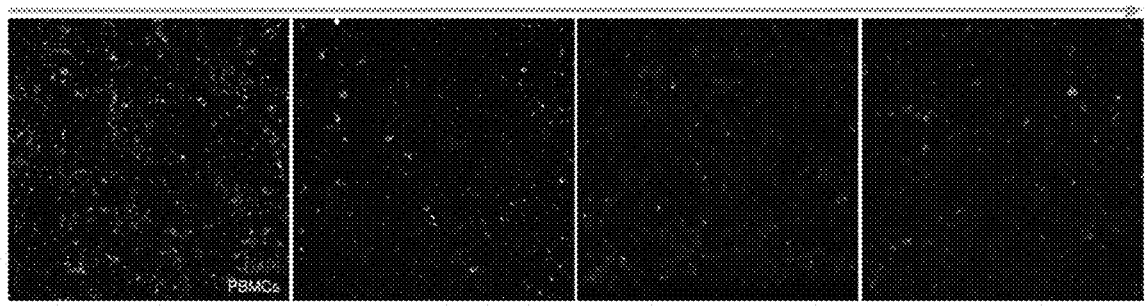

FIG. 28A-D shows exemplary inclusion of Percoll in the basal channel facilitates immune recruitment of Intestine-Chip in the Zoe™ (pressure manifold) Culture Module. DAPI (dark blue nuclei) and PBMCs (colored light blue). Blue arrow across the panels at the top represents decreasing Numbers of Immune Cells Recruited to the Intestine-Chip Epithelial Channel. FIG. 28A shows epithelial cells without HIMECs treated with anti-CD3/anti-CD28 and TNF-α/IL-1β/MCP-1. FIG. 28B shows epithelial cells with HIMECs treated with anti-CD3/anti-CD28 and TNF-α/IL-1β/MCP-1. FIG. 28C shows epithelial cells with HIMECs treated with anti-CD3 and TNF-α/IL-1β/MCP-1. FIG. 27D shows no epithelial cells present with HIMECs treated with TNF-α/IL-1β/MCP-1.

Figure 29:
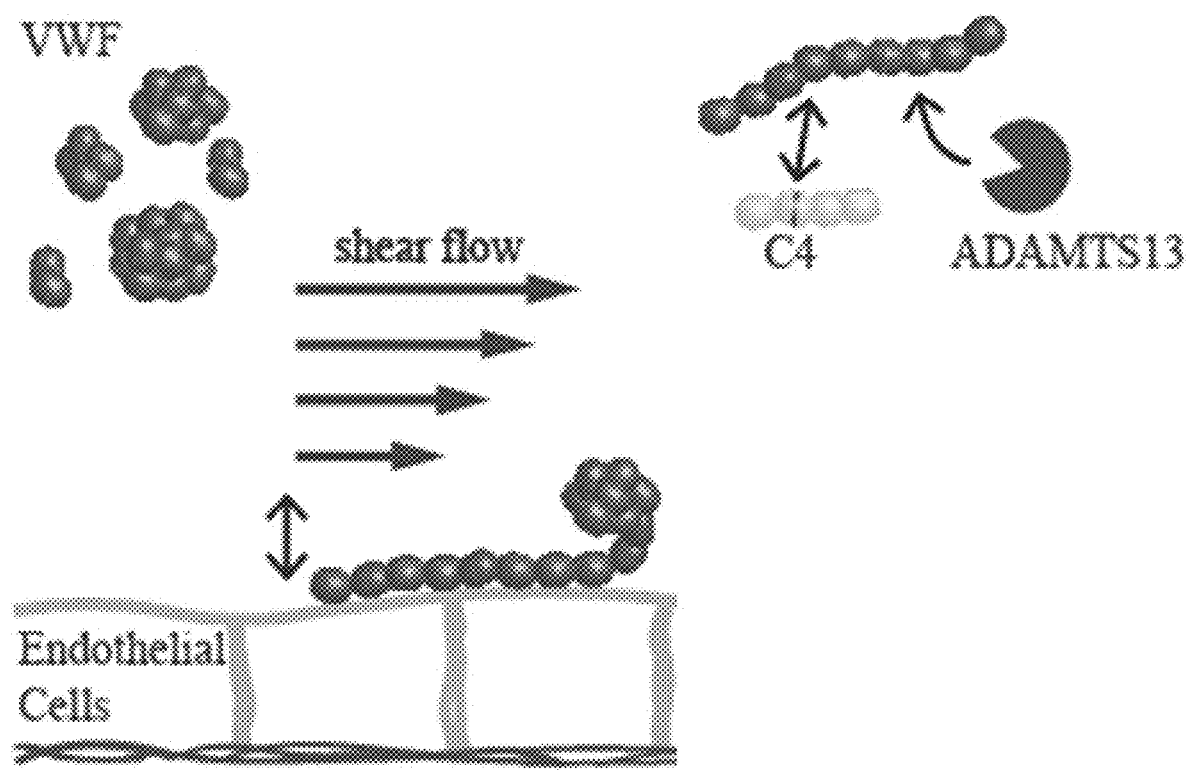

FIG. 29 shows schematic diagrams illustrating Willebrand factor (vWF) in a coiled conformation circulating in a blood vessel (left) then elongated after exposure to shear during coagulation (right). www.shenc.de/B3-Raedler-res.htm, downloaded Sep. 11, 2018.

Figures 30A, 30B, 30C:
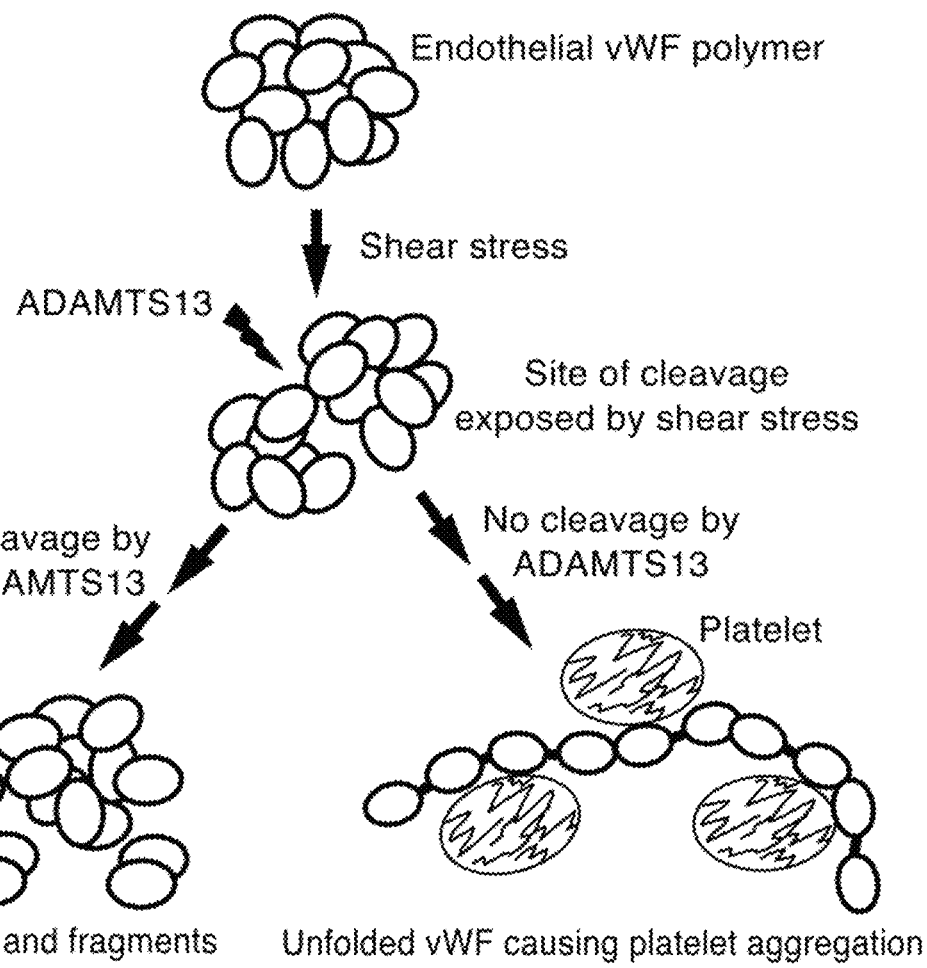

FIG. 30A-C shows schematic diagrams illustrating Willebrand factor (vWF) conformational changes from a coiled endothelial vWF polymer protein in FIG. 30A, then when exposed to shear stress FIG. 30B in the presence of ADAMTS13, cleavage sites exposed by shear allow ADAMTS13 proteolysis cleavage of the coiled polymer FIG. 30C (left) into smaller multimers and fragments. Alternatively, in the presence of shear and the absence of ADAMTS13 cleavage, FIG. 30C (right), as vWF unfolds binding sites are exposed by conformational changes allowing attachment to platelets and other components causing platelet aggregation. Tsai "Platelet Activation and the Formation of the Platelet Plug: Deficiency of Adamts13 Causes Thrombotic Thrombocytopenic Purpura." Arteriosclerosis, thrombosis, and vascular biology, 23(3):388-396 (2003).

FIG. 31A-B shows exemplary representative images showing effect of human endothelial cells (HUVECs) growth in microfluidic channel and perfused overnight with (FIG. 31A) standard cell culture medium (EGM2-MV) at low shear rate or (FIG. 31B) with EGM2-MV including a fluid-modifying reagent to recapitulate physiological relevant shear stress. When compared to cells grown at physiological shear rate, endothelial cells grown at low shear rate express higher levels of the pro-thrombotic receptor vWF (panels on the left and center). Platelets tend to firmly interact and adhere on HUVECs grown at low shear rate (right).

Figure 32A:
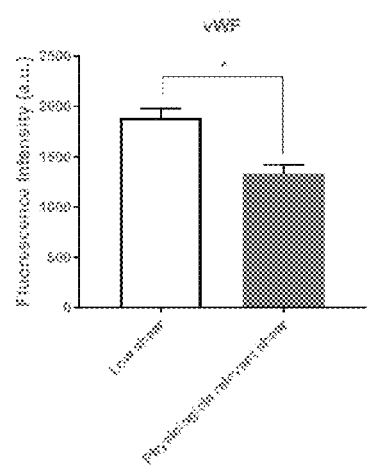
Figure 32B:
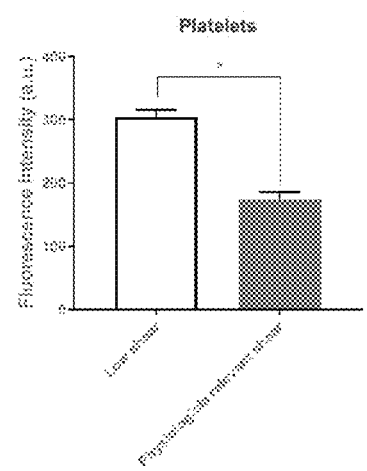
Figure 32C:
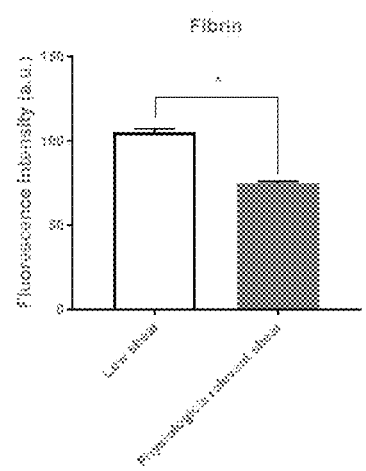

FIG. 32A-C shows exemplary results obtained via image analysis and quantification of the fluorescence intensity of coagulation components, at low shear vs. physiologically relevant shear, demonstrates that physiological relevant shear enhances the antithrombotic function of healthy endothelial surface and improves the signal-to-noise ratio of the in vitro assay. Accordingly, human endothelial cells grown at low shear rate express higher levels of the pro-thrombotic receptor vWF when compared to cells grown at physiological shear rate (left). Exposure to physiological shear rate suppresses unwanted platelet adhesion (center) and fibrin deposition (right), both markers of injured or inflamed endothelial cells rarely detectable on healthy endothelial vasculature. FIG. 32A exemplary cWF. FIG. 32B exemplary platelets. FIG. 32C exemplary fibrin.

FIG. 33A-C shows exemplary results of using a fluid-modifying reagent (Percoll) in order to induce shear. Treatments included: 1. Blood (FVIII inhibited); 2. Blood+FVIIa (reconstituted); 3. Low shear (untreated BBB On-Chip); 4. Physiological relevant shear (shear treated BBB On-Chip). FIG. 33A shows an exemplary florescent image of a whole (entire) channel on chip at low magnification. Fibrin is shown in cyan. FIG. 33B shows magnified details from channels shown in FIG. 33A. FIG. 33C shows graphical results comparing the 4 types of treatment.

FIG. 34 demonstrates problems: a loss of barrier function. Brain endothelial cells grown in media 1 (M1): hEndothelial SFM+1% PPP (Puromycin), loose barrier function by Day 10 as shown by bright field mocroscope images of cells on-chip with a corresponding dextrin leakage chart. Additionally, Immunofluorescently stained micrographs with a corresponding graph of barrier funtion loss, demonstrates Endothelial (iHBMEC) tight junctions loss of barrier function by Day 10 in a dose dependent fashion. dose-dependent response to TNFalpha. Control (left) 100 ng/ml TNF (right). Thus, loss one or more causes of a loss of barrier function in human brain endothelial cultures provides difficulties with immune recruitment assays.

FIG. 35 shows exemplary results of Media Optimization, Day 07 and 10. Bright field microscope images: upper panels Media 1, lower panels Media 2. Right panels ECM 1 and left panels ECM 2 (+Laminin). Lower graph of % dextran leakage over time, shows Media 2 enhances proliferation of iHBMECs but does not improve barrier function. ECM2 seems to improve iHBMEC monolayer morphology.

FIG. 36 shows exemplary results of Effect of Puromycin Selection on Barrier Function. Media 1 (M1): hEndothelial SFM+1% PPP. M2: M1+Endothelial growth medium (EGM) supplements; M4: Advanced DMEM/F12+1% PPP+ EGM supplements. Graphs upper, M1 vs. M4, and lower M2 vs. M4, demonstrated that Puromycin treatment does not seem to contribute to improved barrier maintenance or robustness in the "long-term".

Figure 37:
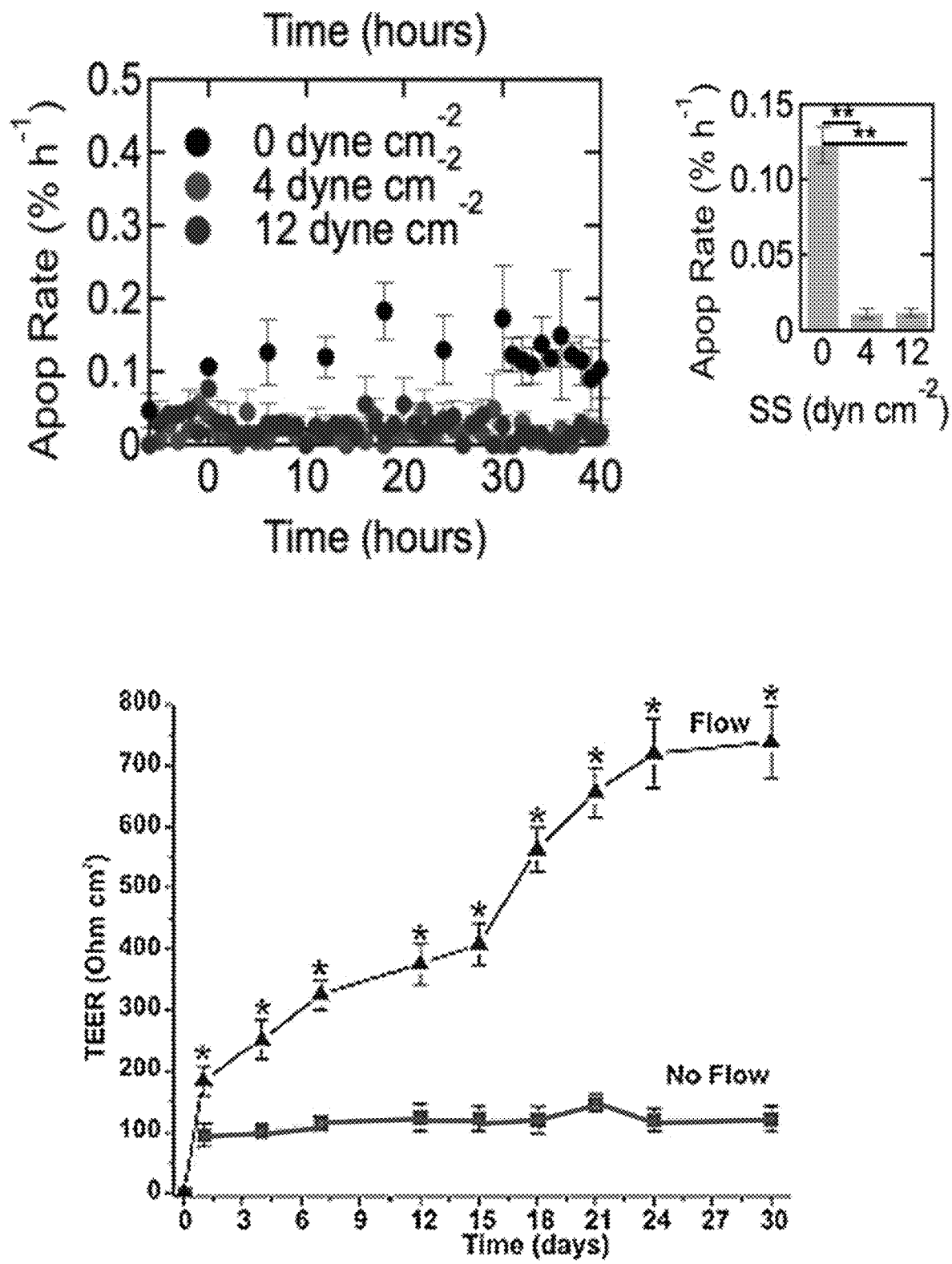

FIG. 37 demonstrates apoptotic rates over time, apoptotic rates under different shear conditions, and TEER. For reference, Cucullo, et al., The role of shear stress in Blood-Brain Barrier endothelial physiology. BMC Neurosci. 2011.12-40; and DeStefano, et al., Effect of shear stress on iPSC-derived human brain microvascular endothelial cells (dhBMECs). Fluids Barriers CNS. 2017. 14(1):20.

Figure 38:
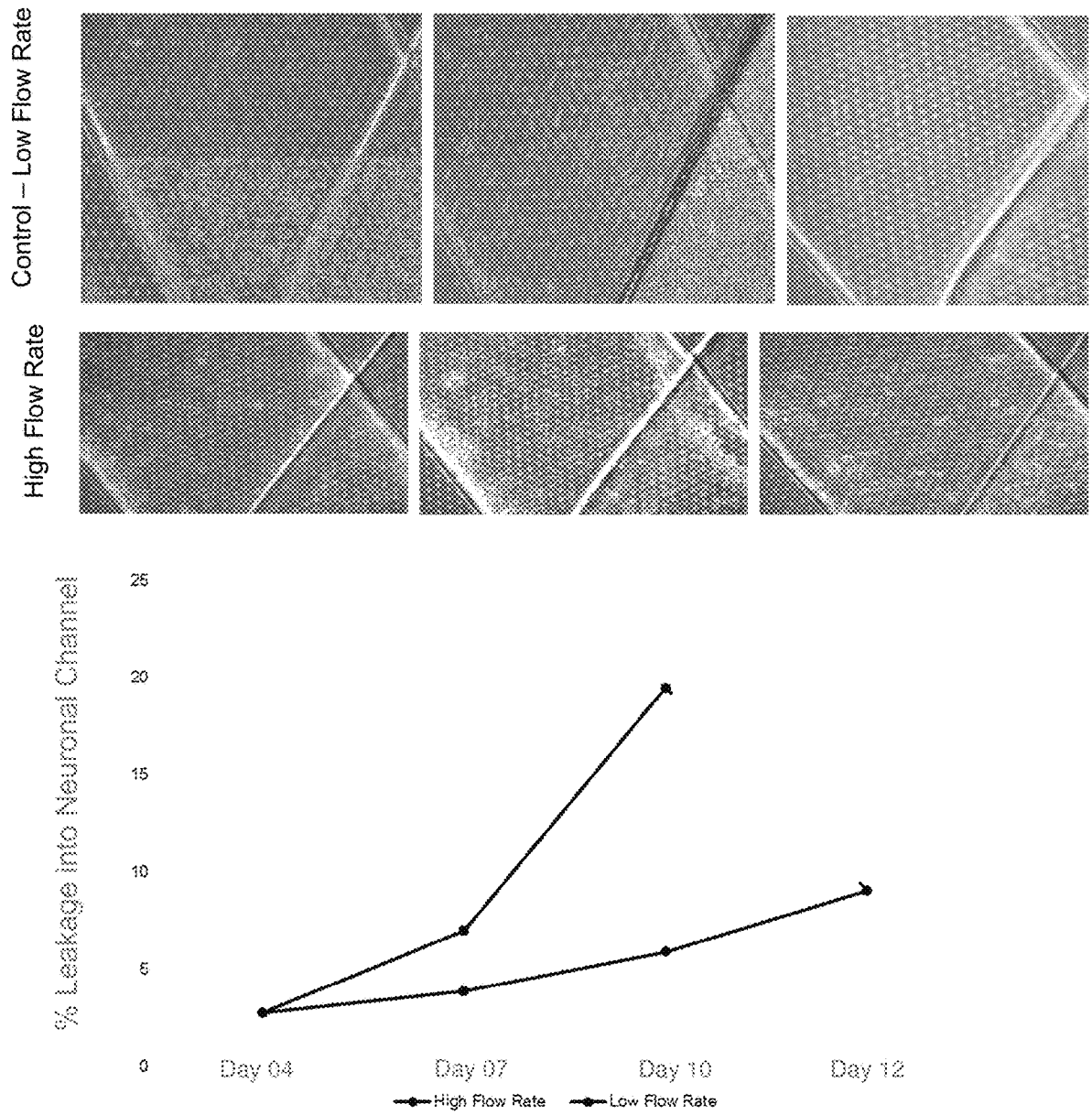

FIG. 38 shows an exemplary Effect of Shear on hBMEC Physiology under a high flow rate (600-900 ul/hr) and recirculation which facilitates maintenance of barrier function in the BBB-Chip. Morphology (brightfield) for Day 04; Day 07; Day 10 for upper panels Control—Low Flow Rate and lower panels High Flow Rate. Barrier function was measured using 3 kDa Dextran in the chart below. Barrier function—3 kDa Dextran is better at High Flow Rate vs Low Flow Rate.

FIG. 39 shows exemplary immunostaining—Day 07; before and after, upper panels. And Immunostaining—Day 10; before and after, lower panels.

FIG. 40 shows exemplary Improving shear stress and recirculating media generates a more robust BBB, as measured by barrier function and morphology.

Figures 41A, 41B:
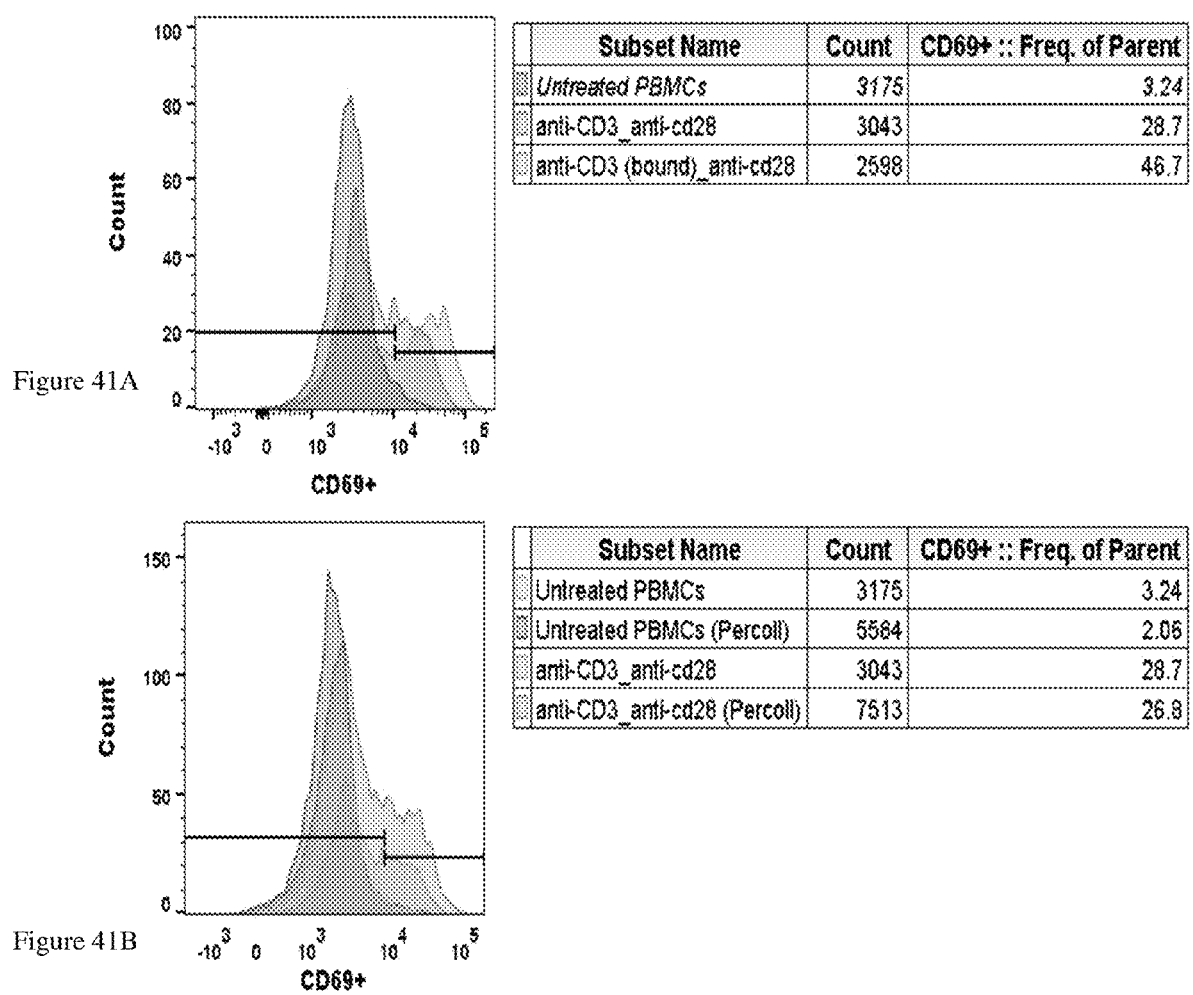

FIG. 41A-B shows exemplary assessing PBMC Activation for assessing PBMC Pre-activation. CD69+Flow-Cytometry (FACs) Assay. FIG. 41A shows exemplary FACS analysis of CD69 stained cells without using Percoll. FIG. 41B shows exemplary FACS analysis of CD69 stained cells using Percoll.

Figure 42:
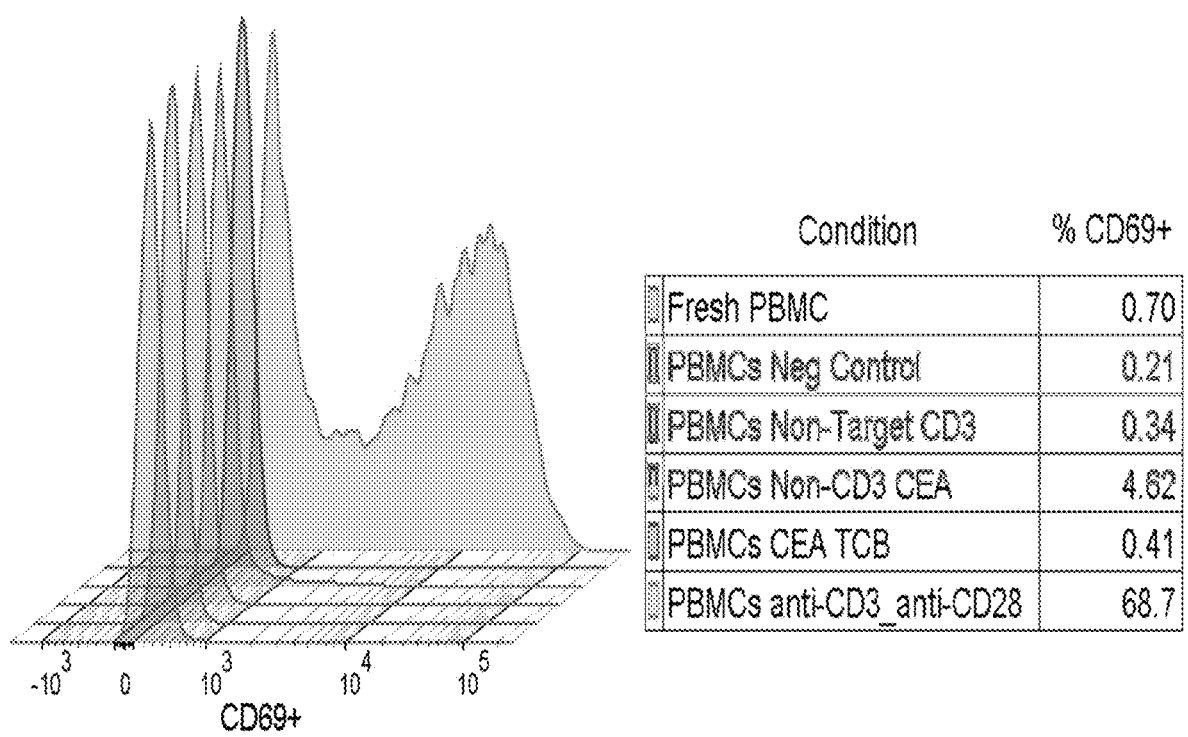

FIG. 42 shows exemplary assessing Early Activation of Peripheral Immune Cells. Pre-incubated PBMCs to be circulated through the vascular channel of the Intestine-Chip were assessed for the early activation marker CD69. CD69 levels are similar in all cases except the anti-CD3/anti-CD28 positive control. Thus CD3 binding without co-binding of the tumor target by the TCBs on the Intestine-Chip does not activate the immune cell population.

DESCRIPTION OF THE INVENTION

The present invention contemplates compositions, devices and methods of simulating biological fluids in a fluidic device, including but not limited to a microfluidic chip. In one embodiment, fluid comprising a colloid under flow in a microfluidic chip has a fluid density or viscosity similar to a bodily fluid, e.g. blood, lymph, lung fluid, or the like. In one embodiment, a fluid is provided as a rheologically biomimetic blood surrogate or substitute for simulating physiological shear stress and cell dynamics in fluidic device, including but not limited to immune cells.

During the development of the present inventions, problems were encountered in microfluidic systems in relation to assays where cells were added to liquids, including liquids flowing through tubing and microfluidic channels, and in liquids flowing out of microfluidic chips destined for a downstream attached chip, e.g. systems comprising more than one chip. More specifically, these opportunities for cell settling during the course of an experiment throughout a microfluidic chip system induced variability in the cell numbers encountering cell layers in the main channel of the device. A few specific examples of where cell settling would alter experimental results are described herein.

Additional problems with partial solutions are described in detail in the following section.

I. Advantages Of Modifying Fluid Viscosity.

As one example of results obtained with a variable numbers of suspended cells in solution encountering endothelial cells by settling out rather than a specific receptor mediated adhesive-like interaction, a high background of nonspecific interaction was observed obscuring physiological relevant rates of attachment leading to diapedesis. As a contemplative example observing suspended cells in fluids through chip to chip fluidic interactions, there may be variability in metastatic rates of tumor cells migrating from one chip through the tubing into another chip caused by cell settling within the microfluidic channels of the proximal chip, cell settling within tubing connecting the proximal to distal chip, i.e. tubing between chips, which would alter experimental results. For reference, this type of cell settling induced by microfluidic system design is referred to as nonphysiological cell settling. In contrast, physiological cell settling refers to cell settling that may occur due to changes in physiological fluid properties that may occur in vivo during disease and aging; and in vitro mimicking of fluid properties in microfluidic chips.

A. Non-Physiological Cell Settling; Flipping Fluidic Devices; And Failed Uses of Some Agents Added To Fluids.

Several methods were considered or used to address this problem including: using chips flipped upside down for a certain amount of time, i.e. flipping chips; chips designed having a vascular channel on top, with the tissue channel underneath the chip membrane; designing Pods and/or instruments for holding and incubating a chip upside-down throughout culture or during the recruitment assay. Of these methods, recruitment assays appeared to simulate in vivo immune recruitment while the chip was inverted, using gravity to move the immune cells to the endothelial layer next to the chip membrane. Such that, flipping chips for immune recruitment assays was used as part of an exemplary protocol for immune-cell recruitment assays. Thus, in some embodiments, a microfluidic chip comprising endothelial cells and immune cells is flipped during the duration of an immune recruitment assay.

However, flipping chips containing cells in fluids bathing the cells (within microfluidic channels), merely used gravitational forces on cells to move immune cells into position to interact with endothelial cells. In some embodiments, flowing liquids containing immune cells were added to the chips before flipping. In some embodiments, flowing liquids containing immune cells were added to the chips after flipping. Regardless of when the fluid and cells were added, flipping allowed the use of gravitational forces along with the forces provided by the liquid and/or liquid cell interactions, onto cells for moving immune cells into position to interact with endothelial cells. However, shear rates induced by flowing liquids also impeded the recruitment of circulating immune cells onto exemplary endothelium in an intestine on-chip, even when flipped. These shear rates on-chip were are further affected by viscosity of the liquid, as described herein.

One solution used to overcome non-physiological cell settling, was presented in the U.S. Pat. No. 8,647,861, herein incorporated by reference in its entirety, associated with neutrophil recruitment experiments in lung microfluidic chips and in Benam, et al., "Small airway-on-a-chip enables analysis of human lung inflammation and drug responses in vitro." Nature Methods, online pages 1-7, online methods and Supplementary (2015)). In Benam, et al., The chips were flipped upside down, and neutrophils (1×107 cells ml−1) were flowed (2.7 ml h−1; 1 dyn cm−2) through the microvascular channel of the device to mimic the physiological hemodynamic conditions in human postcapillary venules. After 10 min, unbound neutrophils were washed away by flowing cell-free RPMI-10% FBS medium 5 min, then chips were analyzed for bound neutrophils.

Thus, shear force/gravity affects the immune cells, and in turn, the effectiveness of the recruitment. Specifically, typically the microfluidic chip's bottom channel was used as the vascular channel. Accordingly, to be recruited to the endothelium, the immune cells have to interact with the channel's top wall (where the endothelial cells lie, coating the bottom of the membrane). This means that the immune cells have gravity working against them, which we believe makes the process inefficient. In support of this hypothesis, we have found that recruitment assays work much better with the Chip inverted, when gravity helps the immune cells reach the membrane. Flipping chips has been part of the standard protocol for immune-cell recruitment assays before the present invention.

Accordingly, to be recruited to the endothelium on the upper wall of the channel where the endothelial cell layer was adjacent to the chip membrane having overlying cells in the upper channel, the immune cells in fluids bathing the lower channel should be able to physically interact with the vascular (lower) channel's top wall (where the endothelial cells are located in a layer adjacent to the chip membrane, which separates the endothelial cell layer from the cell layer in the other channel (in a 2 channel chip). This means that in a typical orientation with the vascular channel below the other channel, then the immune cells have a gravitational force pulling them down, i.e. settling away from, the endothelial cells adjacent to the membrane and cells in the upper channel. As this does not appear to be the case in vivo, using microfluidic chips in an upright configuration results in an inefficient in vitro assay.

More specifically, the chip was flipped upside down prior to addition of fluids containing suspended neutrophils in order to provide a desired shear force on neutrophils in solution and on the endothelial layer for allowing neutrophils to attach to the endothelial layer in a more physiologically relevant in vivo-like manner. This approach using microfludic chip flipping in order to bring more cells suspended in fluids into contact with the chip membrane or cell layers (e.g. attached to the chip membrane) was used to study immune cell recruitment, e.g. attaching and diapedsis through cell layers on chips, specifically for neutrophil recruitment in small airway on-chip work (e.g. COPD: Benam, et al., "Small airway-on-a-chip enables analysis of human lung inflammation and drug responses in vitro." Nature Methods, online pages 1-7, online methods and Supplementary (2015)).

Moreover, high shear rates were used for kidney on-chips was previously accomplished through flipping the chip, as described in PCT/US2016/064179 published as WO2017095899 (Jun. 8, 2017) "Gradient microfluidic devices and uses thereof", herein incorporated by reference in its entirety; etc._Kidney cells grew better in the upside down chips.

However, flipping the chip to achieve higher shear rates or to simulate changes in particulate cell buoyancy (through changing directional forces of gravity) was merely a partial fix for this type of problem. In part, problems from flipping chips during experiments were caused by interruptions with incubation processes, in addition to not providing an actual "mimic" for physiological processes. In part because blood vessels in vivo are circular thus having circular endothelial cell layers frequently at rapidly changing orientation to gravity. Thus 'upside' down would mimic a portion of the overall interaction of white bloods cells with endothelium, or other types of suspended cells with cell layers.

Others have attempted solutions for overcoming in vitro settling of large cells suspended in solution, such as carcinoma cells (up to 25 µm), chondrocytes (~20 µm), liver cells (~20 µm), macro-phages (20-80 µm), and hematopoietic stem cells (30-40 μm). One exemplary solution was add alginate to PBS buffer solutions to mimic blood rheology and reduce cell settling for large cells including circulating tumor cells (CTCs) (see, for example, Launiere, et al., "Rheologically biomimetic cell suspensions for decreased cell settling in microfluidic devices." Biomed Microdevices, 13: 549-57, 2011). However, experiments on-chip using alginate, did not provide a physiologically relevant fluid for enhancing immune cell attachment to endothelium. Moreover, other exemplary agents, such as dextran and gum material did not provide a basis for a working immune cell attachment assay on-chip. In fact, these agents either induced inflammatory endothelial cells in the absence of an inflammatory inducing agent for a controlled experiment, or did not induce recruitment of desired immune cells, for examples of a nonworking system on-chip.

Polyvinylpyrrolidone (PVP) was used in microfluidic devices PVP(Leshansky et al. "The rheologic properties of erythrocytes: a study using an automated rheoscope" Rheol Acta (2007) 46:621-627). However, Leshansky et al. mixed PVP with whole blood, taken from healthy volunteers and thalassemia patients, diluted to a final hematocrit of 0.4% in 5 ml of phosphate-buffered saline (PBS; pH 7.4, osmolarity 290 mOsm/kg) containing 8 or 6% by weight polyvinyl pyrrolidone (PVP; MW 360,000; Sigma-Aldrich). Red Blood Cells (RBCs) suspended in PBS:PVP was used to investigate the motion and deformation of RBCs suspended in a high-viscosity medium flowing through a microchannel.

B. Discovery Of Better Methods Using A Fluid Density-Modifying Reagent.

We considered several ways to better address immune cell recruitment without the need to invert the Chip. Other remedies were tested for use with immune cell recruitment on-chip, including but not limited to altering shear forces acting upon the white blood cells and endothelial layer on-chip, in addition to altering the density of the fluids on-chip and/or alerting the viscosity of fluids on-chip. Thus, liquids used on-chip, were altered by the addition of a "fluid-modifying reagent." It was discovered during the development of the present inventions, that addition of Percoll, as one example of a fluid-modifying reagent, increased media viscosity and improved immune cell-endothelium interactions, i.e. increased the number of white blood cells attached to the endothelial layer in an exemplary intestine on-chip.

Thus, in comparison to previous methods, during the development of the present invention data showed that immune-cell recruitment assays function better (e.g. enhanced recruitment after inflammation), particularly compared to a chip that wasn't flipped, when the fluid comprises a density-modifying reagent. The density-modifying reagent may further comprise soluble dense materials, e.g. polymers, sugars (e.g. dextrans), starches, cellulose, dense proteins, colloids, etc. In some embodiments, a density-modifying reagent may be silica colloids, nanoparticle suspensions (e.g. gold nanoparticle). In some embodiments, a density-modifying reagent is Percoll.

Some examples of Percoll include but are not limited to Percoll PLUS referring to a low endotoxin reagent for density gradient centrifugation of cells, viruses, and subcellular particles. Percoll Plus is composed of colloidal silica covalently coated with silane.

Percoll comprises colloidal silica coated with polyvinylpyrrolidone (PVP). In some embodiments, silica particles range from 15 to 30 nm diameter. Free PVP may be present around 1% to 2%. Percoll including commercial solutions such as Percoll PLUS, is considered non-toxic, almost chemically inert, and does not appear to adhere to membranes. Sources include but are not limited to: GE Healthcare Sciences; Sigma-Aldrich, etc. In some embodiments, characteristics may be customized by diluting with solutions of NaCl or sucrose.

In some embodiments, a density-modifying reagent comprises Ficoll.

Ficoll solutions, including but not limited to Ficoll PM70, refer to high molecular weight sucrose-polymers formed by copolymerization of sucrose with epichlorohydrin, which has minimal toxicity, favorable viscosity and osmotic properties, up to 50% w/v in solution.; Ficoll PM400 refers to a synthetic neutral, highly-branched hydrophilic polymer of sucrose with an average molecular weight of 400,000, a high molecular weight sucrose-polymers formed by copolymerization of sucrose with epichlorohydrin. The molecules are highly branched and the high content of hydroxyl groups leads to very good solubility in aqueous media. Concentrations of up to 50% (w/v) covering densities of up to 1.2 g/ml may be achieved. Further, it has better osmotic properties than sucrose. Useful for separating cells that are sensitive to centrifugation and for separating cells of similar density but different size (under conditions of sedimentation at unit gravity). Further, it does not penetrate biological membranes.

Ficoll PM400 may serve as a material for preparation of Ficoll-Paque gradients.; Ficoll-Paque, Ficoll-Paque PLUS, Ficoll-Paque PLUS refers to a sterile, ready-to-use density media containing Ficoll PM400, sodium diatrizoate and disodium calcium EDTA. The density has been optimized for the isolation of human lymphocytes from peripheral blood. Ficoll Paque PREMIUM refers to a Ficoll preparation that was optimized for the isolation of mononuclear cells from human peripheral blood, bone marrow, and umbilical cord blood. Sterile, ready to use reagent used to prepare mononuclear cell preparations from peripheral blood, bone marrow, and umbilical cord blood by density gradient centrifugation.; Ficoll-Paque PREMIUM 1.073 may be used when isolating or using lower-density human mononuclear cells (e.g., mesenchymal stromal cells or monocytes).

We found that immune-cell recruitment assays function better (e.g. enhanced recruitment after inflammation, particularly compared to a Chip that wasn't flipped) when the fluid used incorporates a density-modifying reagent. The density-modifying reagent can comprise soluble dense materials (e.g. polymers), sugars (e.g. dextrans), starches, cellulose, dense proteins, or colloids. In one embodiment, silica colloids are contemplated. In another embodiment, nanoparticle suspensions (e.g. gold nanoparticle) are contemplated. In a preferred embodiment, the present invention contemplates Percoll or Ficoll (the last two were developed by separating cells or cell parts based on their density during centrifugation).

Without being bound by theory, increasing the density of a fluid carrying immune cells increases the buoyancy of these cells. Specifically, once a certain density is reached, the cells become buoyant, meaning that they float upwards in the channel. Accordingly, cells floating upwards can better interact with the endothelial cells present at the top of the channel (under the membrane). The end result is a protocol that, amongst other advantages, allows for effective immune-cell recruitment and specifically without needing to flip Chips. The latter part is especially an advantage in the context of our culture module (which does not easily permit inverting the Chip).

The application is about non-Newtonian fluids creating turbulent flow, which encourages immune cell interaction with channel walls. Additionally, not being bound by theory, a density-modifying agent, such as Percoll, may interrupt laminar flow patterns in microchannels. As a non-Newtonian fluid, blood in blood vessels may not flow in a straight laminar path. Instead, blood, containing red blood cells, white blood cells, platelets, etc., may flow in what may be considered disorganized paths, causing material within the blood to drift upwards or downwards along the primarily straight path. The two-dimensional flow of blood components, as opposed to the straight one-dimensional flow of blood components, may be beneficial for interaction between the blood components and the interior surface of the blood vessel. A density-modifying agent may be able to replicate this non-laminar movement of material through in vivo channels (such as blood vessels) in in vitro channels. It is alleged that components in density-modifying agents, such as beads, colloids, particles of various sizes/shapes etc., simulate the tendency of blood to flow in non-perfect, two-dimensional paths. The benefit of slight-turbulence is that it may increase the interaction of fluid components with the channel surfaces the fluid is in contact with. Accordingly, for the case of fluid flow in Organs-on-Chip, cells, such as immune cells, flowing through the basal microchannel of the chip may better interact with the endothelial cells present at the top of the channel (under the membrane.)

Moreover, regions of alternating hydrophobia and hydrophilicity on the channel surface may also cause disturbed flow patterns as the fluid alternatingly moves towards and away from the channel surfaces, increasing the ability of fluid components to interact with channel surfaces. These alternating regions may be achieved by surface modification with plasma treatment, addition of surfactants, etc. In Organ-on-Chips, the immune cells may be pushed towards channel walls as the fluid containing the cells works to simultaneously avoid areas of hydrophobia and approach areas of hydrophilicity. Both the use of alternating hydrophobic and hydrophilic regions and the use of density-modifying have the ability to increase immune cell recruitment in Organ-on-Chips.

Dilution of Percoll is meant to match closely the specific density of the cells are suspended into it. Several ratios of Percoll/Medium are contemplated. The blood substitute is used for two different types of applications: In the first type of application, it is added to the fluid (i.e. Blood, Serum, Medium) to keep particles/particulates in it dispersed to be in suspension and flowed in a continuously manner. In this application the relative ratio Percoll/Fluid (i.e. Blood, Serum, Medium), which correspond to a specific density can be varied to adapt to the specific particle/particulates in it dispersed. In this application is also contemplated the use of fluorescent dies, antibodies or other detection solution to better image the blood substitute or the particle/particulates suspended into it. In this second type of application is also contemplated the use of fluorescent dyes, antibody or other detection solution to better image the blood substitute. In the second type of application, the blood substitute is flowed into the micro-channel to mimic physiological relevant blood flow shear stresses with the ultimate goal to stimulate the endothelium to fully mature. In this application the relative ratio Percoll/Fluid (i.e. Blood, Serum, Medium) can be varied to adapt the viscosity of the blood substitute to the specific geometry or the specific dimensions of the microchannel and the working range of the pump in use. So that it is possible to have some flexibility in the use of it to achieve the desired shear.

The blood substitute is designed to perfuse different fluid such as blood, plasma and medium; the blood substitute can flow in channels lined with endothelial cells without generating inflammation. In some embodiments, increase viscosity to mimic physiological relevant shear stress at low flow rate. In some embodiments, increase viscosity to keep particles/particulates in suspension. Substitute of Percoll by Ficoll, for one example, could be used in similar or the same method.

However, it was discovered during the development of these inventions, that immune-cell recruitment work has a stronger parallel to in vivo immune-cell recruitment in the presence of a certain range of shear rate in order to produce more physiological results. Additionally, it was discovered that gravity forces also affects the immune cells in microfluidic chips, and in turn, the effectiveness of the recruitment to and into endothelial layers.

Thus, in part, challenges to developing immune recruitment assays with high repeatability and efficiency (little added time for and/or extra steps) involving WBC (white blood cell) adhesion to vascular walls under flow in microfluidic devices was due to the flow generated shear forces, in liquid without a density-modifying reagent, which interfered with immune cell recruitment into inflamed tissue on-chip. This interference was caused in part, by fluid shear forces strong enough for knocking immune cells off of the endothelium while cells are beginning to attach before they attach strongly enough to migrate through the cell layer. Further, gravitational forces were causing many immune cells to move towards or settle onto the bottom of the vascular channel, instead of having more of an opportunity to interact with the endothelial layer on the top of the channel next to the chip membrane that has overlying organ/tissue cells in the upper channel.

III. Contemplated Uses Of A Reagent For Modifying Fluid Viscosity In immune Cell Assays.

Thus, use of media comprising Percoll are contemplated for use in immune cell recruitment, e.g. PBMC recruitment, T cell recruitment, neutrophil recruitment, etc., Thus, in one embodiment, the present invention contemplates immune-cell (e.g. neutrophils, PBMCs, T cells) recruitment. In one preferred embodiment, immune-cell recruitment works best when operating in a certain range of shear rate in order to produce physiological results. In some embodiments, a fluidic platform for the studies of immune cell recruitment and infiltration in the context of acute and chronic inflammation is desired. Such a system would allow, in part, the assessment of the efficacy of drugs, drug discovery, molecular markers, etc. including genetic effects and individual variation in response to drugs, i.e. personalized medicine.

In particular, a system which allows in vitro mimicking the in vivo process of movement of white blood cells out of the circulatory system into organs and tissues would provide a platform for targeting specific steps, such as loose adhesion to the vessel wall (endothelial layer), i.e. capture, fast rolling then slow rolling, followed by firm adhesion (arrest) after which leukocytes migrate through the endothelium called extravasation (alternatively, crawling, transendothelial migration, diapedesis, etc.). Each of these steps involves different sets of adhesion molecules, albeit overlapping, matching ligands and receptors expressed on white blood cells to endothelial cells. The sets of matching ligands and receptors appear to be differentially regulated during inflammation. Adhesion molecules include but are not limited to cell adhesion molecules (CAMS), intercellular adhesion molecules (ICAMs), selectins, integrins, etc. As nonlimiting examples, endothelial cell adhesion molecules include intercellular adhesion molecule-1 (ICAM-1), vascular cell adhesion molecule-1 (VCAM-1), E-selectin, and P-selectin. As nonlimiting examples, leukocyte adhesion molecules include L-selectin. Filippi, "Mechanism of Diapedesis: Importance of the Transcellular Route." Adv Immunol, 129:25-53, 2016.

As one example, integrins (e.g. CD11/CD18, VLA-4) expressed on leukocytes interact with immunoglobulin-like adhesion molecules on endothelial cells (ECs) (e.g., ICAM-1, VCAM-1). The expression of P-selectin, E-selectin ICAM-1, and VCAM-1 on venular EC is typically temporally coordinated during the processes of leukocyte attachment, rolling and firm adhesion/emigration which can occur over several hours after the initiation of an inflammatory response. In fact, deficiencies in one component may result in an altered immune response, as one example, Leukocyte adhesion deficiency (LAD) I is caused by a defect in the β subunit of the integrin molecule, whereas in LAD II, the ligand for the selectin, the sialyl Lewis X is markedly decreased.

FIG. 24A shows a schematic diagram of one embodiment of immune cell recruitment to intestinal mucosa, a hallmark of Inflammatory Bowel Disease, mediated by activation of specific adhesion molecules such as MadCAM-1 and represent a novel therapeutic target.

FIG. 24B shows schematic diagrams of some embodiments of leukocyte extravasation controlled by exemplary sequential adhesive molecules and ligand interactions between leukocytes, endothelial cells, basement membrane, pericytes, and tissue-parenchymal cells. This schema depicts nonlimiting steps and depicts nonlimiting representative adhesive molecules and ligands that are involved at a particular step (shown above the step, i.e. L-Selectin and E/P-Sepectin-PSGL1 for capture and rolling onto endothelial cells). As one example, a neutrophil extravasation cascade involves a sequence of tethering (capture) and rolling along the endothelium, followed by firm adhesion and arrest onto endothelial cells. Subsequently, neutrophils undergo lateral migration or crawling along an endothelial cell layer to find a permissive site, e.g. between cells for transmigration of the endothelial layer. Neutrophils move across the endothelial barrier, either by crawling between or through endothelial cells, then crossing the basement membrane and moving between pericytes (when present) then migrating within interstitial tissues (Nourshargh, Hordijk, & Sixt, 2010; and Filippi, Adv Immunol. 129: 25-53, 2016).

Thus, in preferred embodiments, in-vitro systems of organs or tissue are desired that would employ the use of: organ or tissue specific microvascular endothelial cells (relevant for tissue specific endothelial cell adhesion molecule expression); physiologically relevant fluid flow and shear stress (relevant for immune cells-endothelium interaction). In some embodiments, patient-derived tissue is desired, in part for relevancy of the assessment of donor-donor variability; normal vs diseased state; normal versus inflamed regions, etc., for the studies of immune cells recruitment (e.g. attachment, rolling and arrest) and infiltration (e.g. migration along and through the endothelial cell layer, migration across a basement membrane (including a chip membrane) into tissues. In some embodiments, such studies enable drug discovery and drug efficacy testing. The following nonlimiting embodiments of organs on-chip were developed in part to have these characteristics. Further, the following embodiments may be combined with other embodiments described herein.

Immune cells may be obtained from any one of more sources such as: resident (patient derived), isolated from blood samples (i.e. healthy people and asthmatic patients), primary, cultured, immortal, derived from differentiation procedures, including but not limited to neutrophils, eosinophils, macrophages, monocytes, lymphocytes, innate immune cells, etc.

For non-limiting examples, neutrophil and/or eosinophils are isolated from fresh human blood in one or more ways, for non-limiting examples, using different kits or differential methods of blood separation. In some methods neutrophils/eosinophils are isolated in solution by separating them from the rest of cells by using antibodies specific to certain markers for the unwanted cells that do not exist on neutrophil/eosinophils (i.e. negative selection). As one example, blood cell types are separated from each other by using a gradient of sucrose and thus cells are isolated based on their differences in density. 1992

A. Respiratory Chips: Lung And Small Airways.

Immune recruitment studies on-chips was done with immune cell types including neutrophils; PBMCs; T cells, etc.

In some embodiments, fluids comprising modifying agents as described herein, are contemplated for use in assays associated with immune cell recruitment in respiratory chips, e.g. alveolar lung-on-chip; small airway on-chip; etc.

1. Neutrophil Recruitment In Lung Chip

In some embodiments, fluids comprising modifying agents as described herein, are contemplated for use in assays associated with neutrophil recruitment in lung chips. Some examples of alveolar lung-on-chip are described in U.S. Pat. No. 8,647,861, herein incorporated by reference in its entirety.

FIGS. 11A-C shows an example of one embodiment of an Airway-on-Chip emulating acute asthma exacerbation by combining Rhinovirus infection with IL-13 stimulation in the presence of an exemplary immuno-modulatory compound: Neutrophil recruitment following exacerbation with HRV can be reduced by an exemplary CXCR2 antagonist MK-7123. FIG. 11A (upper image) shows one embodiment of an Airway-on-Chip that enables testing of immuno-modulatory compounds, e.g. for neutrophil recruitment, in a model of acute asthma exacerbation. HRV-16 is represented as small green dots in the upper channel while neutrophil cells (also described as polymorphonuclear leukocytes (PMN)) are represented as large purple spots in the lower channel. An enlarged schematic is demonstrated schematically in the lower image showing a HRV-infected Airway Chip during perfusion in the vascular channel of freshly isolated human neutrophil. FIG. 11B shows a series of fluorescent micrographs showing comparisons of stained neutrophil cells (red) recruited to the endothelium and attached to non-treated cells. Treatments included HRV-16 alone infected cells, IL-13 alone treated cells, HRV-16 and (+) IL-13 treated cells, HRV-16+CXCR2in (inhibitor) treated cells, and HRV-16+IL-13+CXCR2in. Non-stimulated chips are showing limited neutrophil recruitment while HRV infected and IL-13-treated chips show increased neutrophil recruitment. IL-13+HRV induce an additive increase in neutrophil recruitment, while treatment with a CXCR2 antagonist. MK-7123 (10 microM) significantly reduced neutrophil recruitment under three stimulation conditions. FIG. 11C is a graphical comparison showing PMN (neutrophil) cells counts as % of untreated cells and cells treated with combinations shown for IL-13, HRV, and CXCR2 (in) treatments. Quantification of neutrophil recruitment ($p<0.01$; **$p<0.001$).

FIGS. 12A-D shows an example of one embodiment of an Airway-on-Chip demonstrating the effect of a CXCR2 antagonist (inhibitor: in) on neutrophil crawling and transmigration of cells out of the endothelial channel. FIG. 12A is a micrograph showing effects of HRV-16 infected cells (24 hpi) on cell attachment and FIG. 13B shows effects of HRV-16 infected cells (24 hpi) treated with CXCR2in (10 µM) on cell attachment. FIG. 12C shows a graph of the number of spots (i.e. neutrophil cells: N spots) counted over time (up to 300 seconds) for HRV-16 infected cells (24 hpi). FIG. 12D shows a graph of N spots counted over time (up to 600 seconds) for HRV-16 infected cells (24 hpi) treated with CXCR2in (10 µM).

FIGS. 11D-11I show exemplary schematics and data, showing viral-induced exacerbation on-chip inducing neutrophil transmigration, for use in on-chip testing of prophylactic treatments for reducing incidents of severe asthma attacks and for treatments during severe asthma attacks to reduce at least one symptom. FIG. 11D shows an exemplary schematic (as a Venn Diagram) where asthma induction as an inflamed airway is represented by IL-13 treatment (left circle) and viral exacerbation of asthma is represented by a rhinovirus (HRV) infection (right circle). The area of overlap represents asthma exacerbation in a patient or on-chip when both conditions are present. FIG. 11E shows an exemplary schematic of one embodiment of asthma exacerbation where a virus is infecting ciliated epithelial cells in the airway channel (green dots and green ciliated cells) which induces neutrophil (bumpy round cells) recruitment (attachment) and movement through the endothelium on the vascular channel, then as shown in FIG. 11F, neutrophils show extravasation through the porous membrane then into the airway side of the membrane, i.e. trans-epithelial migration. FIG. 11G shows one embodiment of a severe asthma chip enabling neutrophil diapedesis: HRV16 (24 hpi) infected cells visualized by immunofluorescent staining of Myeloperoxidase (MPO) stained neutrophils showing a Z-stack confocal microscopic image. FIG. 11H shows a colorized immunofluorescent image of HRV16 (24 hpi) infected cells stained with Myeloperoxidase (MPO) (green)/ mAbJ2 (red)/DAPI (blue) where MPO+ cells are located near virally infected cells. And FIG. 11I shows a monoclonal antibody (mabJ2) (mouse) detecting double-strand RNA as an RNA replication-center assay for one embodiment of a high content image-based quantification of human rhinovirus and Coxsackie virus infections.

2. Neutrophil Recruitment In Small Airway Chip

In some embodiments, fluids comprising modifying agents as described herein, are contemplated for use in assays associated with neutrophil recruitment in small airway chips. Small-airway Lung On-Chip include but are not limited to (COPD; asthma, etc.

Examples of small-airway Lung On-Chip include but are not limited to (COPD/asthma Benam, et al., "Small airway-on-a-chip enables analysis of human lung inflammation and drug responses in vitro._" Nature Methods, online pages 1-7, online methods and Supplementary (2015), For instance, a "small airway-on-a-chip" recapitulates the human bronchial and bronchiolar epithelium by supporting the full differentiation of a columnar, pseudostratified, mucociliary, bronchiolar epithelium composed of human primary airway epithelial cells isolated from normal or diseased patients. The epithelium may be underlined by a functional human pulmonary microvascular endothelium experiencing continuous fluid flow. Human airway cells are cultured on-chip with an air liquid interface (ALI) for three weeks for providing an in vivo-like epithelium composed of multi-ciliated cells, with physiological cilia beating frequency, as well as goblet cells secreting mucus into the lumen resulting in robust mucociliary clearance.

Example A—Differentiating Stem Cells into Lung Cells On-Chip

Exemplary stem cells for use in seeding chips include but are not limited to stem cell sources described herein, including organoids derived (i.e. created) starting from one or more cell types, including but not limited to primary lung tissues, primary cells; stem cells; embryonic stem cells (ESCs); or induced pluripotent stem cells (iPS cells), or other cells as described herein. iPSC organoids may be known as tracheospheres, bronchospheres, and pneumospheres (or alveolospheres), etc., according to the lung or respiratory tissue they most closely represent.

As another example, a microfluidic chip as described herein, may be seeded by cells that were partially differentiated, i.e. not yet terminally differentiated, e.g. as one or more populations comprising SOX17+/FOXA2+, SOX2+/ FOXA2+, NKX2-1+, SOX9+ distal progenitor cells, etc., for undergoing further differentiation stages on-chip, resulting in terminally differentiated stem cell based alveolar lung-on-chip. As another example, a microfluidic chip as described herein, may be seeded by cells that were partially differentiated, i.e. not yet terminally differentiated, e.g. as one or more cell populations comprising SOX17+/FOXA2+ cells, SOX2+/FOXA2+ cells, NKX2-1+ cells, SOX2+ proximal progenitor cells, etc., for undergoing further differentiation stages on-chip, resulting in terminally differentiated stem cell based small-airway-on-chip. Such stem cell based small-airway-on-chip may include basal cells; club cells; ciliated cells; goblet cells, etc.

As another example, a microfluidic chip as described herein, may be seeded with a population of stem cells, such as any one or more populations described herein, e.g. iPS cells, EPS cells, etc. As an exemplary protocol, such stem cells may be treated with factors for inducing SOX17+/ FOXA2+ cells, SOX2+/FOXA2+ cells, NKX2-1+ cells, then either inducing a predominant distal progenitor cells, e.g. SOX9+ or proximal progenitor cells, e.g.SOX2+ for undergoing terminal differentiation into alveolar cells or bronchial/tracheal cells, respectively.

As another example, a microfluidic chip as described herein and in cited publications herein incorporated by reference, may be seeded with organoids capable of differentiating into respiratory cells, lung cells, etc. In one contemplative embodiment, organoids seeded into chips may be whole, e.g. as lifted off of the tissue culture surface. In another contemplative embodiment, organoids seeded into chips may be partial, e.g. lifted off of the tissue culture surface then mechanically disrupted (e.g. vortexed), for seeding organoids as pieces. In yet other embodiments, organoids may be disrupted or sorted into single cells suspensions, e.g. filtering, flow cytometry sorting for specific markers, such as one or more of SOX2+/FOXA2+ cells, NKX2-1+ cells, SOX2+ proximal progenitor cells, etc., for seeding onto stem cell based microfluidic lung chips.

In yet other embodiments, a microfluidic chip as described herein and in cited publications herein incorporated by reference, may be used to generate lung organoids for use herein either to further differentiate on-chip or for harvesting for use in seeding a microfluidic chip as described herein for providing a stem cell based lung-onchip. In particular, in some embodiments, lung organoids derived from starting iPS cells involved a last stage air-liquid interphase culture that may be induced on-chip (for an example of one protocol that may be used on-chip (for e.g. see, Wong, A. P., Bear, C. E., Chin, S., Pasceri, P., Thompson, T. O., Huan, L. J., Ratjen, F., Ellis, J., and Rossant, J. (2012). "Directed differentiation of human pluripotent stem cells into mature airway epithelia expressing functional CFTR protein." Nat. Biotechnol. 30, 876-882), herein incorporated by reference.

In yet other embodiments, such microfluidic organoid cultures on-chips may be used for assays to screen for factors controlling generation of a particular cell type, such as alveolar type 1 vs. type II, multiciliated cells vs. percentages of secretory and basal cells.

In some embodiments, human ESC are treated with Activin A and WNT3a for 4 days then seeded onto collagen Type IV matrix in tissue culture plates. This method is known to generate stable and reproducible definitive endoderm progenitor cells with >85% of the cells co-expressing CXCR4 and CD117 (cKit). The majority of the cells also co-stained for SOX17 and FOXA2. See, Wong, et al 2012. In some embodiments, cells generated with this method may instead be transferred to microfluidic devices as described herein, for subsequent additions of differentiation and maturation agents on-chips having collagen Type IV matrix coated membranes.

In some embodiments, adding high levels of FGF2 coupled with adding SHH for an additional 5 days may be used to induce definitive endoderm cells (such as SOX17+ cells) into lung progenitor (NKX2.1-expressing) cell fate. In some embodiments, after addition of FGF2 and SHH, expression of definitive endoderm marker SOX17 was down-regulated. In some embodiments, after addition of FGF2 and SHH, there may be up-regulation of anterior foregut endoderm transcription factors SOX2 and NKX2.1+. In some embodiments, progenitor cells express NKX2.1+ FOXA2+ and EpCAM. Progenitor cells obtained with this method are referred to as embryonic lung progenitors.

In some embodiments, adding FGF7 (50 ng/ml) and FGF10 (50 ng/ml) may increase expression of lung endoderm NKX2.1 and FOXA2 gene expression from embryonic lung progenitors.

Immune cells may be obtained from any one of more sources such as: resident (patient derived), isolated from blood samples (i.e. healthy people and asthmatic patients), primary, cultured, immortal, derived from differentiation procedures, including but not limited to neutrophils, eosinophils, macrophages, monocytes, lymphocytes, innate immune cells, etc.

For non-limiting examples, neutrophil and/or eosinophils are isolated from fresh human blood in one or more ways, for non-limiting examples, using different kits or differential methods of blood separation. In some methods neutrophils/eosinophils are isolated in solution by separating them from the rest of cells by using antibodies specific to certain markers for the unwanted cells that do not exist on neutrophil/eosinophils (i.e. negative selection). As one example, blood cell types are separated from each other by using a gradient of sucrose and thus cells are isolated based on their differences in density. 1992.

Perfusion of T-cells through the vascular channel with IL-13 to mimic a microenvironment enriched with inflammatory Type 2 T helper (Th2) cells resulted in significant airway remodeling with goblet cells hyperplasia, increase of pro-inflammatory cytokines, and reduction of cilia beating frequency. This phenotype was suppressed following incubation with Tofacitinib, a Jak inhibitor used as a therapeutic against rheumatoid arthritis.

Using primary airway cells derived from COPD patients, the small-airway-on-a-chip was also leveraged to investigate exacerbations in COPD, and to measure human neutrophil recruitment to the activated endothelium following epithelial exposure to pro-inflammatory stimuli. In addition, because the small-airway-on-a-chip has a separate air channel, it is possible to circulate air-borne pollutants through the epithelial chamber and evaluate, for example, the response of epithelial cells to cigarette smoke.

Contemplated application of a human Lung-on-Chip (e.g. using stem-cell based lung cells) include but are not limited to a range of diseases such as cystic fibrosis, congenital pediatric lung diseases, inflammatory diseases of the lung, pulmonary fibrosis, lung cancer, pulmonary infectious disease, in addition to emphysema, bronchitis, asthma, severe asthma, chronic bronchitis, etc.

As one example, Chronic obstructive lung disease (COPD) and asthma are the most prevalent of all chronic respiratory diseases worldwide, and they rank among the top 20 conditions causing disability globally. Both conditions engender respiratory distress and chronic inflammation of the lung and are thought to result from environmental exposure in genetically susceptible individuals. The symptoms can be further exacerbated by airborne particles, or viral and bacterial infection of the airways. Currently, there are limited treatment options for severe asthma and COPD, partly because of the lack of suitable preclinical model systems for dissecting the contributions and temporal dependencies between environmental factors, genetic predispositions, and acquired susceptibility. In fact, animal models do not naturally develop asthma, and even when they can be rendered sensitive to antigens, they fail to recapitulate all aspects of the human pathogenesis. This is likely due to well-known differences in airways physiology, anatomy and immunology a between animals and humans. For instance, secretory goblet cells are overabundant in COPD and asthmatic airways; this pathological hyperplasia is possibly mediated by Notch signaling-directing differentiation of basal cells, the stem cells of the large airway, towards a secretory fate. Mice, however, exhibit a much lower abundance of goblet cells than humans and therefore do not provide a good model for development and homeostasis of goblet cells in healthy and diseased human lungs. Further, whereas the role of inflammation and the innate immune system in asthma is well known, the spatiotemporal dynamics of this process cannot easily be studied in animal systems. Also, the origin of pathological inflammatory responses might be found in developmental events that are human or even patient-specific, such as in utero fetal programming of gene expression involved in lung development, or signaling from the microbiome during a responsive postnatal time window thought to promote immune tolerance. Human primary cell 3D models of the airways have demonstrated a new avenue towards addressing these and other questions in vitro. In the future, human stem-cell based lung chip models that support the dynamic interaction with circulating immune cells, essential in asthma and COPD pathogenesis, could help elucidate the underlying inflammatory mechanisms, model exacerbation in vitro and lead to the development of new therapies and identify new treatment options.

B. Intestine Chips.

Several different Organ On-Chips were used with neutrophils, including but not limited to Caco2 Intestine On-Chip and enteroid-derived Intestine On-Chip.

1. T Cell Recruitment In Intestine Chip

In some embodiments, fluids comprising modifying agents as described herein, are contemplated for use in assays associated with T cell recruitment assays in Intestine Chips.

FIG. 16 shows an exemplary schematic representation of one embodiment of a microfluidic chip: 1. Epithelial Channel; 2. Vascular Channel; 3. Human Primary Intestinal Epithelial Cells; 4. Human Intestinal Microvascular Endothelial Cells (HIMEC) or iHIMEC, etc.); 5. Membrane; and 6. Vacuum Channels.

FIG. 17 shows an exemplary schematic representation along with representative photographs and micrographs for preparing one embodiment of a microfluidic Intestine-on-Chip where methods of (left to right) tissue isolation and processing; expansion & banking provide cells used to seed: Top channel—Intestinal epithelial cells forming an epithelium and Bottom channel—Intestinal microvascular endothelium (HIMEC) incubated (organ maintenance) under constant flow and certain membrane stretch conditions. Prior to cell seeding, the chip membrane was surface activated then ECM coated. Lower images show morphology by phase contrast microscopy of the epithelial cell layer exposed to flow over time (left 3 images) compared to the same time period, 12 days of incubation, under static culture (right image). Thus, in this co-culture setup we observed the spontaneous 3D villa formation that doesn't occur in the static culture. We have successfully maintained this microfluidic co-cultures for over 3 wk with no loss of phenotype.

2. PBMC Recruitment In Intestine Chip

In some embodiments, fluids comprising modifying agents as described herein, are contemplated for use in assays associated with peripheral blood mononuclear cell (PBMC) recruitment assays in Intestine Chips.

FIGS. 19A-D shows exemplary florescent microscope images, focused on the endothelial plane, showing green labeled PBMC (peripheral mononuclear blood cells) (each green dot represents one cell) attachment to inflamed endothelium, under liquid flow where the liquid contained FIG. 19A 0% Percoll, FIG. 19B 25% Percoll, FIG. 19C 50% Percoll, and FIG. 19D 80% Percoll, demonstrating that increased media viscosity improves immune cells recruitment. Addition of Percoll increases media viscosity and improves immune cells-endothelium interaction at 50% Percoll where a clear cell attachment was seen (numerous green dots). Fifty percent (50%) Percoll also showed the highest number of immune cell recruitment to inflamed endothelium. Therefore, increased media viscosity is achieved by addition of Percoll, where Percoll consists of colloidal silica particles of 15-30 nm diameter coated with polyvinylpyrrolidone (PVP). Furthermore, an increase shear allows immune cells to interact with endothelial cells.

FIGS. 20A-C shows embodiments of an intestine on chip emulating immune cell recruitment on-Chip through providing physiological level of shear and fluid viscosity to emulate immune cell recruitment at epithelial-endothelial tissue interfaces. Embodiments of intestine on chip showing a florescent micrograph of stained cells FIG. 20A under non-physiological shear in vascular channel and non-physiological fluid viscosity. FIG. 20B under physiological shear in vascular channel and physiological fluid viscosity. PBMCs (green) and inflamed HIMEC (red). FIG. 20C shows flow directions (arrows) on a chip schematic. Scale bar=100 micrometers. Physiological levels of shear and fluid viscosity emulate immune cell recruitment at the epithelial-endothelial (tissue-tissue) interface.

FIGS. 21A-B shows that a change in the media viscosity does not affect the expression of adhesion molecules on endothelial cells (vascular compartment) on-chip.

FIG. 21A chart showing relative mRNA expression between standard media (left, grey bars), viscous media (50% Percoll) (blue, middle bars) and inflammatory inducing media containing Cytomix cytokines (right, pink bars), after 24 hours of treatment.

FIG. 21B showing micrographs of cells (left) corresponding to lower power micrographs of the channels (right). Stained ICAM-1 (pink) and nuclei (blue). Upper is a control intestine on-chip, middle is an inflamed intestine on-chip and lower is a chip treated with viscous media, 50% Percoll, intestine on-chip.

FIGS. 22A-B shows exemplary florescent microscope images and graphs demonstrating induction of adhesion molecule expression in intestinal endothelial cells on-chip after induction of inflammation using clinically relevant levels of cytokines. FIG. 22A ICAM-1 (pink) and nuclei (blue) stained channels (left) and under higher magnification (right) for control (upper) and inflamed (lower) channels. FIG. 22B shows a graphical comparison of relative mRNA expression for E-selectin, VCAM1, MadCAM1 and ICAM-1. Cells on-chip were treated for 24 hours with a Cytomix Formulation: TNF-alpha 10 U/ml (approximately 215 pg/ml), IL-1 beta approximately 50 U/ml (approximately 50 pg/ml), IL-6 20 U/ml (approximately 200 pg/ml). U=units.

FIGS. 23A-C shows one embodiment of immune cell recruitment in a microfluidic chip contemplated for use with a fluid-modifying reagent, e.g. an inflamed intestine on-chip where PBMCs were suspended in a 50% Percoll fluid flowing through the chip. FIG. 23A shows one embodiment of a microfluidic chip where PBMCS or other white blood cell populations may be added in the lower channel (thick arrow) or added mid-channel on either side, see thin arrows). FIG. 23B shows exemplary results in a viewing area on-chip where the channel area shown is delineated by dotted lines in FIG. 23A). Far left FIG. 23B panel shows a control intestine on-chip with no PBMCs, hence no dots. Middle panel shows a non-inflamed intestine on-chip with PBMCs attached to the endothelium as scattered dots. Far right shows an inflamed intestine on-chip with PBMCs as numerous scattered dots attached to the endothelium (see inflammation induction methods). FIG. 23C shows a graph comparing PBMC recruitment to the endothelial layer between controls; non-inflamed and inflamed endothelium.

3. PBMC Recruitment with T-cell Pre-Activation in Intestine Chip

In some embodiments, an Intestine on-Chip using Caco-2 epithelial cells was used for testing parameters using PBMCs treated, prior to the addition to chips, with T-cell activating compounds. In particular, experiments were evaluated for parameters including but not limited to: assessing T-cell recruitment; assessing activated T-cell migration through an ECM sandwich layer; assessing impact of endothelial component on T-cell activation and recruitment;

quantifying T-cell activation by loss of barrier function, immunofluorescence analysis, and cytokine induction; etc.

a. Example B—Exemplary Steps for Testing Parameters Using PBMCs Treated with T-Cell Activating Compounds FIG. 26 shows a schematic of an exemplary timeline for assessing T-cell recruitment in Caco-2 Intestine on-Chip. Exemplary Chip Set-up: Day 0—Seed Chips Compartment: Caco-2 (Top)+/− HIMEC (Bottom); see exemplary Table 1. Day 1—Connect to Flow. Day 6—Treatment: see exemplary Table 3. Day 7—Flow PBMC Exemplary Readouts: Permeability; Morphology; etc. Day 8—Terminate Experiment: Exemplary Readouts: Permeability; Morphology; Immunofluorescence; Cytokine profile; LDH, etc.

Exemplary embodiments include: Day 1: Made media for the entire experiment in one batch at beginning of flow.; Day 7: PBMCs: treated with CD3/CD28 on plate for 4 hours, then flowed through chip for 20 minutes at 30 μL/hr using 50% Percoll solution (treatment from Day 6 removed from basal media).; 3. After flowing PBMCs, Chips left static for 40 minutes.; and Day 7: MCP1/TNF-α/IL-1β treatments added to apical Chip media (TNF-α/IL-1β also added to basal media day 7 until PBMC flow), continued until day 8 in apical media.

TABLE 1

Exemplary cell types for seeding Intestine On-Chips.

| Cell Type | Donor/Passage | Viability | Total # Cells |
|---|---|---|---|
| HIMEC | P7, from MK | 75% | 2.25 million |
| Caco2 | — | 87% | 15 million |
| PBMCs | Donor | — | — |

TABLE 2

Exemplary Intestine-Chip Immune Recruitment Assays.

| Exemplary Conditions | |
|---|---|
| Flow rate | 30 uL/hr |
| Stretch | None |
| ECM | Matrigel +/− MCP1 |
| Top Media | DMEM, 10% FBS, Penicillin/Streptomycin, Phenol Red, 4.5 g/mL Glucose, Glutam Pyruvate, 20 ug/mL Lucifer Yellow |
| Bottom Media | EGM-2 MV Complete, 5% FBS, No Gentamicin, Penicillin/Streptomycin |

TABLE 3

Exemplary Experimental Conditions for Intestine On-Chips, at least 3 duplicate chips.

| Basal | Treatment | T Cells |
|---|---|---|
| G1;- | MCP1 + TNF-α/IL-1β | (+/+) CD3/CD28 |
| G2; HIMEC | MCP1 + TNF-α/IL-1β | (+/+) CD3/CD28 |
| G3; HIMEC | MCP1 + TNF-α/IL-1β | (+/−) CD3/CD28 |
| G4; HIMEC | MCP1 + TNF-α/IL-1β | (−/−) CD3/CD28 |
| G5; HIMEC | MCP1 | (+/+) CD3/CD28 |

TABLE 3-continued

Exemplary Experimental Conditions for Intestine On-Chips, at least 3 duplicate chips.

| Basal | Treatment | T Cells |
|---|---|---|
| G6; HIMEC | No MCP1 in ECM + TNF-α/IL-1β | (+/+) CD3/CD28 |
| G7; HIMEC | TNF-α/IL-1β | (+/+) CD3/CD28 |
| G8; HIMEC | — | (+/−) CD3/CD28 |

TABLE 4

Exemplary PBMC Flow Parameters.

| Exemplary Flow Parameters | |
|---|---|
| Goal number of cells flowed through chip | — |
| Seeding density | — |
| Media-Percoll solution | 50% Percoll, 50% apical media |
| Flow rate (Set) | 355 uL/hr |
| Flow rate (Actual) | 300 uL/hr |
| Time length of PBMC flow | 20 minutes |
| Time length of static interval | 40 minutes |
| Time length of post-PBMC flow | — |

TABLE 5

Exemplary Readouts/Endpoints form at least 3 duplicate chips.

| Readouts captured from each of at least 3 duplicate chips | Cytokines-50 uL of captured outflow Barrier Function- |
|---|---|
| Chip 1 | LDH/RNA |
| Chip 2 | Fix for IF (immunofluorescence) |
| Chip 3 | Fix for IF (immunofluorescence) |

TABLE 6

Exemplary PCR Primers for BioMarkers in Epithelium and Endothelium.

| Primer Spot | Epithelium | Endothelium |
|---|---|---|
| 1 | Metalloreductase STEAP1 (six transmembrane epithelial antigen of the prostate 1) | Metalloreductase STEAP I |
| 2 | LGR5 | GATA3 |
| 3 | IL-6 | MADCAM |
| 4 | IL-8 | PECAM |
| 5 | IFN-gamma | VECAM |
| 6 | Occludin | TBP (TATA-Box-Binding Protein) |
| 7 | TBP (TATA-Box-Binding P) | GAPDH |
| 8 | 18S/GAPDH | 18S |

TABLE 7

Exemplary Antibodies For Immunostaining Analysis.

| Chip Type | Primary Antibodies | Secondary Antibodies |
|---|---|---|
| Half chip | Anti-CD3 STEAP1 | 647 488 Zo-1-594 DAPI |

TABLE 7-continued

Exemplary Antibodies For Immunostaining Analysis.

| Chip Type | Primary Antibodies | Secondary Antibodies |
|---|---|---|
| Slice 1 | Anti-CD3 | 488 |
|  | Anti-Ecadherin | Anti-Rb 568 |
|  | Anti-CD69 | 647 |
|  |  | DAPI |
| Slice 2 | — | 488 |
|  |  | 568 |
|  |  | 647 |
| (Slice 3, optional) | Anti-CD3 | 488 |
|  | Phalloidin | 568 |
|  | Anti-CD69 | 647 |
|  |  | DAPI |
| (Slice 4, optional) | Anti-CD3 | 488 |
|  | Anti-Occludin | Anti-Rb 568 |
|  | Anti-CD69 | 647 |
|  |  | DAPI | b. Exemplary Results of Intestine-Chip Immune Recruitment Assays

In general, anti-CD3/anti-CD28 co-stimulation prior to adding chips was found to increase the recruitment of PBMCs to the epithelial channel. Surprisingly, the presence of HIMEC endothelium decreases the numbers of PBMCs recruited to the epithelial layer. The inclusion of Percoll in the basal channel facilitates immune recruitment of Intestine-Chip incubated within an incubation pod.

FIG. 27A-D shows exemplary inclusion of Percoll in the basal channel facilitates immune recruitment of Intestine-Chip in the Zoe™ Culture Module. DAPI (dark blue nuclei) and PBMCs (colored light blue). Blue arrow across the panels at the top represents decreasing Numbers of Immune Cells Recruited to the Intestine-Chip Epithelial Channel. FIG. 27A shows epithelial cells without HIMECs treated with anti-CD3/anti-CD28 and TNF-α/IL-1β/MCP-1. FIG. 27B shows epithelial cells with HIMECs treated with anti-CD3/anti-CD28 and TNF-α/IL-1β/MCP-1. FIG. 27C shows epithelial cells with HIMECs treated with anti-CD3 and TNF-α/IL-1β/MCP-1. FIG. 27D shows no epithelial cells present with HIMECs treated with TNF-α/IL-1β/MCP-1.

4. PBMC Recruitment with T-cell Pre-Activation In Intestine Chip: Assessing PBMC Pre-Activation Conditions in the Presence of Percoll In one embodiment, conditions were tested for inducing minimal PBMC pre-activation prior to adding PMBCs to chips. In some embodiments, preactivation is measured as CD69 induction.

Exemplary preactivation conditions: 1 million/mL PBMCs on plates treated (incubated) for 2 hours with control or anti-CD3 & anti-CD28 (2 ug/mL each). In some embodiments, anti-CD3 & anti-CD28 were bound to plates (antibody solution incubated in plates then washed off prior to adding cells), in other embodiments anti-CD3 & anti-CD28 was provided as a solution along with cells. In some embodiments, Percoll was added in solution prior to incubation.

Exemplary results demonstrated: Control PBMCs (isotype antibody controls) were not appreciably CD69+; unbound (in solution) versus plate bound anti-CD3/anti-CD28 treatments activated 30% and 50% of the PBMC population, respectively; and Percoll had a negligible effect on PBMC activation Exemplary CD69+Flow-Cytometry (FACs) Assay: CD69+FACs assay was used o assess PBMC activation on plates and test for Percoll effects on the activation state of PBMCs.

FIG. 28A-B shows exemplary assessing PBMC Activation for assessing PBMC Pre-activation. CD69+Flow-Cytometry (FACs) Assay. FIG. 28A shows exemplary FACS analysis of CD69 stained cells without using Percoll. FIG. 28B shows exemplary FACS analysis of CD69 stained cells using Percoll.

Exemplary Timeline (Hours) for Assessing PBMC Pre-Activation

−4 hours—Plate-bind CD3, see Conditions Table.
0 hours—Plate PBMCs Add treatments.
After 2 hours—Takedown: evaluate endpoints: FACs (CD69); Cytokines; etc.

TABLE 8

Exemplary PBMC Pre-activation conditions.

|   | PBMC Density (mill/mL) | Treatment | # Wells | # Chips |
|---|---|---|---|---|
| 1 | 1 | — | 3 | n/a |
| 2 |   | + CD3 + CD28 | 3 |   |
| 3 | 5 | — | 3 | n/a |
| 4 |   | + CD3 + CD28 | 3 |   |
| 5 | 10 | — | 3 | n/a |
| 6 |   | + CD3 + CD28 | 3 |   |
| 7 | 15 | — | 3 | 3 |
| 8 |   | + CD3 + CD28 | 3 | 3 |
| 9 | 5; NO PERCOLL | — | 3 | n/a |
|   |   | + CD3 + CD28 | 3 |   |

5. PBMC Recruitment with T-Cell Pre-Activation In Intestine Chip: Providing an ECM Sandwich Layer In one embodiment, methods were developed in order to polymerize gels as an ECM sandwich layer. In one embodiment, Collagen (Col) I ECM gels were tested on Intestine-Chips as part of an ECM sandwich layer, i.e. coating the endothelial channel including the vascular dies of the membrane. Thus, vascular side membrane coating in addition to the coating on the epithelial side of the membrane provides a sandwich ECM.

Collagen I ECM Optimization: Exemplary timeline (hours) for assessing Collagen I Extra Cellular Matrix, at least 3 chips. 0 hours—Chip Coating for at least 3 duplicate chips, see Conditions Table 9. 0.5 hours—Chip #1 Takedown: evaluate endpoints: Confocal imaging; etc. 0.75 hours—Chip #2 Takedown: evaluate endpoints: Confocal imaging; etc. Chip #3 after 16 hours from time 0: Takedown: evaluate endpoints: Confocal imaging; etc.

In one additional embodiment, Col 1 gels were doped with 0.4 um microbeads, i.e. microbeads were added to gels prior to solidification on-chip.

In contrast to using manual deposition of Col 1 at 2 mg/mL or using Col 1 at 1 mg/ml, a negligible amount of Collagen I was observed to be deposited on the vascular side of the membrane when using a syringe pump at 2 mg/mL.

FIG. 29A-E shows exemplary results of Collagen I Extra Cellular Matrix. FIG. 29A shows results of 2 mg/mL Collagen 1 gel; 45 min (0.75 hr.)×25° C.; Syringe Pump. FIG. 29B shows results of 2 mg/mL Collagen 1 gel; 30 min (0.5 hr.)×37° C.; Manual. FIG. 29C shows results of 1 mg/mL Collagen 1 gel; 16 hr×4° C.; Syringe Pump. FIG. 29D shows results of 1 mg/mL Collagen 1 gel; 45 min×25° C.; Syringe Pump. FIG. 29E 1 mg/mL; 30 min×37° C.; Syringe Pump.

TABLE 9

Exemplary Collagen I Extra Cellular Matrix Optimization.

| | Concentration (mg/mL) | Incubation Time (hr) | Polymerization Temperature (° C-Celsius) | # Chips |
|---|---|---|---|---|
| 1 | 1 | 0.5 | 37 | 1 |
| 2 | | 0.75 | 25 | 1 |
| 3 | | (syringe pump) | | |
| 4 | | | | |
| 5 | 2 | 0.5 | 37 | 1 |
| 6 | phase 1 ECM | 0.75 | 25 | 1 |
| 7 | concentration | (syringe pump) | 4 | 1 |
| 8 | | Overnight | | |

In some embodiments, a fluidic device comprising fluid modifying agent is used for immune cell assays for using a bi-specific antibody for treating an inflammatory condition, a cancer cell, etc. FIG. 42 shows exemplary assessing Early Activation of Peripheral Immune Cells. Pre-incubated PBMCs to be circulated through the vascular channel of the Intestine-Chip were assessed for the early activation marker CD69. CD69 levels are similar in all cases except the anti-CD3/anti-CD28 positive control. Thus CD3 binding without co-binding of the tumor target by the TCBs on the Intestine-Chip does not activate the immune cell population.

C. Immune Cell Recruitment In Additional Types of Chips.

1. PBMC Recruitment In Liver Chips

In some embodiments, fluids comprising modifying agents as described herein, are contemplated for use in assays associated with recruitment of immune cells, such as peripheral blood mononuclear cells (PBMC); mononuclear white blood cells; macrophage cells; Kupffer Cells; etc., in Liver Chips.

Some examples of a liver on-chip are described in PCT/US2016/064795 published as WO2017096282 (Jun. 8, 2017) "Devices and methods for simulating a function of a liver tissue", herein incorporated by reference in its entirety. In some embodiments, hepatocytes are located in one channel with another channel as a vascular channel comprising endothelial cells, such as Liver Sinusoidal Endothelial Cells ("LSEC").

2. PBMC Recruitment In Skin Chip

In some embodiments, fluids comprising modifying agents as described herein, are contemplated for use in assays associated with recruitment of immune cells, such as peripheral blood mononuclear cells (PBMC); mononuclear white blood cells; macrophage cells; etc., in Skin Chips.

FIG. 7A-D shows schematic drawings and exemplary micrographs of cell growing in an exemplary open top chip. In one embodiment, a skin on-chip is an exemplary open top chip. FIG. 7A shows a schematic of one embodiment of an open top chip. FIG. 7B shows a side view schematic as a cross section of one embodiment of an open top chip. FIG. 7C shows a schematic of one embodiment of a lower circular channel simulating a blood vessel located in the bottom of the chip. FIG. 7D shows a schematic of one embodiment of an open top chip comprising a keratinocyte layer in the top fluidic channel (micrograph of keratinocyte layer on the upper left) and a lower dermal area underneath (micrograph of growing cells in the dermal area (layer) on the lower left).

3. PBMC Recruitment In Cancer Chip

In some embodiments, fluids comprising modifying agents as described herein, are contemplated for use in assays associated with recruitment of immune cells, such as peripheral blood mononuclear cells (PBMC); mononuclear white blood cells; macrophage cells; etc., in Cancer Chips.

FIGS. 14A-D shows exemplary embodiments for linking together microfluidic chips contemplated for use with fluids comprising reagents.

FIG. 14A shows an exemplary schematic illustration of one embodiment for providing a Tumor-On-Chip (Tumor On-Chip or Cancer On-Chip) and one embodiment for incorporation of a tumor microenvironment. On the left, a schematic illustration shows one embodiment of a microfluidic Tumor-On-Chip (16), having two microfluidic channels (1), with an upper channel port (2) and lower channel port (3), with optionally used vacuum chambers (4). On the right, a schematic illustration shows one embodiment of a microfluidic Tumor-On-Chip with four cell types, in the upper channel, tumor cells and epithelial cells on top of a stromal cell layer separated by a chip membrane from the lower channel with endothelial cells. Immune cells (white) are added to chips in the lower vascular channel (shown) and/or immune cells are added to the upper channel.

FIG. 14B shows an exemplary schematic illustration of one embodiment for providing a Cancer-Chip (Cancer-On-Chip) linked to a Bone-Marrow Chip.

FIG. 14C shows an exemplary schematic illustration of a Cancer-Chip (Cancer-On-Chip) linked to a Lymph Chip (Lymph Node-on-chip).

FIG. 14D shows an exemplary schematic illustration for providing a Metastasis-Chip (System) for one embodiment, a Cancer-Chip (Cancer-On-Chip) linked to a Lymph Chip (Lymph Node-on-chip) with at least one additional Organ-chip fluidically attached to the Lymph Chip. In one embodiment, there is an incorporation of a vascular component the Lymph Chip.

C. Exemplary Embodiments Related To Application Of And Discovery of Immune-Modulating Therapies.

In other preferred embodiments, using microfluidic chips comprising fluid modifying reagents are contemplated for use in relation to immune-modulating therapies (e.g. immunoncology). Immune recruitment studies was done with various cell types including neutrophils (U.S. Pat. No. '861), PBMCs; T cells, etc., in a number of different Organ-Chips, including alveolar Lung-Chip U.S. Pat. No. '861), small-airway Lung-Chip (COPD/asthma paper, see reference herein), Caco2 Intestine-Chip, and enteroid-derived Intestine-Chip, etc.

Thus, embodiments include using microfluidic chips in combination with fluids comprising modifying reagents for use in testing compounds, for example, known therapeutic compounds, testing for new therapeutic compounds, such as immunomdulatory compounds, including but not limited to compounds for use as biomarkers, for use in immunoncology, for use in individualized medicine, etc.

D. Immune Cell Movement Through and Over Parenchymal Cells.

As discussed above, a fluid-modifying agent, such as Percoll, was used to enhance immune cell recruitment and movement into endothelial cell layers. Related immune cell activities include moving from endothelium and into basal areas of parenchymal cell layers; moving through a parenchymal cell layer (e.g. horizontally between or within cells); moving through a parenchymal cell layer (e.g. vertically between or within cells); moving out of parenchymal cell layers on their apical side. Another immune cell activity is moving over the upper surface of an epithelial layer lining a body cavity, e.g. within a mucosal layer, such as an intestinal epithelial layer, a bronchial cell layer, an alveolar cell layer, etc. Therefore, additional uses of fluids containing a modifying agent are contemplated to provide mucosal fluid mimics. Thus, in some embodiments, a fluid-modifying agent is provided for mimicking mucosal fluids, including but not limited to intestinal mucosal fluids, bronchial mucosal fluids, alveolar mucosal fluids, reproductive organ mucosal fluids, etc.

IV. A Modified Fluid For Use As A Blood Substitute.

In some embodiments, fluidic devices are contemplated for use with a fluid comprising a modifying agent as a blood substitute, as described herein, e.g. exemplary cancer on-chips, including but not limited to those described in PCT/US2017/024988 published as WO2017173066 (Oct. 5, 2017) "Devices, systems and methods for inhibiting invasion and metastasis of cancer", herein incorporated by reference in its entirety;

In some embodiments, microfluidic devices are contemplated for use with a fluid substitute, e.g. a blood substitute, as described herein, with exemplary chips such as described in PCT/US2016/033686 published as WO2016191332 (Dec. 1, 2016), herein incorporated by reference in its entirety. In some embodiments, microfluidic devices are contemplated for use with a fluid substitute, e.g. a blood substitute, as described herein, with exemplary chip geometries as shown in part in PCT Application filed 2017, herein incorporated by reference in its entirety.

In some embodiments, a blood substitute comprising a fluid-modifying agent is used in a fluidic device comprising additive channels. In some embodiments, a fluid-modifying agent is added to blood. n some embodiments, a fluid-modifying agent is added to serum. In some embodiments, a fluid-modifying agent is added along with an additive agent.

FIG. 14 demonstrates one contemplated embodiment of fluidic device or chip (1900) having an anticoagulant ports (1932 and 1934) for use with a fluid-modifying gent, such as a blood substitute. Shown is a schematic of one embodiment of a microfluidic device, as in FIG. 9A, with the addition of an anticoagulant ports as additive channels (1932 and 1934 surrounding the OUTLET port 1917) (one on either side near at least one inlet or outlet port for which effluent anti-coagulation is desired). Arrows pointing to INLET ports 1910 and 1911 for upper and lower channels while other arrows point to OUTLET ports 1917 and 1915, respectively attached to inlet ports. The upper channel 1912 emerges from one INLET 1910. The lower channel 1914 emerges from underneath the upper channel attached to the lower Inlet 1911. Each of two microchannels terminates at a single port. Each microchannel attached to an anticoagulant port is in fluidic communication with two additive channels, each pair of additive channel connecting to a separate port (e.g. for adding the additive to the additive channel, i.e. ANTI-COAGULANT port 1930), attached to the top microfluidic channel where the upper channel is also marked with an OUTLET at one end. In other embodiments, the lower vascular chamber has an anticoagulant port near the vascular outlet. An arrow points to the IMAGING area (active region) 1920 outlined with dotted lines.

A. Using Fluid Modifying Reagents For Controlling Coagulation and Thrombosis.

In some embodiments, fluid comprising a fluid-modifying reagent is contemplated for use in controlling coagulation cascades, including but not limited to complement cascades. In some embodiments, fluid comprising a fluid-modifying reagent is contemplated for use in controlling thrombosis reactions. In some embodiments, fluid comprising a fluid-modifying reagent is contemplated for use in drug testing for identifying therapeutics for use in treating symptoms in patients having medical conditions related to altered coagulation cascades and/or thrombosis reactions. In some embodiments, the use of higher flow rate is contemplated to reduce the background noise in assays related to coagulation cascades and/or thrombosis reactions.

As one example, multimeric von Willebrand factor (vWF) plays a role as a mechanosensitive protein for maintaining hemostasis of normal complement cascades and thromboic reactions. For example, after injury, vWFF promotes adhesion of platelets to collagen as well as platelet aggregation forming filamentous networks that cover the injured epithelial tissue. vWF's functions are known to be shear-dependent, since multimers have structural elements that unfold under flow-induced tension. See, FIG. 29.

Multimer size and domain structure provide parameters for vWF's shear-dependent functionality. Yet, many polymorphisms of vWF exist with hitherto unknown consequences for human health. It is believed that quantifying the molecular affinities of vWF wildtype and mutants, especially under shear and blood plasma conditions, will reveal new information related to biomarker identification and drug development for treating medical conditions related to coagulation and thrombosis.

A plurality of different sizes of vWF multimers exists at low shear rates as inactivated coiled states in the blood stream of humans. Increasing shear stress, such as during blood vessel injury, induces conformational changes in the coiled multimers, such as elongation, resulting in exposing new binding sites. These newly exposed binding sites now allow specific intemolecular vWF binding to other blood components, such as Complement 4 (C4) and ADAMTS13. Metalloprotease ADAMTS13 in turn regulates vWF size distribution through shear-dependent proteolysis. vWF also binds to endothelial cells, platelets and collagen. In particular, vWF and platelets form collective networks during hemostasis. See, FIG. 30A-C.

FIG. 29 shows schematic diagrams illustrating Willebrand factor (vWF) in a coiled conformation circulating in a blood vessel (left) then elongated after exposure to shear during coagulation (right). www.shenc.de/B3-Raedler-res.htm, downloaded Sep. 11, 2018.

FIG. 30A-C shows schematic diagrams illustrating Willebrand factor (vWF) conformational changes from a coiled endothelial vWF polymer protein in FIG. 30A, then when exposed to shear stress FIG. 30B in the presence of ADAMTS13, cleavage sites exposed by shear allow ADAMTS13 proteolysis cleavage of the coiled polymer FIG. 30C (left) into smaller multimers and fragments. Alternatively, in the presence of shear and the absence of ADAMTS13 cleavage, FIG. 30C (right), as vWF unfolds binding sites are exposed by conformational changes allowing attachment to platelets and other components causing platelet aggregation. Tsai "Platelet Activation and the Formation of the Platelet Plug: Deficiency of Adamts13 Causes Thrombotic Thrombocytopenic Purpura." Arteriosclerosis, thrombosis, and vascular biology, 23(3):388-396 (2003).

B. Physiological Relevant Shear Obtained Using Percoll Enhances The Antithrombotic Function Of Healthy Endothelial Surface.

An exemplary method is provided here for using a fluid modifying agent, example Percoll, for enhancing the surface of a healthy endothelium, in other words and described herein as providing physiologically relevant shear rates in fluidic chips.

In brief, after PDMS surface functionalization, the entire chamber was coated with extracellular matrix (ECM) consisting of a mixture of rat tail collagen I (100 µg/ml in phosphate buffered saline (PBS); BD Biosciences) and fibronectin (30 µg/ml in PBS; BD Biosciences) incubated at 37° C. for 2 hours before washing with PBS. In order to minimize the biological variability of endothelial cells, two fresh vials (passage 1) of Human Umbilical Vein Endothelial Cells from pooled donors (HUVECs, Lonza, C2519A) were thawed at the start of the study. These HUVECs were cultured in Endothelial Growth Medium-2 (EGM-2, Lonza, CC-3162) and passaged twice before being frozen at passage 3. At each experiment, two vials of cells were thawed and expanded for 3 days in EGM-2. Cells were gently detached with 0.05% trypsin (BD Biosciences, 2-4 minutes incubation at room temperature) and $8 \times 10^6$ cells/ml were introduced into the ECM-coated channels. After incubating for 30 minutes at 37° C., cell attachment to the bottom surface of the chamber was assessed by microscopy. Then, a second flask of HUVECs was trypsinized and used to seed the upper surface of the microfluidic chamber by introducing the cell suspension, inverting the chip, and incubating at 37° C. for 30 minutes. Each fluidic chamber was gently flushed with EGM-2 twice in order to remove unbound cells, then chips were incubated overnight at 37° C.

The next day, chips were connected to a syringe pump (Chemyx Fusion 200) and perfused with EGM-2 for 2 days (30 µl/hr) to provide continuous supply of fresh media. On day 3, medium was switched to EGM-2 with low serum (1% FBS) and a fluid-modifying reagent. On day 4, chips were used for immunostaining and blood perfusion experiments.

FIG. 31A-B shows exemplary representative images showing effect of human endothelial cells (HUVECs) growth in microfluidic channel and perfused overnight with (FIG. 31A) standard cell culture medium (EGM2-MV) at low shear rate or (FIG. 31B) with EGM2-MV including a fluid-modifying reagent to recapitulate physiological relevant shear stress. When compared to cells grown at physiological shear rate, endothelial cells grown at low shear rate express higher levels of the pro-thrombotic receptor vWF (panels on the left and center). Platelets tend to thinly interact and adhere on HUVECs grown at low shear rate (right).

FIG. 32A-C shows exemplary results obtained via image analysis and quantification of the fluorescence intensity of coagulation components, at low shear vs. physiologically relevant shear, demonstrates that physiological relevant shear enhances the antithrombotic function of healthy endothelial surface and improves the signal-to-noise ratio of the in vitro assay. Accordingly, human endothelial cells grown at low shear rate express higher levels of the pro-thrombotic receptor vWF when compared to cells grown at physiological shear rate (left). Exposure to physiological shear rate suppresses unwanted platelet adhesion (center) and fibrin deposition (right), both markers of injured or inflamed endothelial cells rarely detectable on healthy endothelial vasculature. FIG. 32A exemplary cWF. FIG. 32B exemplary platelets. FIG. 32C exemplary fibrin.

C. Cells Incubated Under Physiological Relevant Shear For Testing Compounds Affecting Blood Coagulation.

In some embodiments, cells growing in fluidic devices are exposed to physiological relevant shear prior to drug testing compounds for affecting blood coagulation (i.e. clotting process). For blood coagulation, typically when a coagulation cascade is triggered blood clotting factors (including complement cascade molecules) come together with platelets to form a fibrin clot. A fibrin clot includes platelets clumped together to form a plug at the site of a damaged or injured blood vessel keeping the platelets in place and preventing blood from flowing out of the blood vessel. When the blood is slow to clot, or doesn't clot, excessive or prolonged bleeding can occur. A lack of clotting may also lead to spontaneous or sudden bleeding in the brain, intestines, muscles, joints, or other parts of the body. Thus, in some embodiments, drugs are intended increase coagulation, such as in patients in need of faster coagulation rates, such as in hemophilia patients, patients with Vitamin K deficiencies, von Willebrand disease, blood factor deficiencies, etc. Hemophiliacs, and patients with other types of clotting disorders, after an injury suffer from delayed clotting of the blood. In some embodiments, drugs decrease coagulation, such as patients in hypercoagulable states.

In one embodiment, a blood-brain barrier (BBB) On-Chip is contemplated for use with fluid comprising a fluid-modifying reagent. As one example, a blood-brain barrier (BBB) On-Chip was exposed to physiological relevant shear (3 Dynes, using Percoll) for one day (24 hours) to reconstitute a functional blood brain endothelial barrier. The shear treated brain endothelial cells was then used for testing a drug for inhibiting coagulation.

In general, iPSc derived Human Brain Microvascular Endothelial Cells (iHBMECs) were seeded and grown on-chip. In order to reconstitute a functional blood barrier for a blood coagulation test, the BBB was then exposed to physiological relevant shear (3 Dynes, using Percoll) for one day (24 hours). FVIIa, a molecule used in clinic to treat patients affected by Hemophilia was used for testing coagulation, i.e. platelet coagulation. One observation, brain endothelial cells growing at "low" shear gives a sort of false positive (i.e. toxicity that should not be there). However, cells growing at physiological shear rate, tolerate the drug treatments, in other words do not trigger thrombosis/toxicity.

iHBMECs grown on-Chip, then exposed to physiological relevant shear (3 Dynes, using percol), for one day and then perfused with whole human blood stained for platelets (magenta) and fibrin (cyan). Unexposed chips were also perfused with whole human blood stained for platelets (magenta) and fibrin (cyan) for comparison In order to mimic the hemophiliac condition in vitro, a monoclonal antibody (Sekisui ESH-8) was used to treat chips in order to inhibit the endogenous FVIII. During the experiment, blood perfusion was for 12 minutes at 60 ul/min (≈3 dynes) than chips were immediately imaged. In order to reduce the risk of perturbing the system, images were obtained from living cells (live imaging), without washing or fixation.

Results: Chips exposed to physiological relevant shear and perfused with blood (FVIII inhibited) show a very low level of platelet adhesion and fibrin deposition, as shown in image FIGS. 33A and 33B (higher magnification of 33A) and reported as measure of fluorescent signal intensity in FIG. 33C. Similarly, blood perfused through endothelial channel of chips grown at lower flow rate show low levels of platelets and fibrin deposition. Of note, results obtained via image analysis indicate that the cells grown at lower shear rate may trigger platelet adhesion and fibrin deposition (an phenomenon that we observed also on endothelial cells obtained from a different source such as HUVECs). Importantly, when we tested the therapeutic FVIIa, we observed that while the drug did not affect platelets or fibrin adhesion to cells grown at physiological relevant shear, the amount of platelets and fibrin found on cells grown at low flow rate was surprisingly higher, an event frequently triggered by various toxic compounds. Because FVIIa is a therapeutic compound well-tolerated, safe and frequently used in clinic to threat hemophiliac patients, the increased platelet and fibrin deposition is an event that we considered not-specific and rather a false positive.

Conclusions: Our results strongly support the hypothesis that iHBMECs grown at physiological shear rate develop and maintain biological properties of a healthy and mature vascular endothelium capable of sustaining blood perfusion, recapitulating blood-endothelial interaction what ultimately represents a potential new tool for testing of drug compounds that affect the coagulation cascade.

FIG. 33A-C shows exemplary results of using a fluid-modifying reagent (Percoll) in order to induce shear. Treatments included: 1. Blood (FVIII inhibited); 2. Blood+FVIIa (reconstituted); 3. Low shear (untreated BBB On-Chip); 4. Physiological relevant shear (shear treated BBB On-Chip). FIG. 33A shows an exemplary florescent image of a whole (entire) channel on chip at low magnification. Fibrin is shown in cyan. FIG. 33B shows magnified details from channels shown in FIG. 33A. FIG. 33C shows exemplary coagulation results as % Area Coverage of platelets.

D. Using Fluid Modifying Reagents for Providing Physiological Shear Rates for Overcoming a Loss of Barrier Function in Human Brain Endothelial Cells.

FIG. 34 demonstrates problems: a loss of barrier function. Brain endothelial cells grown in media 1 (M1): hEndothelial SFM+1% PPP (Puromycin), loose barrier function by Day 10 as shown by bright field microscope images of cells on-chip with a corresponding dextrin leakage chart. Additionally, Immunofluorescently stained micrographs with a corresponding graph of barrier function loss, demonstrates Endothelial (iHBMEC) tight junctions loss of barrier function by Day 10 in a dose dependent fashion. dose-dependent response to TNFalpha. Control (left) 100 ng/ml TNF (right). Thus, loss one or more causes of a loss of barrier function in human brain endothelial cultures provides difficulties with immune recruitment assays.

Therefore, a strategy to Prolong Viability and Function of iHBMECs was developed and tested: Post-differentiation treatment with Puromycin (~0.25 ug/ml); Adjusting ECM: Collagen IV/FN+/− Other ECM components; Adjusting seeding and post-seeding media; and determining the effect of shear stress on physiology, e.g. iHBMECs for use on the BBB-Chip.

FIG. 35 shows exemplary results of Media Optimization, Day 07 and 10. Bright field microscope images: upper panels Media 1, lower panels Media 2. Right panels ECM 1 and left panels ECM 2 (+Laminin). Lower graph of % dextran leakage over time, shows Media 2 enhances proliferation of iHBMECs but does not improve barrier function. ECM2 seems to improve iHBMEC monolayer morphology.

FIG. 36 shows exemplary results of Effect of Puromycin Selection on Barrier Function. Media 1 (M1): hEndothelial SFM+1% PPP. M2: M1+Endothelial growth medium (EGM) supplements; M4: Advanced DMEM/F12+1% PPP+ EGM supplements. Graphs upper, M1 vs. M4, and lower M2 vs. M4, demonstrated that Puromycin treatment does not seem to contribute to improved barrier maintenance or robustness in the "long-term".

Physiological shear stress has been shown to increase the level of expression of different surface receptors and molecular transporters with critical functions for the BBB in both, normal and pathological conditions. Physiological shear stress has been shown to increase the level of expression of different surface receptors and molecular transporters with critical functions for the BBB in both, normal and pathological conditions. In fact, increasing shear stress improves viability of brain; Physiological shear stress improves TEER microvascular endothelial cells; and expression of junction marker as shown in FIG. 36.

FIG. 37 demonstrates apoptotic rates over time, apoptotic rates under different shear conditions, and TEER. For reference, Cucullo, et al., The role of shear stress in Blood-Brain Barrier endothelial physiology. BMC Neurosci. 2011.12-40; and DeStefano, et al., Effect of shear stress on iPSC-derived human brain microvascular endothelial cells (dhBMECs). Fluids Barriers CNS. 2017. 14(1):20.

Therefore, the following Exemplary Experimental Designs and experiments were done: Condition 1: Chips at D2: Flowed at 60 ul/hr and maintained for 4 or 10 days. Condition 2: Chips at D2: Flowed at 60 ul/hr for 48 hours; then increased to 600 ul/hr for 48 hrs. Condition 3: Flowed at 60 ul/hr for 48 hours; then increased to 600 ul/hr for 48 hrs.; then increased to 900 l/hr for 4 days. Condition 4: Chips at D2: Flowed at at 900 ul/hr for 24 hours. The following figures provide exemplary results.

FIG. 38 shows an exemplary Effect of Shear on hBMEC Physiology under a high flow rate (600-900 ul/hr) and recirculation which facilitates maintenance of barrier function in the BBB-Chip. Morphology (brightfield) for Day 04; Day 07; Day 10 for upper panels Control—Low Flow Rate and lower panels High Flow Rate. Barrier function was measured using 3 kDa Dextran in the chart below. Barrier function—3 kDa Dextran is better at High Flow Rate vs Low Flow Rate.

FIG. 39 shows exemplary immunostaining—Day 07; before and after, upper panels. And Immunostaining—Day 10; before and after, lower panels.

FIG. 40 shows exemplary Improving shear stress and recirculating media generates a more robust BBB, as measured by barrier function and morphology.

Therefore, BBB-Chip: iHBMEC Morphology and Barrier Function shows that by improving shear stress and recirculating media generates a more robust BBB, as measured by barrier function and morphology.

Summary: Increasing shear stress and recirculating media has improved robustness and barrier tightness of the BBB; Longevity of the chip is almost doubled, now lasting up to 10 days.

V. A Modified Fluid For Use With Growing Cells In Chips: Better Growth Rates Of Cells.

In addition to better brain endothelial layers under physiological shear stress provided by a fluid modifying agent, other cell types may benefit from exposure to a fluid modifying agent during or after differentiation in fluidic devices. In some embodiments, a fluid comprising a modifying reagent is contemplated for use in growing cells on fluidic devices, i.e. on-chip, that is not associated with recruitment of immune cells.

As one example, kidney cells show improved growth when exposed to shear induced by inverting chips. Some examples of a kidney on-chip described in PCT/US2016/ 064179 published as WO2017095899 (Jun. 8, 2017) "Gradient microfluidic devices and uses thereof", herein incorporated by reference in its entirety; etc.

Thus, in some embodiments, a fluid comprising a modifying reagent is contemplated for use in fluidic Kidney On-Chip, not associated with recruitment of immune cells. Such use of a fluid-modifying reagent is contemplated to provide increased growth rates over time compared to current methods, including over methods comprising inverting chips.

VI. A Modified Fluid For Use With or As A Mucus Substitute.

In some embodiments, fluidic devices are contemplated for use with a fluid comprising a modifying agent and mucus or as a mucus substitute, as described herein.

In some embodiments, fluidic devices may comprise respiratory cells, aveolar cells, small airway cells, intestinal cells, etc.

Some exemplary chips are described in PCT/US2017/016079 published as WO2017136462 (Aug. 10, 2017) "Systems and methods for growth of intestinal cells in microfluidic devices"; lung on-chips herein incorporated by reference in its entirety.

E. Additional Advantages Of Using Bodily Fluid Mimics In Microfluidic Devices.

Microfluidic devices are used for differentiating cells on chip; for testing media formulations on-chips for a variety of cells, etc. In some embodiments, cells on-chips grow faster; form morphological structures that mimic in vitro structures; differentiate faster; differentiate more effectively, live longer; etc., under flow. However, cultures under fluid flow use more fluid as the flow rate increases. This is economically problematic when fluids contain reagents, such as growth factors, certain antibodies, etc., for example when used in experimental media, iPS cell expansion media, etc. Thus, use of fluids containing modification agents are contemplated to find use in lowering the amount of fluid used at a particular fluid flow rate while providing physiologically relevant forces on cells that are in contact with the modified fluid.

Another problem when using fluids flowing through microfluidic channels is encountered when viewing cells by light microscopy through fluids or within fluids flowing through microchannels. Higher flow rates move cells or cellular components, at faster rates, into and out of focal planes while fluids with low cell buoyancy allow gravitational forces acting on cells to move cells downward. These problems may be overcome by using fluids containing modifying reagents for keeping cells or cellular components within microscopy focal planes over a longer time period, allowing observations and micrographs to be in focus over longer experimental time periods. In other words, a fluid-modifying reagent may counteract gravitational (and other) effects on cells and cellular components in fluids. In some embodiments, adding a fluid modifying reagent to a fluid may in effect reverse gravitational forces, such as in producing results in upright chips that previously were obtained by using upside down chips, i.e. fluid-modifying reagents counteract gravitational forces.

Thus, providing a physiologically relevant fluid for simulating physiological shear stress, (e.g. force) at least in part for keeping cells (or other particles) in suspension in fluids under flow, and slower settling rates in fluid reservoirs, was desired for use with microfluidic chips. In particular, such improvement in providing a closer physiological shear stress was desired for immune recruitment experiments on-chip, in part for use in drug testing and new drug discovery. Indeed, one solution discovered as described herein, was to provide a fluid having physiological shear stress values on-chip similar to those found in humans, including but not limited to blood, as one example, physiological shear stress values on-chip similar to those found in a human blood vessel.

More specifically, a biophysical blood substitute is contemplated to provide, in part at least 4 of the following: 1) recreating, i.e. mimic, rheological properties of the human blood and mechanical forces generated by blood acting on the endothelium, including but not limited to cells attached to the endothelium, and on cells or other particles in solution. Such interactions might induce complex local hemodynamic conditions that are relevant to understand disease pathophysiology. Further, such interactions of relevant forces generated by blood properties in combination with flow dynamics may be used for drug discovery and preclinical testing of therapeutics.

A fluid for mimicking (i.e. recreating in vitro) rheological (physiological) properties of the human blood and mechanical forces generated by blood on endothelial cells, Such interactions might induce complex local hemodynamic conditions that are 1) relevant to test and evaluate disease pathophysiology. 2) Allow to perform long term experiment, in situation that require to keep particle/particulates in suspension. a fluidic means to perform a longer term experiment over that of a nonrheologic fluid, such that conditions warrant the need for particle/particulates to remain in suspension rather than settle out during the experiment. 3) blood substitute optical properties (transparency) allow its use in high resolution microscopy applications and high speed real time imaging. 4) Minimal volume of fluid required.

Thus, a blood surrogate is a tool for modeling the physiological effect of the shear on endothelial cells and can be a valuable tool to investigate the effect on the biological behavior of cells/particulates (i.e. red blood cells, white cells and platelets) and noxious agents (i.e. bacteria, metastasis, virus, pollutants) present in the blood. In specific setups, the blood substitute could be also used as diagnostic tools in personalized medicine, in application where freshly isolated blood cells can be suspended into the viscous fluid and run for mimic diseased state. In fact, after defining specific metrics and using cells isolated from blood of patients with blood disorders, it would be possible to make prediction about patient response to mechanical forces (i.e. shear stress), immune system or blood activation (i.e. clog formation, coagulation) and behavior of blood cells in these diseased states. In the future, one can envision the routine incorporation of these data in hospital practice to help virtual treatment planning of the patient as it occurs already in other medical disciplines.

A system comprising a fluid modifying agent can be integrated with an Organ on-Chip, including but not limited to Organ on-chips, in part as described in U.S. Pat. No. 8,647,861, etc., such that any microfluidic chip may comprise a fluid as described herein. Such a microfluidic system comprising a modified fluid may provide a means by which to study and test interactions between multiple cell types (at least two or more) within the modified fluid, including but not limited to a fluid blood substitute (mimic) as described herein. Further, a microfluidic system comprising a modified fluid may provide a means by which to study how inflammation of epithelia (and other parenchyma cells), in the presence of one or more of: a drug(s), chemical compound (s), and subject to certain physical forces may affect/influence the behavior of the endothelial cells located within the vascular channel. As one example, a layer of endothelial cells that line a channel may be evaluated for changes over time during or after a modified fluid flows through the channel, and over the endothelial cells. In some embodiments, a layer of endothelial cells that line a channel may be evaluated for changes over time during or after a modified fluid flows through the channel wherein the fluid comprises one or more cell types, including but not limited to white blood cells. As yet another example, in some embodiments, a layer of endothelial cells that line a channel may be evaluated for changes over time during or after a modified fluid containing blood components and/or blood-cells, flows through the channel, and over the endothelial cells, for identifying changes in blood and/or blood-cell behavior (for nonlimiting examples, white blood cells, red blood cells and platelets).

Strength over other systems: 1) Capability to perform long term experiment 2) Blood vessel-endothelial cell interaction 3) Direct monitoring and recording 4) Compatibility with the Organ-Chip model already developed. 5) Potential application for patient-specific blood reactivity modeling in vitro (personalized medicine).

One example is for simulating immune cell recruitment into bodily tissues. Another example is how a blood circulating tumor cell enters a bodily tissue. Additional examples include, but are not limited to, immune cells recruitment and circulating tumor cell. It will also fix the issue to have to invert the chips during flow, where the immune cells by gravity are closer to the bottom of the chips, instead to the membrane where they can or not be recruited.

Applications of this system may further involve (but is not limited to) evaluating complex events, such as thrombosis, thromboembolism, aneurism, atherosclerosis, ischemia and for determining the significance of in vitro lesions induced on-chip for mimicking those lesions that are generated in vivo by pressure and other mechanical stresses that may change in vivo properties and/or functions (including but not limited to changes in physiology) of blood cells, e.g. white blood cells, red blood cells and blood components, and changes in in physiology of blood vessel endothelial cells.

In some embodiments, a mucosal fluid substitute for mimicking a tissue fluid is provided. In some embodiments, a mucosal fluid substitute for mimicking a tissue fluid is used with a microfluidic system described herein, including but not limited to additional microfluidic systems described in publications referenced herein. In some embodiments, a mucosal fluid substitute for mimicking a tissue fluid is used on-chip in any of the microfluidic chips described herein, including but not limited to additional chips described in publications referenced herein.

Moreover, as mentioned herein, any microfluidic device is contemplated for use with fluids comprising a modifying agent, e.g. a thickening agent. In some embodiments, fluids intended for use in a microfluidic chip comprise a thickening agent. In some embodiments, a microfluidic chip device comprising a membrane and cells is contemplated for use with fluids comprising a thickening agent. In yet further embodiments, a microfluidic chip device comprising a membrane and cells is contemplated for use with fluids comprising a thickening agent. In some embodiments, the use of such fluids comprising a thickening agent increase shear rates within the fluid.

The following is a brief description of how shear, viscosity, density, buoyancy, etc., affects cells in fluids, relating to both in vivo physiology and in vitro, within a microfluidic chip.

III. Physiological Shear Stress.

Shear stress, in relation to liquid under flow along cell surfaces, refers to the mechanical force induced by the friction of liquid against the cell membrane. This force is parallel to the fluid's surface and called shear stress. Shear rate refers to a rate at which a progressive shearing deformation is applied to some material, such as cells. When cells undergo shear stress, they may be able to counteract deformations caused by shear stress by rearranging their cytoskeleton to take on a different shape. Other shear stress dependent effects include changes in metabolism, gene expression, and differentiation. (What Type of Shear Stress Do You Investigate? At https://ibidi.com/content/123-what-type-of-shear-stress-do-you-investigate, accessed, Oct. 31, 2017).

Physiological shear stress values in human vary from 0.5 to about 15 dyne/cm$^2$ depending on the vessel type (e.g., artery or vein) and the size. In vivo, several adherent cell types are exposed to mechanical shear stress in biofluidic systems such as blood, lymphatic vessels, nephrons, etc. This mechanical stimulus has a great impact on the physiological behavior and adhesion properties of cells. (What Type of Shear Stress Do You Investigate? At https://ibidi.com/content/123-what-type-of-shear-stress-do-you-investigate, accessed, Oct. 31, 2017).See. Table below for examples of blood vessel type in relation to shear stress.

TABLE 10

Shear stress in fluids, i.e. blood, of a human circulatory system.

| Vessel | Shear stress (dyn/cm$^2$) | |
|---|---|---|
| | Average | Maximal |
| Aorta | — | >15 |
| Artery | — | 5-10 |
| Middle vein | 0.8-1 | — |
| Small vein | 0.5 | — |

Source: "What Type of Shear Stress Do You Investigate?" (At https://ibidi.com/content/123-what-type-of-shear-stress-do-you-investigate, accessed, Oct. 31, 2017).

Thus, for modeling certain types of physiological systems, in particular in related to drug discovery and personalized medicine, mimicking shear stress inside of a channel in a microfluidic chip is problematic. For one example, to provide physiological levels of shear stress in a microfluidic channel, one solution is for increasing the velocity of the medium flowed inside the micro-channel. However, even if technically achievable as a viable solution for this problem, it is impractical because it would require the use of very large volumes of media. More specifically, flow rates compatible with physiological relevant shear stress using media are generally in the order of several milliliters of medium per hour. Media are generally expensive and run an experiment with this rate will have prohibitive cost. Furthermore it would involve the use of extremely large reservoir to store the necessary volume of medium. Further, precipitation of particles/particulates suspended into medium are usually a limiting factor in experiments that require to perfuse immune cells/beads/metastasis over a course of several hour. The effect of particle precipitation generally manifests itself in minutes or even second from the suspension of the particles/particulates in medium. However it can be very variable depending on the type of particles.

A. Shear Rate Enhancement.

During the development of some embodiments of microfluidic chips, for one example an airway on-chip, it was discovered that by changing the flow rates of fluids through microfluidic chips, and/or by changing geometries of the microchannels, that the biology of the systems work better, i.e. are more in vivo like, when microfluidic flow generates more physiological levels of shear. As more specific examples, immune-cell recruitment assays required experimentation in order to tune the shear rate (for examples, when measuring rates of diapedesis through endothelial layers, in particular for neutrophils, PBMCs, T cells). In other words, biological mimics of immune-cell recruitment worked more like in vivo recruitment when the shear rate as altered, i.e. tuned, for example when using neutrophils, PBMCs, T cells, etc. Further, many types of endothelial cells respond to shear in different ways including, having a tendency to elongate parallel to higher rates of flow, as observed in chips, including for example, BBB on-chip and kidney on-chip. In part, because these representative organs are barrier organs, it is contemplated that barrier integrity would be higher when the endothelial cells are exposed to more physiological shear, in microfluidic chips, e.g. for kidney on-chips.

Moreover, shear may also have effects in the airway on-chips. In this embodiment, typically air shear is contemplated to have an effect, (as gas flowing generated shear), but there may be additional effects as liquid shear in relation to mucus and other liquids on the surface of lung cells in the air channel, in addition to shear in the endothelial channels. Thus, having a fluid mimic for mucus is contemplated herein for use with parenchymal cell layers on-chip for mimicking biological tissues exposed to mucus and covered by mucus.

Therefore, in some embodiments, a fluid has altered shear rates, in particular enhanced shear rates, by a fluid-modifying agent, such as those described herein.

B. Shear Rate, Generally.

Thus, without being bound by theory, shear rate is a function related to geometry, flow rate and fluid viscosity. Accordingly, one of the means for obtaining higher shear is increasing flow rates of fluids through microfluidic chips. In fact, initial experiments using fluid under flow through microfluidic chips, the typically means for obtaining higher shear was to increase flow rates of fluids. However, increasing flow rates for providing more relevant physiological conditions on-chips triggered additional challenges related to the use of larger volumes of fluid flowing through chips. This use of large volumes of media or other fluids can be problematic, in part because: a) handling large volumes of liquid can be challenging in terms of reservoirs, e.g. increasing capacity and instrument design (e.g. increasing the capacity for using a higher volume of fluid; b) media can be expensive (e.g. media used for enteroids, stem cell media comprising growth factors, isolated, synthetic and recombinant agents, etc.); c) large volumes of liquid flowing over cells into which signals from cells enter, may be diluted into large volumes of flowing fluid and may be washed away before encountering receptors, thus may mask (i.e. harm) autocrine signaling capabilities, and may make pharmacokinetic experiments difficult to interpret properly, etc.; d) large volumes of fluid under flow may whisk away some amount of agents added to fluids prior to engaging cell receptors; or prior to having a biological effect, such as growth factors, test agents, test drugs, etc.

One potential solution is to recirculate fluids thus lowering the overall amount of fluid in the reservoirs and tubing. However, fluid recirculation, unless used for modeling blood component recirculation-bodily fluid recirculation, is unlikely to provide accurate results for contemplated experiments.

Further, in the absence of fluid recirculation, the media (where fluid recirculation is not preferred in some embodiments because we often want to assess the single-pass media effect on the cells on-Chip), has a higher flow rate which means going through too much media for a single experiment with a few hours of incubation time or over time periods of days and weeks.

Thus, during the development of the present inventions, solutions were contemplated and tested for overcoming the challenges of providing a higher shear rate that did not involve increasing flow rates of fluids. Therefore, in one embodiment, the present invention contemplates increasing shear independently of flow rate by supplementing the liquid used with a fluid (liquid)-modifying reagent, e.g. a viscosity-modifying reagent, a density modifying reagent, etc.

C. Viscosity Enhancement: Viscosity-Modifying Reagents.

A desirable feature of the viscosity-modifying reagent is that it should not lead to (i.e. independently induce) toxicity or inflammation. Thus, a viscosity-modifying reagent is contemplated for use that is non-toxic and causes little to no inflammation when in contact with either immune cells or endothelium, in part, because inflammation is often one of the readouts of a microfluidic chip. In one embodiment, identifying a potential viscosity-modifying reagent for use with a microfluidic chip is tested on-chip for its capability to induce little to no inflammation on desired cell types, including but not limited to endothelial cell types, parenchymal cell types, immune cell types, etc., on-chip. In some embodiments, identifying a potential viscosity-modifying reagent for use with fluids containing cells is testing for little or no inflammation on cells in fluids comprising the viscosity-modifying reagent over time periods where such fluids are intended for use flowing through chips and held within instrument systems.

Additionally, it was desired to use more natural products as viscosity-modifying reagents, such as Alginate, an anionic polysaccharide distributed widely in the cell walls of brown algae. However, while useful for some purposes, during development of the present inventions, it was discovered that the use of Alginate was associated with unacceptable inflammation (e.g. when measuring background cytokine expression). In contrast, Percoll does not typically appear to cause inflammation on-chip or on cells in a Percoll solution, an unexpected advantage of using colloidal silica coated with polyvinylpyrrolidone (PVP).

Viscosity-modifying (VMAs) (re)agents include admixtures and temperature. Contemplative viscosity-modifying reagents include but are not limited to: sucrose, a water-soluble organic polymer, e.g. having an average molecular weight between 10,000 and 10,000,000, polyvinyl pyrrollidone, polyethylene glycols, polyvinyl alcohols, polyvinyl acetals, polyacrylic acids, polyacrylamides, plant gums, cellulose ethers, celluloses, hemicelluloses, dextrans, inulins, oligosaccharides and polysaccharides. As described herein, certain potential VMAs for use with microfluidic chips were tested and found to be unsatisfactory for immune recruitment assays.

In one embodiment, the viscosity-modifying reagent comprises a gel (wholly or partially gelled) or gel precursors (e.g. alginate, polyacrylamide, agar), polymers (silicone), proteins (e.g. albumin), and thickeners such as xanatham gum. Viscosity-modifying reagents can also comprise colloids, such as silica-based colloids, and in particular Percoll, Ficoll, etc.

Thus, we have developed an optically transparent blood substitute made of silica nano-particles (e.g. Percoll), which increases the viscosity of the medium and has no measurable inflammatory effect on cells in microfluidic chips.

IV. Buoyancy- And Density-Modifying Reagents.

A. Buoyancy-Modifying Reagents.

In some embodiments, control over cell buoyancy, i.e. buoyancy forces acting upon a cell located within a microfluidic device, is desired. Buoyancy is related to the density of a fluid. As one example, an object, such as a particle, sinking rapidly in a fluid is displacing more fluid than an identical particle in the same fluid sinking at a lower rate when the identical fluid has a greater density, such as by the addition of a density-modifying reagent. Buoyant force in reference to a particle, such as a cell, refers to a combination of variables acting upon a cell including the density of the fluid the cell is submerged in, the volume of the fluid displaced by the cell, and the acceleration of the cell in a particular direction due to gravitational force upon the cell. Thus, changing cell buoyancy on-chip may be accomplished in several ways, including but not limited to: by changing the orientation of the chip, i.e. by inverting (flipping) the chip upside down, i.e. changing the direction of gravitational forces (whose limitations are discussed herein); by changing the size of the cells added to a chip; or by changing the actual density of the fluid around a cell.

Thus, without being bound by theory, increasing the density of a fluid carrying immune cells increases the buoyancy of these cells. Specifically, once a certain density is reached, the cells become buoyant, meaning that they float upwards in the channel. Accordingly, cells floating upwards can better interact with the endothelial cells present at the top of the channel (under the membrane). The end result is a protocol that, amongst other advantages, allows for effective immune-cell recruitment and specifically without needing to flip Chips. The latter part is especially an advantage in the context of our Zoe system.

Thus, in some embodiments, cell buoyancy is altered by changing the size and/or weight of the cells, for nonlimiting examples, by using smaller immature cells vs. larger mature cells, i.e. B cells, where the immature B cells may be smaller in size than in their mature antibody producing cells, i.e. plasma cells; immature monocytes vs. mature macrophages; by using lymphocytes (smaller) vs. granulocytes, such as neutrophils (larger and heavier).

In some embodiments, adding a density-modifying reagent to a fluid alters cell buoyancy. In fact, the use of Percoll in neutrophil recruitment with lung on-chips eliminates the need for chip flipping by increasing buoyancy of the cells. Thus the use of Percoll for providing a specific shear force regime results in increasing shear force at lower flow rates. Thus reducing the need for large amounts (volumes) of fluids, e.g. cell media, to achieve higher shear forces. In fact, the use of Percoll results in an increase of shear independently of flow-rate. This can allow us to get to physiologically relevant shear levels without excessive medium volume. Therefore, a Percoll media formulation is contemplated to assist immune recruitment assays for immune-cell types on Chips. Moreover, the use of a fluid-modifying reagent will increase shear independently of flow-rate.

B. Fluid Density-Modifying Reagents.

During the development of the present invention, multiple types of "thickening agents" were compared and found to create an inflammatory response within the microfluidic device, which in the majority of embodiments is an undesired biological impact. However, it was discovered, as described herein, that the addition of Percoll to fluids in a microfluidic chip did not trigger a measurable inflammatory response. Further, addition of Percoll as a fluid modifying reagent allowed the control of cell buoyancy. Furthermore, controlling cell buoyancy using a fluid modifying reagent provides an additional benefit, e.g. when increasing buoyancy of white blood cells (WBCs), by replacing and thus removing the step of moving microfluidic chips into an upside-down position in various immune-cell recruitment assays in order to increase the number of cells interacting with endothelial cells attached the pourous membrane directly beneath cells attached to the opposite side of the membrane.

Therefore, in additional embodiments, a means for changing cell buoyancy is provided by the use of a density-modifying reagent, e.g. a "thickening agent" in the fluid for altering fluid density as a means for changing cell buoyancy within a microfluidic chip. In preferred embodiments, such "thickening agents" added to fluid, e.g. bathing cells and flowing through a channel of a microfluidic device, does not create an inflammatory response (and hence undesired biological impact for studies where non-reactivity of the fluid is desired). Thus, in some embodiments, density-modifying reagents control cell buoyancy.

A density-modifying reagent, e.g. a thickening agent, for use as or in a fluid substitute is related to principles of density gradient centrifugation. Density-modifying reagents added to liquids typically increase the density of that liquid in relation to the amount of reagent. In relation to using density-modifying reagents in liquids containing cells, in preferred embodiments, the density-modifying reagent increases the density of the fluid without significantly altering the fluid's osmolality. In part, significant changes in osmolality would most likely result in deformation of a cell leading to rupture of the cell membrane. Moreover, changing the density of a liquid containing a cell, in part, may also change the buoyancy of a cell in that modified liquid. In other words, a buoyant force on a cell, provided in part by the liquid, causes the transport of a cell to a location where the surrounding fluid density most closely equals the cell's density.

An analogous system where centrifugal forces are used for separating particles. i.e. cells or cytoplasmic particles, of different density, is density gradient centrifugation. In fact, there are at least two types of centrifugal techniques for separating particles, density gradient centrifugation and differential centrifugation. Density gradient centrifugation refers to separating particles solely on the basis of their density, while differential centrifugation refers to separating particles on the basis of their size and shape. While both size and density affect sedimentation velocity, their size difference dominates when separated by centrifugation.

When a suspension of particles is centrifuged, the sedimentation rate of the particles is proportional to the force applied. Thus, physical properties of the solution will also affect the sedimentation rate. At a fixed centrifugal force and liquid viscosity, the sedimentation rate is proportional to the size of the particle and the difference between its density and the density of the surrounding medium.

Thus, when a suspension of particles is centrifuged, with or without a differential agent, the sedimentation rate of the particles is proportional to the force applied.

One example of an equation for the sedimentation of a sphere in a centrifugal field is: $v = d^2 (p_p - p_l)/18 \eta \times g$. Where $v$=sedimentation rate, $d$=diameter of the particle (i.e. as a hydrodynamically equivalent sphere), $p_p$=particle density, $p_l$=liquid density, $\eta$=viscosity of the medium, and $g$=centrifugal force.

For use herein, at numerous points along tubing attaching fluid holding tanks and effluent tanks, allowing a flow of fluid into, within, and out of microfluidic chips, particles encounter a variety of centrifugal fields, although mostly far less than produced by a centrifuge. Therefore, particles flowing through tubing and chips have certain sedimentation rates, depending upon the size of the particle, particle density, liquid density, viscosity of the medium, and centrifugal force, as put forth in an exemplary equation relating to the sedimentation of a sphere in a centrifugal field.

To compare theory to results, the following exemplary values were inserted into the equation above, using 1 g, for calculating v in a microchannel where lymphocyte cells are suspended in solution in a fluid containing a modifying reagent, such as Percoll. An Average Diameter of a Lymphocyte was used=7.3 um (as part of a range from 6.8-7.8 um), see, for e.g., BioNumber Details Page (Date Edited: Aug. 24, 2017 12:47 PM; http://bionumbers.hms.harvard-.edu/bionumber.aspx?id=100507). An Average Density Lymphocyte was used=1.075 g/mL (see, for e.g., Zipursky, et al., "Leukocyte density and volume in normal subjects and in patients with acute lymphoblastic leukemia." Blood 48(3): 361-71 (1976)). For liquid density, Percoll was used as an exemplary agent where Density Percoll=1.13 g/mL (https://www.sigmaaldrich.com/content/dam/sigma-aldrich/docs/Sigma-Aldrich/General_information/1/ge-cell-separation-media.pdf). For viscosity of the medium, Percoll was used as an exemplary agent. Viscosity Percoll=10 cP (https://www.sigmaaldrich.com/content/dam/sigma-aldrich/docs/Sigma-Aldrich/General_information/1/ge-cell-separation-media.pdf). In, Cell Separation Media, Methodology and applications, Handbook 18-1115-69 AD 05-2007. Thus, Velocity of sedimentation =

$$\frac{(7.3um)^2 \left(\frac{1.075 \text{ g}}{mL} - \frac{1.13 \text{ g}}{mL}\right)}{18(10cP)} \times \left(9.8 \frac{m}{S^2}\right) = -0.2 \frac{um}{s}.$$

The Volume of bottom channel=~10 uL, Flow Rate=30 uL/hr. An Average Residence Time in Bottom Channel=20 min. An Average Buoyant Distance Traveled by Lymphocyte in Bottom Channel=260 um.

Thus, in a fluid containing a modifying reagent, such as Percoll, as colloidal silica particles of 15-30 nm diameter coated with polyvinylpyrrolidone (PVP), a solution containing approximately 50% Percoll should theoretically provide neutral buoyancy on lymphocytes, i.e. allowing lymphocytes to float in solution within a containing rather than sinking towards the bottom or rising to the surface of the container. Experimentally, it was discovered in a lymphocyte recruitment assay on-chip, that when compared to a 25% Percoll solution and an 80% Percoll solution, lymphocytes suspended in a 50% Percoll-media solution flowing through a microfluidic chip showed the highest immune cell recruitment to inflamed endothelium, see for e.g. FIG. 19C.

V. Providing Rheologically Biomimetic Fluids In A Microfluidic Chip System.

A. Embodiments Of Rheologically Biomimetic Fluids.

Embodiments of rheologically biomimetic fluids include but are not limited to: using a range (variations) of ratios of Percoll/Medium, contemplated for matching shear rates found in a variety of body fluids. As one example, a specific dilution of Percoll is meant to simulate or match the specific density of certain cells that are suspended within it.

B. Desired Characteristics Of A Blood Substitute.

The blood substitute is used for at least two different types of applications. As nonlimiting examples, in one type of application, it is added to the fluid (i.e. Blood, Serum, Medium) to keep particles/particulates in it dispersed to be in suspension and flowed in a continuously manner. In this application the relative ratio Percoll/Fluid (i.e. Blood, Serum, Medium), which correspond to a specific density can be varied to adapt to the specific particle/particulates in it dispersed. In this application is also contemplated the use of fluorescent dies, antibodies or other detection solution to better image the blood substitute or the particle/particulates suspended into it. In this second type of application is also contemplated the use of fluorescent dies, antibody or other detection solution to better image the blood substitute.

In another type of application, the blood substitute is flowed into the micro-channel to mimic physiological relevant blood flow shear stresses with the ultimate goal to stimulate the endothelium to fully mature. In this application the relative ratio Percoll/Fluid (i.e. Blood, Serum, Medium) can be varied to adapt the viscosity of the blood substitute to the specific geometry or the specific dimensions of the micro-channel and the working range of the pump in use. So that it is possible to have some flexibility in the use of it to achieve the desired shear.

In some embodiments, a blood substitute is designed to perfuse different fluid such as blood, plasma and medium. The blood substitute can flow in channels lined with endothelial cells without generating inflammation. In some embodiments, a blood substitute can increase viscosity to mimic physiological relevant shear stress at low flow rate. In some embodiments, a blood substitute can increase viscosity to keep particles/particulates in suspension.

One approach to providing a rheologically biomimetic fluid surrogate was contemplated by adding an inert colloid to the fluid medium to mimic the rheological properties of the human blood. In part this was contemplated that by increasing the viscosity of the solution would reduce cell settling in the reservoirs, injection equipment and in the device itself as well as enable to emulate physiologically relevant level of shear stress/pressure in vitro (even in the condition of low flow rate).

Modeling blood shear stress to mimic more closely the physiological conditions to which endothelial cells are exposed to inside the body and stimulate the endothelial cells to fully mature. Yet, the blood substitute (surrogate) helps keeping particle/particulates as defined previously to remain in suspension, allowing to perform long term experiments that require to flow particle/particulates as defined previously.

We have created a medium that mimics rheological properties of the human blood (increased viscosity) and enables recreation of physiologically relevant conditions of immune cells recruitment (shear stress). Presence of an inert colloid (Percoll), that increases media viscosity, in the solution perfused through the vascular channel showed no negative effect on the endothelial cells—as evaluated by the gene expression studies and immunofluorescent staining for adhesion molecules expressed on endothelial cells surface in the context of inflammation Kern Powerpoint.

Specifically, the proposed blood substitute (surrogate) will help to answer questions related to immune cells/tumor cells/endothelial cells interaction, mechanobiology and rheology of human vascular systems etc., such as: 1) how mechanical forces affect the behavior, the morphology, marker expression and maturation of the endothelial cells; 2) how cells contained into the blood substitute (surrogate) alter its rheological properties in reaction to mechanical forces; 3) how the blood substitute(surrogate)/endothelial cells interaction affects the rheological properties of the blood and the immune cells phenotype (e.g. activation) and endothelial cells responses (e.g. expression of membrane receptors); 4) how epithelial and parenchymal cells affect endothelial cells and rheological blood properties in response to external stimuli and stresses (chemical, mechanical, biological etc.).

The blood substitute (surrogate) can be used in/with: Multiple perfusable micro-channel geometries for mimicking a relevant healthy or diseased blood vessel; blood cells or particulate isolated from patient; the system can be integrated with the Organ-on-Chip concept and used to study the effect of the interaction of multiple cell types on blood (for instance one can study how epithelial/parenchyma/mesenchymal cell interact with endothelial cell and how those affect the blood and vice versa); Visualize the lumen of reconstructed blood vessels using microscopy at high speed and high resolution (subcellular), since it is optically transparent.

C. Types Of Fluid-Modifying Reagent: For Use As Or As Part Of A Fluid Substitute.

In some embodiments, a fluid-modifying reagent is a powder. In some embodiments, a fluid-modifying reagent powder is a hydrophilic neutral highly branched polysaccharide (nonionic synthetic polymer of sucrose), for example, Ficoll® 400, Sigma-Aldrich Co. LLC. In some embodiments, a fluid-modifying reagent is a solution. In some embodiments, a fluid-modifying reagent solution is a fluid-mixture of hydrophilic neutral highly branched polysaccharides (nonionic synthetic polymer of sucrose), for example, a Ficoll® solution of 20% in $H_2O$, Sigma-Aldrich Co. LLC. In some embodiments, a fluid-modifying reagent is a solution. In preferred embodiments, a fluid-modifying reagent is considered free of endotoxins, at least ≤2 EU/mL endotoxin, at least <0.12 EU/mL).

In some embodiments, a fluid-modifying reagent does not induce a measurable inflammatory response in cells over the duration of an experiment. Therefore, in some embodiments, a fluid-modifying reagent used in a blood substitute does not induce a measurable inflammatory response in cells suspended in a solution comprising a fluid-modifying reagent. Moreover, in some embodiments, a fluid-modifying reagent used in a blood substitute does not induce a measurable inflammatory response in cells growing within a microfluidic chip, such cells include but are not limited to endothelial cells, parenchymal cells, etc. Thus in some embodiments, a fluid-modifying reagent used in a blood substitute is contemplated to be a reagent routinely used for density gradient separation of human blood cells, such as colloid materials, including but not limited to Percoll. Indeed, a variation of the colloid materials are contemplated for use, such as silane-coated particles; a nonionic density gradient medium; Nonionic Iodinated Density Gradient Media; Iodixanol (OptiPrep™); Nycodenz® D2158 Sigma, Histodenz™; Histopaque® (polysucrose and sodium diatrizoate) (Sigma-Aldrich Co. LLC); Colloidal Silica Media; Inorganic Salts; Polyhydric alcohols; Polysaccharides; etc.

In some embodiments, a fluid-modifying reagent is a solution, for example, polysucrose and sodium diatrizoate, adjusted to a density of 1.077 g/mL.

Percoll® refers to colloidal silica coated with polyvinylpyrrolidone (PVP). Percoll consists of colloidal silica particles of 15-30 nm diameter (23% w/w in water) which have been coated with polyvinylpyrrolidone (PVP). Percoll® PLUS is a silica-based colloidal medium for cell separation by density gradient centrifugation. The silane coating provides low osmolality and toxicity, as well as low viscosity. Percoll PLUS has low levels of endotoxins. After adjustment, Percoll PLUS forms iso-osmotic gradients within the density range of 1.0 to 1.3 g/ml. This density range is useful since most cells, subcellular particles, and viruses have a buoyant density of 1.0 to 1.2 g/ml in Percoll PLUS, Sigma-Aldrich Co. LLC.

Metrizamide is an example of a fluid-modifying reagent providing increasing density without increasing viscosity. Synonym: 2-[3-Acetamido-5-(N-methylacetamido)-2,4,6-triiodobenzamido]-2-deoxy-D-glucose, Metrizamide, mixture of anomers.

VI. Exemplary Methods of Immune Cell Recruitment.

The following Sections (i.e. steps) were used for providing immune cell recruitment assays on-chip using intestine on-chip. In some embodiments, inflammation is induced in a microfluidic intestine on-chip by inducing inflammation with cytokines.

Section 1: Inflammatory stimulation of Intestine-Chip: cytokine induced inflammation.

Seed Intestine-Chip following general protocol; At day 5, divide all of the chips into at least two subgroups: 1) Controls—which will not be treated with the inflammatory stimuli, and 2) Inflamed by treatment for 4-24 hours with an inflammatory stimuli such as TNF-alpha, IL-beta or LPS. Then, aspirate the media in both output Reservoirs and input Reservoir of the Bottom Channel; Induce vascular inflammation in the Intestine-chip. In one embodiment, vascular inflammation is triggered by perfusing fresh EGM2-MV media, with an inflammatory stimuli added, through the Bottom Channel. Perfuse EGM2-MV media+/– inflammatory stimuli through the Bottom Channel of Intestine-Chip at 60 ul/h for 4-24 hours. In one preferred embodiment, stimulation is 24 hours. For the control, media without an inflammatory stimuli is used instead. In one embodiment to induce vascular inflammation in the Intestine-Chip a mix of cytokines at the clinically relevant concentrations (Cytomix: 50 pg/ml, IL-1B, 215 pg/ml, TNFalpha and 200 pg/ml IL-6) similar to the levels observed in the blood of chronically diseased patients is used. The choice of the inflammatory stimulus, composition of Cytomix and their concentrations can be adjusted dependently on the needs of the specific application.

FIGS. 22A-B shows exemplary florescent microscope images and graphs demonstrating induction of adhesion molecule expression in intestinal endothelial cells on-chip after induction of inflammation using clinically relevant levels of cytokines. FIG. 22A ICAM-1 (pink) and nuclei (blue) stained channels (left) and under higher magnification (right) for control (upper) and inflamed (lower) channels. FIG. 22B shows a graphical comparison of relative mRNA expression for E-selectin, VCAM1, MadCAM1 and ICAM-1. Cells on-chip were treated for 24 hours with a Cytomix Formulation: TNF-alpha 10 U/ml (approximately 215 pg/ml), IL-1beta approximately 50 U/ml (approximately 50 pg/ml), IL-6 20 U/ml (approximately 200 pg/ml). U=units.

In other embodiments, Intestine On-Chip respond to low levels of cytokines present in the blood of chronically diseased patients by increased expression of adhesion molecules, See Table 11.

TABLE 11

Induction of Inflammation Using Clinically Relevant Levels of Cytokines: Experimental conditions vs. clinical relevance.

| Cytokine | Serum Concentration [pg/ml] | | Chip Stimulation [pg/ml] |
|---|---|---|---|
| | Healthy | Crohn's Disease | |
| IL-1β | 17.4 [11-26] | 47.1 [32-87] | 50 |
| IL-6 | 120.3 [110-128] | 177.4 [131-297] | 200 |
| TNFα | 179.2 [144-196] | 193.0 [179-221] | 215 |

* Vasilyeva et al. Mediators of Inflammation. 2016 for off chip results.

Luminal stimulation with a stimuli is another embodiment for inducing an Inflamed Intestine-Chip. As one non-limiting example cholera toxin is added into the epithelial cell media.

Section 2: Preparation of immune cells:

Thaw the frozen vial containing PBMC's (3×1^6 cells for 24 chip experiment) in the water bath. Resuspend the cells in 10 ml of media, spin down at 400×g/5 min/RT Remove the supernatant and resuspend the cells in 5 uM Cell Tracker Red CMPTX (Cat #C34552) staining solution prepared by diluting 10 ul of 5 mM stock solution in 10 ml of RPMI media (with 5% FBS). Incubate the cells at 37C (in a water bath) for 15-20 min protected from light. Add 40 ml of RPMI media to absorb any unload dye. Incubate for additional 5 min at 37 C (in a water bath) protected from light. Spin down the cells at 400×g/5 min/RT.

In some embodiments, an inflammatory intestine on-chip prepared in Section 1 and Section 2, combined with methods in Section 4, is used for modeling inflammation. However, in part due to challenges with controlling shear forces and rates, as described herein, in addition to the discovery that a 50% Percoll liquid lowered shear in a manner allowing maximal attachment of white blood cells, as opposed to 15% and 75% Percoll liquid solutions. Therefore, a 50% Percoll solution Section (step) was added Section 3: Addition of the Percoll Solution to immune cells (PBMC's):

Prepare 50% Percoll solution in RPMI media by mixing stock Percoll solution and RPMI media 1:1 (vol/vol) e.g. 10 ml of Percoll with 10 ml of RPMI media; in some embodiment, degass solutions using a steri-flip. Add 50% Percoll/RPMI solution to the cells to achieve final cell concentration of 2×10^6 cells/ml.

Section 4: Recruitment assay:

Add PBMC's as a cell suspension in 50% Percoll/RPMI into the Input Reservoir of the Bottom Channel, while in the Input Reservoir of the Top Channel add appropriate epithelial cell media (see Porotocol for Small Intestine-Chip). Perfuse the immune cell solution through the Bottom Channel at the Shear Stress of ~2 dyn/cm2 (flow rate~1200 ul/h) for 15 min. Aspirate media in both output Reservoirs. Add fresh RPMI media of Input Reservoirs of the Bottom Channel. Perfuse the Bottom Channel with RPMI media for additional 15 min at high flow rate of 1200 ul/h to remove cells that didn't adhere to the endothelial cell surface.

Section 5: Assessment of the immune cells recruitment:

Image the cells that attached to endothelial cells using Immunofluorescent or Confocal Microscope (endothelial cells can be co-stained using Wheat Germ Agglutinin (WGA), if assessment needs to be performed in the life cells or VE-cadherin or other staining specific for endothelial cells, if post-fixation assessment is preferred) Immune Cells can be co-stained for CD14 or CD3 markers in order to differentiate them into different subpopulations of monocytes and lymphocytes, respectively Chips can be lysed in order to assess endothelial or immune cells gene expression Effluents can be collected from the Top and Bottom Output Reservoirs in order to assess cytokines and chemokines released by the cells.

After assessment of immune cell recruitment chips can be terminated by the fixation with 4% PFA or can be maintained in culture under the normal flow conditions of 60 ul/h for their further assessment, including studies of immune cell translocation into the epithelial channel, contribution of immune cells to Intestine-Chip response to luminally applied stimuli etc.

VII. Embodiments of Microfluidic Chip Systems.

According to aspects of the present inventions, a microfluidic chip system is provided for determining a response of cells in a fluid medium comprising a modifying reagent.

According to aspects of the present inventions, a microfluidic chip system is provided for determining a response of cells in a fluid medium comprising a modifying reagent. It is not meant to limit a microfluidic chip system to one type, indeed, a variety of microfluidic chip systems, a variety of microfluidic chip geometries, and a variety of microfluidic chip configurations are contemplated. Exemplary non-limiting examples are provided herein, and described in patent documents including but not limited to those described in U.S. Pat. No. 8,647,861; PCT/US17/49115; each of which are herein incorporated by reference in their entirety.

Figure 1A:
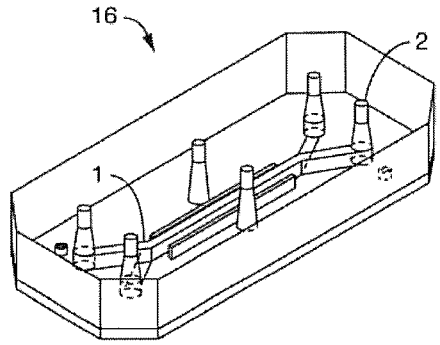
FIG. 1A shows one embodiment of the microfluidic device or chip (16), showing two channels (1), each with an inlet and outlet port (2), as well as (optional) vacuum ports—two upright structures in the middle of the chip.

FIG. 1A shows one embodiment of the microfluidic device or chip, showing two channels, each with an inlet and outlet port, as well as (optional) vacuum ports.

Figure 1B:
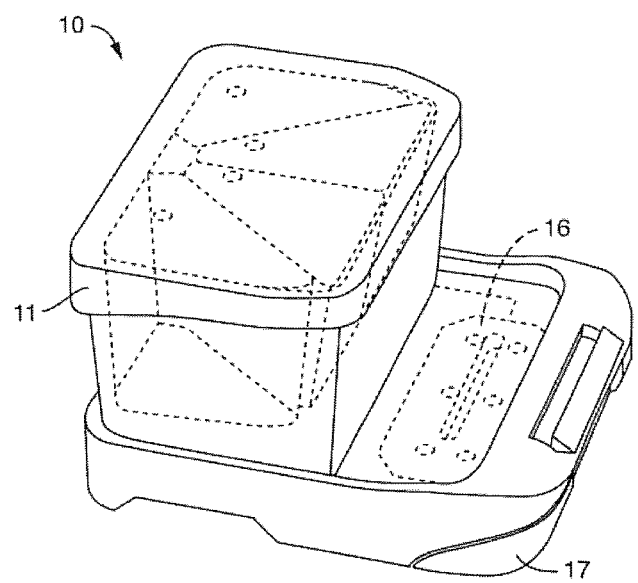
FIG. 1B is a topside schematic of one embodiment of the perfusion disposable or "pod" (10) featuring the transparent (or translucent) cover (11) over the reservoirs, with the chip

FIG. 1B is a topside schematic of one embodiment of the perfusion disposable or "pod" featuring the transparent (or translucent) cover over the reservoirs, with the chip inserted. The chip can be seeded with cells and then placed in a carrier for insertion into the perfusion disposable.

FIG. 2A shows a side view of one embodiment of a chip carrier (with the chip inside) approaching (but not yet engaging) a side track of a skirt of one embodiment of the perfusion manifold assembly, the carrier aligned at an angle matching an angled front end portion of the side track, the carrier comprising a retention mechanism configured as a upwardly protecting clip. Without being bound by theory, a suitably large angle permits chip engagement without smearing or premature engagement of liquid droplets present on the chip and/or the perfusion manifold assembly during the insertion and alignment processes.

FIG. 2B shows a side view of one embodiment of a chip carrier (with the chip inside) engaging a sidetrack of a skirt of one embodiment of (but not yet linked to) the perfusion manifold assembly.

FIG. 2C shows a side view of one embodiment of a chip carrier (with the chip inside) fully engaging a side track of a skirt of one embodiment of (but not yet linked to) the perfusion manifold assembly (with an arrow showing the necessary direction of movement to get a snap fit whereby the retention mechanism will engage to prevent movement).

FIG. 2D shows a side view of one embodiment of a chip carrier (with the chip inside) detachably linked to the perfusion manifold assembly, where the retention mechanism is engaged to prevent movement.

FIG. 3 is a schematic of one embodiment of a work flow (with arrows showing each progressive step), where the chip is linked (e.g. snapped in) to a disposable perfusion manifold assembly ("perfusion disposable"), which in turn is positioned with other assemblies on a culture module, which is placed in an incubator.

FIG. 4 is a schematic of another embodiment showing the tray (or rack) and sub-tray (or nest) for transporting and inserting the perfusion disposables (PDs) into the pressure module, which has a user interface on outside of the housing.

FIG. 5A is a schematic of the interior of one embodiment of the pressure module (in an open position), showing the positioning of the tray (or rack), sub-tray (or nest), perfusion disposables (PDs) under a pressure manifold (but not engaging it, so the clearance is sufficient to remove them), with the actuation assembly (including the pneumatic cylinder) above. Three microfluidic devices or perfusion disposables are shown to illustrate, although more (e.g. 6, 9 or 12) are typically used at once.

FIG. 5B is a schematic of the interior of one embodiment of the pressure module (in a closed position), showing the positioning of the tray (or rack), sub-tray (or nest), perfusion disposables (PDs) under the pressure manifold (and engaging it), with the actuation assembly (including the pneumatic cylinder) above. Again, three microfluidic devices or perfusion disposables are shown to illustrate, although more (e.g. 6, 9 or 12) are typically used at once.

FIG. 6A illustrates a perspective view of one embodiment of a microfluidic device with enclosed microfluidic channels as a CAD image.

FIG. 6B illustrates an exploded view of one embodiment of a microfluidic device (showing a microfluidic channel in a top piece and a microfluidic channel in a bottom piece, separated by a membrane).

VIII. Chip Activation.

A. Chip Activation Compounds.

In one embodiment, bifunctional crosslinkers are used to attach one or more extracellular matrix (ECM) proteins. A variety of such crosslinkers are available commercially, including (but not limited to) the following compounds:

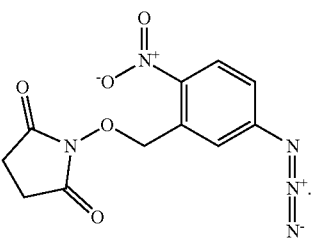

ANB-NOS (N-5-azido-2-nitrobenzoyloxysuccinimide)

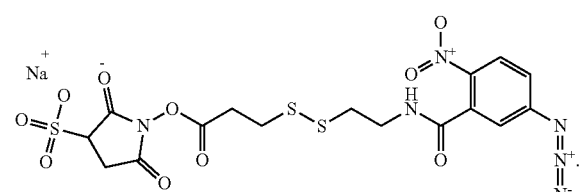

Sulfo-SAND (sulfosuccinimidyl 2-[m-azido-o-nitrobenzamido]ethyl-1, 3′-dithiopropionate)

-continued

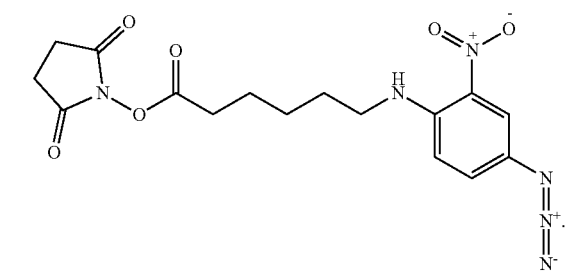

SANPAH
(N-succinimidyl-6-[4′-azido-2′-nitrophenylamino]hexanoate)

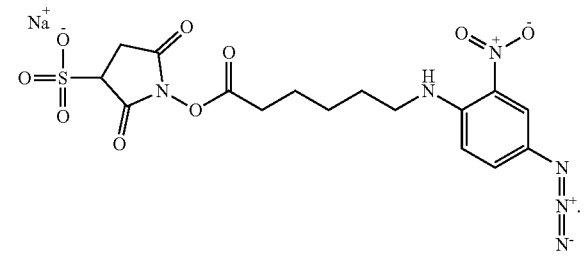

Sulfo-SANPAH
(sulfosuccinimidyl-6-[4′-azido-2′-nitrophenylamino]hexanoate)

By way of example, sulfosuccinimidyl 6-(4′-azido-2′-nitrophenyl-amino) hexanoate or "Sulfo-SANPAH" (commercially available from Pierce) is a long-arm (18.2 angstrom) crosslinker that contains an amine-reactive N-hydroxysuccinimide (NHS) ester and a photoactivatable nitrophenyl azide. NHS esters react efficiently with primary amino groups ($-NH_2$) in pH 7-9 buffers to form stable amide bonds. The reaction results in the release of N-hydroxy-succinimide. When exposed to UV light, nitrophenyl azides form a nitrene group that can initiate addition reactions with double bonds, insertion into C—H and N—H sites, or subsequent ring expansion to react with a nucleophile (e.g., primary amines). The latter reaction path dominates when primary amines are present.

Sulfo-SANPAH should be used with non-amine-containing buffers at pH 7-9 such as 20 mM sodium phosphate, 0.15M NaCl; 20 mM HEPES; 100 mM carbonate/bicarbonate; or 50 mM borate. Tris, glycine or sulfhydryl-containing buffers should not be used. Tris and glycine will compete with the intended reaction and thiols can reduce the azido group.

For photolysis, one should use a UV lamp that irradiates at 300-460 nm. High wattage lamps are more effective and require shorter exposure times than low wattage lamps. UV lamps that emit light at 254 nm should be avoided; this wavelength causes proteins to photodestruct. Filters that remove light at wavelengths below 300 nm are ideal. Using a second filter that removes wavelengths above 370 nm could be beneficial but is not essential.

B. Exemplary methods of Chip Activation.

Prepare and sanitize hood-working space.

1. Chip Handling: Use Aseptic Technique, Hold Chip using Carrier
   a. Use 70% ethanol spray and wipe the exterior of Chip package prior to bringing into hood
   b. Open package inside hood
   c. Remove Chip and place in sterile petri dish (6 Chips/Dish)
   d. Label Chips and Dish with respective condition and Lot #

2. Surface Activation with Chip Activation Compound (Light and Time Sensitive)
   a. Turn off light in biosafety hood
   b. Allow vial of Chip Activation Compound powder to fully equilibrate to ambient temperature (to prevent condensation inside the storage container, as reagent is moisture sensitive)
   c. Reconstitute the Chip Activation Compound powder with ER-2 solution
      i. Add 10 ml Buffer, such as HEPES, into a 15 ml conical covered with foil
      ii. Take 1 ml Buffer from above conical and add to chip Activation Compound (5 g) bottle, pipette up and down to mix thoroughly and transfer to same conical
      iii. Repeat 3-5 times until chip Activation Compound is fully mixed
      iv. NOTE: Chip Activation Compound is single use only, discard immediately after finishing Chip activation, solution cannot be reused
   d. Wash channels
      i. Inject 200 ul of 70% ethanol into each channel and aspirate to remove all fluid from both channels
      ii. Inject 200 ul of Cell Culture Grade Water into each channel and aspirate to remove all fluid from both channels
      iii. Inject 200 ul of Buffer into each channel and aspirate to remove fluid from both channels
   e. Inject Chip Activation Compound Solution (in buffer) in both channels
      i. Use a P200 and pipette 200 ul to inject Chip Activation Compound/Buffer into each channel of each chip (200 ul should fill about 3 Chips (Both Channels))
      ii. Inspect channels by eye to be sure no bubbles are present. If bubbles are present, flush channel with Chip Activation Compound/Buffer until bubbles have been removed
   f. UV light activation of Chip Activation Compound Place Chips into UV light box
      i. UV light treat Chips for 20 min While the Chips are being treated, prepare ECM Solution.
      ii. After UV treatment, gently aspirate Chip Activation Compound/Buffer from channels via same ports until channels are free of solution
      iii. Carefully wash with 200 ul of Buffer solution through both channels and aspirate to remove all fluid from both channels
      iv. Carefully wash with 200 ul of sterile DPBS through both channels
      v. Carefully aspirate PBS from channels and move on to: ECM-to-Chip IX. ECM-to-Chip.
1. Calculate Total Volume of ECM Solution Needed to Coat Chips
   a. Volume required per Chip=50 ul/Channel
   b. ECM diluent: PBS, prepared on ice
      i. Stock Concentrations for ECM coating:
         1. Collagen IV: 1 mg/ml (200 ul aliquots in −20 C)
         2. Fibronectin: 1 mg/ml (50 ul aliquots in 4 C)
         3. Matrigel: 10 mg/ml (200 ul aliquots in −20C)
      ii. Working Concentrations for ECM coating:
         1. Collagen IV: 200 ug/ml
         2. Fibronectin: 30 ug/ml
      iii. Top Channel Coating: 50 ul Collagen IV (200 ug/ml) and Matrigel (100 ug/ml)
      iv. Bottom Channel Coating: 50 ul Collagen IV (200 ug/ml) and Fibronectin (3 ug/ml)
2. Load Channels with ECM Solution
   a. Place Chips in hood
   b. Pipette 50 ul of Top Channel Coating into Top Channel—keep the pipette plunger depressed until you see fluid come out opposite end of the channel, then take another pipette tip (200 ul tip) to close the outlet port. Once closed off, carefully remove the pipette tip, leaving the tip in the inlet port.
   c. Aspirate excess fluid from the surface of Chip (avoid direct contact with the port)
   d. Repeat 2b-2c, but with Bottom Channel Coating into Bottom Channel
3. Incubate at 37C for a Minimum of 2 Hours up to Overnight X. Exemplary Matrigel Coating
Thaw Matrigel on ice and keep chilled to prevent solidification.
   a. Prepare Matrigel
      i. Matrigel Stock Concentration: 10 mg/ml
      ii. Matrigel Final Concentration: 250 ug/ml
      iii. Determine the volume of Matrigel needed to coat 50 ul of each Top Channel and resuspend accordingly in cell culture media
   b. Transfer the NUFFs-seeded Chips into the hood
   c. Wash both channels of each chip twice with 200 ul media
   d. Before inserting the tips, add a drop of media to prevent formation of bubbles
   e. Leave 50 ul media in bottom channel (Tips inserted)
   f. Add 50 ul 250 ug/ml matrigel to top channel (Tips inserted)
   g. Incubate at 37 C overnight XI. Cells-to-Chip Chip Preparation.
   a. Transfer the ECM coated Chips into the hood
   b. Gently wash Chips after ECM coating
   c. Pipette 200 ul of DPBS into bottom channel inlet port—keep the pipette plunger depressed until you see fluid come out opposite end of channel and aspirate outflow
   d. Repeat the same procedure to wash top channel
   e. Pipette 200 ul of DPBS into top channel inlet port—keep the pipette plunger depressed until you see fluid come out opposite end of the channel, then take another pipette tip (200 ul) to close the outlet port. Once closed off, carefully remove the pipette tip, leaving the tip in the inlet port.
   f. Repeat the same with the bottom channel. Place back in incubator until cells are ready.

Accordingly, in accordance with some embodiments of the invention, the membrane can be subjected to physiological mechanical strain generated by cyclic stretching and retracting of the membrane and/or the flow of biological fluids (e.g. air, mucus, blood, culture medium) in either one or both of the first central microchannel and second central microchannel to recapitulate the native microenvironment of a tissue or an organ to be mimicked. In accordance with some embodiments of the invention, the culture conditions of cells upon the membrane can be optimized under extracellular matrix (ECM) coating, media perfusion, and/or mechanical strain to maintain morphological and functional characteristics of the cultured cells and to permit their direct cellular interaction across the membrane. The device described herein can thus permit long-term cell culture and optional dynamic mechanical stimulation of adjacent monolayers or multi-layers of cells grown on the membrane at the same time. Some examples and aspects of systems and methods for mechanical stretch actuation and imparting strains to microfluidic devices, including microfluidic devices with microchannels and/or membranes with cells disposed thereon, are provided in PCT/US2014/071570 published as WO2015138032 (Sep. 17, 2015) "Organomimetic devices and methods of use and manufacturing thereof".

Additional embodiments of microfluidic chips and microfluidic systems that may find use with fluids comprising modifying reagents, are described in part in: PCT/US2016/026831 published as WO2016168091 "Microfluidic device having offset, high-shear seeding channels", herein incorporated by reference in its entirety; PCT/US2016/022928 published as WO2016149527 (Sep. 22, 2016 "Incubating enclosure", herein incorporated by reference in its entirety; PCT/US2016/064813 published as WO2017096296 (Jun. 8, 2017) "Clamping system for a microfluidic assembly", herein incorporated by reference in its entirety; PCT/US2016/025228 published as WO2016161090 (Oct. 6, 2016) "Respiration device for analysis of a response to shear stress and foreign agents on cells", herein incorporated by reference in its entirety; etc.

Numerous types of microfluidic chips may be used with a biomimetic fluid surrogate including but not limited to those as described herein and in referenced publications, etc. In some embodiments, a biomimetic fluid surrogate is used for thrombosis modeling, as described herein and in PCT Application PCT/US17/041668 filed 2017, herein incorporated by reference in its entirety. These exemplary chips may have alternative options, such as closed chips, open to chips, etc., as briefly described herein and in U.S. Pat. No. 8,647,861, herein incorporated by reference in its entirety; and as described herein.

Moreover, microfluidic chips may be used with a biomimetic fluid surrogate, e.g. a blood substitute, includes a microfluidic system for simulating a heart valve, as one example, PCT/US2017/017980 published as WO2017142950 (Aug. 24, 2017) "Microfluidic device for shear flow testing and methods for using the same", herein incorporated by reference in its entirety.

A. Additional Embodiments of Open Top Chips.

The present disclosure relates to microfluidic chips, such as fluidic devices comprising one or more cell types for the simulation one or more of the function of organ components. Accordingly, the present disclosure additionally describes open-top chips, see, e.g. schematic in FIG. 6A-B. FIG. 6B shows an exemplary exploded view of one embodiment of an open-top chip device 1800, wherein a membrane 1840 resides between the bottom surface of the first chamber 1863 and the second chamber 1864 and the at least two spiral microchannels 1851. Open top microfluidic chips include but are not limited to chips having removable covers, such as removable plastic covers, paraffin covers, tape covers, etc.

Many of the problems associated with earlier systems can be solved by providing an open-top style microfluidic device that allows topical access to one or more parts of the device or cells that it comprises. For example, the microfluidic device can include a removable cover, that when removed, provides access to the cells of interest in the microfluidic device. In some aspects, the microfluidic devices include systems that constrain fluids, cells, or biological components to desired area(s). The improved systems provide for more versatile experimentation when using microfluidic devices, including improved application of treatments being tested, improved seeding of additional cells, and/or improved aerosol delivery for select tissue types.

It is also desirable in some aspects to provide access to regions of a cell-culture device. For example, it can be desirable to provide topical access to cells to (i) apply topical treatments with liquid, gaseous, solid, semi-solid, or aerosolized reagents, (ii) obtain samples and biopsies, or (iii) add additional cells or biological/chemical components Therefore, the present disclosure relates to fluidic systems that include a fluidic device, such as a microfluidic device with an opening that provides direct access to device regions or components (e.g. access to the gel region, access to one or more cellular components, etc.). Although the present disclosure provides an embodiment wherein the opening is at the top of the device (referred to herein with the term "open top"), the present invention contemplates other embodiments where the opening is in another position on the device. For example, in one embodiment, the opening is on the bottom of the device. In another embodiment, the opening is on one or more of the sides of the device. In another embodiment, there is a combination of openings (e.g. top and sides, top and bottom, bottom and side, etc.).

While detailed discussion of the "open top" embodiment is provided herein, those of ordinary skill in the art will appreciate that many aspects of the "open top" embodiment apply similarly to open bottom embodiments, as well as open side embodiments or embodiments with openings in any other regions or directions, or combinations thereof. Similarly, the device need not remain "open" throughout its use; rather, as several embodiments described herein illustrate, the device may further comprise a cover or seal, which may be affixed reversibly or irreversibly. For example, removal of a removable cover creates an opening, while placement of the cover back on the device closes the device. The opening, and in particular the opening at the top, provides a number of advantages, for example, allowing (i) the creation of one or more gel layers for simulating the application of topical treatments on the cells, tissues, or organs, or (ii) the addition of chemical or biological components such as the seeding of additional cell types for simulated tissue and organ systems. The present disclosure further relates to improvement in fluidic system(s) that improve the delivery of aerosols to simulated tissue and organ systems, such as simulated gastrointestinal tissues.

The present invention contemplates a variety of uses for these open top microfluidic devices and methods described herein. In one embodiment, the present invention contemplates a method of topically testing an agent (whether a drug, food, gas, or other substance) comprising 1) providing a) an agent and b) microfluidic device comprising i) a chamber, said chamber comprising a lumen and projections into the lumen, said lumen comprising ii) a gel matrix anchored by said projections and comprising cell in, on or under said gel matrix, said gel matrix positioned above iii) a porous membrane and under iv) a removable cover, said membrane in contact with v) fluidic channels; 2) removing said removable cover; and 3) topically contacting said cells in, on or under said gel matrix with said agent. In one embodiment, said agent is in an aerosol. In one embodiment, agent is in a liquid, gas, gel, semi-solid, solid, or particulate form. These uses may apply to the open top microfluidic chips described below and herein.

FIG. 6A illustrates a perspective view of one embodiment of a microfluidic device with enclosed microfluidic channels as a CAD image.

FIG. 6B illustrates an exploded view of one embodiment of a microfluidic device (showing a microfluidic channel in a top piece and a microfluidic channel in a bottom piece, separated by a membrane).

FIG. 7A-D shows schematic drawings and exemplary micrographs of cell growing in an exemplary open top chip. In one embodiment, a skin on-chip is an exemplary open top chip. FIG. 7A shows a schematic of one embodiment of an open top chip. FIG. 7B shows a side view schematic as a cross section of one embodiment of an open top chip. FIG. 7C shows a schematic of one embodiment of a lower circular channel simulating a blood vessel located in the bottom of the chip. FIG. 7D shows a schematic of one embodiment of an open top chip comprising a keratinocyte layer in the top fluidic channel (micrograph of keratinocyte layer on the upper left) and a lower dermal area underneath (micrograph of growing cells in the dermal area (layer) on the lower left).

FIG. 8A-D Shows exemplary schematic illustrations of additional types of chips (i.e. geometries) that may be used with fluids comprising fluid modifying reagents. FIG. 8A Shows an exemplary schematic illustration of a circular format (geometry) for a microfluidic chip. FIG. 8B Shows exemplary photographs of a side view (upper) and top view (lower) circular chip. FIG. 8C Shows an exemplary schematic illustration of a rectangular format (geometry) for a microfluidic chip. FIG. 8D Shows exemplary photograph of a top view of a rectangular chip.

Fluids containing modifying agents, such as a modified fluid as a blood substitute, a modified fluid as a mucosal substitute, a modified fluid as a blood substitute, a modified fluid as a tubule fluid substitute, or any type of fluid substitute in contact with the exterior of a cell layer, etc., e.g. having an addition of Percoll or other fluid-modifying reagent, includes but is not limited) to Lung, the Small Airway, the gut, muscle (including skeletal, cardiac and or smooth muscle, and the Blood Brain Barrier (BBB). Both human and animal cells are contemplated. Cell types which can be used in the open-top devices include, but are not limited to Wet stratified barrier epithelial cells, such as Surface epithelial cell of stratified squamous epithelium of cornea, tongue, oral cavity, esophagus, anal canal, distal urethra and vagina, basal cell (stem cell) of epithelia of cornea, tongue, oral cavity, esophagus, anal canal, distal urethra and vagina, Urinary epithelium cell (lining urinary bladder and urinary ducts); Exocrine secretory epithelial cells, such as Salivary gland mucous cell (polysaccharide-rich secretion), Salivary gland serous cell (glycoprotein enzyme-rich secretion), Von Ebner's gland cell in tongue (washes taste buds), Mammary gland cell (milk secretion), Lacrimal gland cell (tear secretion), Ceruminous gland cell in ear (wax secretion), Eccrine sweat gland dark cell (glycoprotein secretion), Eccrine sweat gland clear cell (small molecule secretion), Apocrine sweat gland cell (odoriferous secretion, sex-hormone sensitive), Gland of Moll cell in eyelid (specialized sweat gland), Sebaceous gland cell (lipid-rich sebum secretion), Bowman's gland cell in nose (washes olfactory epithelium), Brunner's gland cell in duodenum (enzymes and alkaline mucus), Seminal vesicle cell (secretes seminal fluid components, including fructose for swimming sperm), Prostate gland cell (secretes seminal fluid components), Bulbourethral gland cell (mucus secretion), Bartholin's gland cell (vaginal lubricant secretion), Gland of Littre cell (mucus secretion), Uterus endometrium cell (carbohydrate secretion), Isolated goblet cell of respiratory and digestive tracts (mucus secretion), Stomach lining mucous cell (mucus secretion), Gastric gland zymogenic cell (pepsinogen secretion), Gastric gland oxyntic cell (hydrochloric acid secretion), Pancreatic acinar cell (bicarbonate and digestive enzyme secretion), pancreatic endocrine cells, Paneth cell of small intestine (lysozyme secretion), intestinal epithelial cells, Types I and II pneumocytes of lung (surfactant secretion), and/or Clara cell of lung. In some embodiments, such devices have structural anchors for mimicking In fact, in addition to a fluid substitute for mucosal surfaces, in part for identifying paracrine and autocrine factor diffusion and action under specific types of mucosal viscosities, densities, etc., fluid substitutes are contemplated to be provided to as physiological mimics of fluids within tubules, such as tubules conducting hormones from hormone secreting cells, such as such as endocrine cells of the islet of Langerhands of the pancreas, Anterior pituitary cells, Somatotropes, Lactotropes, Thyrotropes, Gonadotropes, Corticotropes, Intemiediate pituitary cell, secreting melanocyte-stimulating hormone; and Magnocellular neurosecretory cells secreting oxytocin or vasopressin; Gut and respiratory tract cells secreting serotonin, endorphin, somatostatin, gastrin, secretin, cholecystokinin, insulin, glucagon, bombesin; Thyroid gland cells such as thyroid epithelial cell, parafollicular cell, Parathyroid gland cells, Parathyroid chief cell, Oxyphil cell, Adrenal gland cells, chromaffin cells secreting steroid hormones (mineralcorticoids and gluco corticoids), Leydig cell of testes secreting testosterone, Theca interna cell of ovarian follicle secreting estrogen, Corpus luteum cell of ruptured ovarian follicle secreting progesterone, Granulosa lutein cells, Theca lutein cells, Juxtaglomerular cell (renin secretion), Macula densa cell of kidney, Peripolar cell of kidney, and/or Mesangial cell of kidney. PCT/US2016/064814 published as WO2017096297 (Jun. 8, 2017) "Open-top microfluidic device with structural anchors."

B. Additional Embodiments of Closed Top Chips.

FIG. 9A-B illustrates a perspective view of the tissue interface device in accordance with an embodiment. In particular, as shown in FIG. 9A, the device or chip 200 preferably includes a body 202 having a branched microchannel design 203, showing input and output ports (211; 215), including a plurality of ports 205; in fluidic communication with an active region or experimental region (A) a tissue-tissue interface simulation region (membrane 208 in FIG. 9B) of microchannels (203) with optional vacuum chambers (252) in accordance with an embodiment.

The body 202 is preferably made of a flexible biocompatible polymer, including but not limited to, polydimethyl siloxane (PDMS), or polyimide. It is also contemplated that the body 202 may be made of non-flexible materials like glass, silicon, hard plastic, and the like. Although it is preferred that the interface membrane be made of the same material as the body 202, it is contemplated that the interface membrane be made of a material that is different than the body of the device. It should be noted that the microchannel design 203 is only exemplary and not limited to the configuration shown in FIG. 9A or FIG. 9B. The device in FIG. 9A includes a plurality of ports 205 which will be described in more detail below. In addition, the branched configuration 203 includes a tissue-tissue interface simulation region (membrane 208, opposing sides A and B, in FIG. 9B) where cell behavior and/or passage of gases, chemicals, molecules, particulates and cells are monitored.

FIG. 9B illustrates an exploded view of the microfluidic device of FIG. 9A. See further information on part numbers described herein.

FIG. 9B illustrates an exploded view of the organ mimic device in accordance with an embodiment. In particular, the outer body 202 of the device 200 is preferably comprised of a first outer body portion 204, a second outer body portion 206 and an intermediary porous membrane 208 configured to be mounted between the first and second outer body portions 204, 206 when the portions 204, 206 are mounted to one another to form the overall body.

FIG. 9B illustrates an exploded view of the device in accordance with an embodiment. As shown in FIG. 9B, the first outer body portion 204 includes one or more inlet fluid ports 210 preferably in communication with one or more corresponding inlet apertures 211 located on an outer surface of the body 202. The device 100 is preferably connected to the fluid source 104 via the inlet aperture 211 in which fluid travels from the fluid source 104 into the device 100 through the inlet fluid port 210.

Additionally, the first outer body portion 204 includes one or more outlet fluid ports 212 preferably in communication with one or more corresponding outlet apertures 215 on the outer surface of the body 202. In particular, fluid passing through the device 100 exits the device 100 to a fluid collector 108 or other appropriate component via the corresponding outlet aperture 215. It should be noted that the device 200 may be set up such that the fluid port 210 is an outlet and fluid port 212 is an inlet. Although the inlet and outlet apertures 211, 215 are shown on the top surface of the body 202, one or more of the apertures may be located on one or more sides of the body.

In an embodiment, the inlet fluid port 210 and the outlet fluid port 212 are in communication with the first central microchannel 250A (see FIG. 3A) such that fluid can dynamically travel from the inlet fluid port 210 to the outlet fluid port 212 via the first central microchannel 250A, independently of the second central microchannel 250B.

It is also contemplated that the fluid passing between the inlet and outlet fluid ports may be shared between the central sections 250A and 250B. In either embodiment, characteristics of the fluid flow, such as flow rate and the like, passing through the central microchannel 250A is controllable independently of fluid flow characteristics through the central microchannel 250B and vice versa.

In addition, the first portion 204 includes one or more pressure inlet ports 214 and one or more pressure outlet ports 216 in which the inlet ports 214 are in communication with corresponding apertures 217 located on the outer surface of the device 100. Although the inlet and outlet apertures are shown on the top surface of the body 202, one or more of the apertures may alternatively be located on one or more sides of the body.

In some embodiments, fluidic devices having additive channels are contemplated for use in immune recruitment assays comprising a fluid-modifying agent.

FIG. 14 demonstrates one contemplated embodiment of fluidic device or chip (1900) having an anticoagulant ports (1932 and 1934) for use with a fluid-modifying agent, such as a blood substitute. Shown is a schematic of one embodiment of a microfluidic device, as in FIG. 9A, with the addition of an anticoagulant ports as additive channels (1932 and 1934 surrounding the OUTLET port 1917) (one on either side near at least one inlet or outlet port for which effluent anti-coagulation is desired). Arrows pointing to INLET ports 1910 and 1911 for upper and lower channels while other arrows point to OUTLET ports 1917 and 1915, respectively attached to inlet ports. The upper channel 1912 emerges from one INLET 1910. The lower channel 1914 emerges from underneath the upper channel attached to the lower Inlet 1911. Each of two microchannels terminates at a single port. Each microchannel attached to an anticoagulant port is in fluidic communication with two additive channels, each pair of additive channel connecting to a separate port (e.g. for adding the additive to the additive channel, i.e. ANTICOAGULANT port 1930). attached to the top microfluidic channel where the upper channel is also marked with an OUTLET at one end. In other embodiments, the lower vascular chamber has an anticoagulant port near the vascular outlet. An arrow points to the IMAGING area (active region) 1920 outlined with dotted lines.

C. Embodiments of Specific Microfluidic Chips.

FIGS. 10A-G shows an example of human primary airway cells cultured in a microfluidic Airway-on-Chip. FIG. 10A is a schematic representation of one embodiment of an Airway-on-Chip where cells seeded in the upper channel and grown with an air interface (blue), on top of a lower channel under media flow (red). FIG. 10B shows a colored scanning electron micrograph of ciliated cells, where cilia are artificially colored blue with non-ciliated cells artificially colored brown. FIG. 10C shows a still shot (video frame) of cilia beating (blurry cilia). FIG. 10D shows an immunofluorescent micrograph of Goblet cells (red stained mucine proteins with blue colored nuclei). FIG. 10E shows a still shot from a video micrograph of mucociliary transport (i.e. mucociliary escalator) where the white dots are fluorescent microbeads moving across the upper surface of the epithelium. FIG. 10F illustrates a perspective view of one embodiment of a cross section through the Airway Chip microfluidic device with showing its two hollow linear channels (air channel above; blood channel below) separated by a porous membrane which supports growth and differentiation of human primary airway epithelial cells on its upper surface and human pulmonary microvascular endothelial cells underneath.

FIGS. 11A-C shows an example of one embodiment of an Airway-on-Chip emulating acute asthma exacerbation by combining Rhinovirus infection with IL-13 stimulation in the presence of an exemplary immuno-modulatory compound: Neutrophil recruitment following exacerbation with HRV can be reduced by an exemplary CXCR2 antagonist MK-7123. FIG. 11A (upper image) shows one embodiment of an Airway-on-Chip that enables testing of immuno-modulatory compounds, e.g. for neutrophil recruitment, in a model of acute asthma exacerbation. HRV-16 is represented as small green dots in the upper channel while neutrophil cells (also described as polymorphonuclear leukocytes (PMN)) are represented as large purple spots in the lower channel. An enlarged schematic is demonstrated schematically in the lower image showing a HRV-infected Airway Chip during perfusion in the vascular channel of freshly isolated human neutrophil. FIG. 11B shows a series of fluorescent micrographs showing comparisons of stained neutrophil cells (red) recruited to the endothelium and attached to non-treated cells. Treatments included HRV-16 alone infected cells, IL-13 alone treated cells, HRV-16 and (+) IL-13 treated cells, HRV-16+CXCR2in (inhibitor) treated cells, and HRV-16+IL-13+CXCR2 in. Non-stimulated chips are showing limited neutrophil recruitment while HRV infected and IL-13-treated chips show increased neutrophil recruitment. IL-13+HRV induce an additive increase in neutrophil recruitment, while treatment with a CXCR2 antagonist. MK-7123 (10 microM) significantly reduced neutrophil recruitment under three stimulation conditions. FIG. 11C is a graphical comparison showing PMN (neutrophil) cells counts as % of untreated cells and cells treated with combinations shown for IL-13, HRV, and CXCR2 (in) treatments. Quantification of neutrophil recruitment ($p<0.01$; **$p<0.001$).

FIGS. 12A-D shows an example of one embodiment of an Airway-on-Chip demonstrating the effect of a CXCR2 antagonist (inhibitor: in) on neutrophil crawling and trans-migration of cells out of the endothelial channel. FIG. 12A is a micrograph showing effects of HRV-16 infected cells (24 hpi) on cell attachment and FIG. 13B shows effects of HRV-16 infected cells (24 hpi) treated with CXCR2 in (10 μM) on cell attachment. FIG. 12C shows a graph of the number of spots (i.e. neutrophil cells: N spots) counted over time (up to 300 seconds) for HRV-16 infected cells (24 hpi). FIG. 12D shows a graph of N spots counted over time (up to 600 seconds) for HRV-16 infected cells (24 hpi) treated with CXCR2in (10 μM).

FIGS. 11D-11I show exemplary schematics and data, showing viral-induced exacerbation on-chip inducing neutrophil transmigration, for use in on-chip testing of prophylactic treatments for reducing incidents of severe asthma attacks and for treatments during severe asthma attacks to reduce at least one symptom. FIG. 11D shows an exemplary schematic (as a Venn Diagram) where asthma induction as an inflamed airway is represented by IL-13 treatment (left circle) and viral exacerbation of asthma is represented by a rhinovirus (HRV) infection (right circle). The area of overlap represents asthma exacerbation in a patient or on-chip when both conditions are present. FIG. 11E shows an exemplary schematic of one embodiment of asthma exacerbation where a virus is infecting ciliated epithelial cells in the airway channel (green dots and green ciliated cells) which induces neutrophil (bumpy round cells) recruitment (attachment) and movement through the endothelium on the vascular channel, then as shown in FIG. 11F, neutrophils show extravasation through the porous membrane then into the airway side of the membrane, i.e. trans-epithelial migration. FIG. 11G shows one embodiment of a severe asthma chip enabling neutrophil diapedesis: HRV16 (24 hpi) infected cells visualized by immunofluorescent staining of Myeloperoxidase (MPO) stained neutrophils showing a Z-stack confocal microscopic image. FIG. 11H shows a colorized immunofluorescent image of HRV16 (24 hpi) infected cells stained with Myeloperoxidase (MPO) (green)/mAbJ2 (red)/DAPI (blue) where MPO+ cells are located near virally infected cells. And FIG. 11I shows a monoclonal antibody (mabJ2) (mouse) detecting double-strand RNA as an RNA replication-center assay for one embodiment of a high content image-based quantification of human rhinovirus and Coxsackie virus infections.

Experimental

The following examples illustrate some embodiments described herein. It will be apparent to those skilled in the relevant art that various modifications, additions, substitutions, and the like can be performed without altering the spirit or scope of the invention, and such modifications and variations are encompassed within the scope of the invention as defined in the claims described herein. The following examples do not in any way limit the invention.

Example 1

Exemplary Methods and Readouts (Assays)

Percoll/Medium.

In some embodiments, a Percoll liquid, e.g. media formulation of 50% is used in combination with assist immune recruitment assays On Chips, including but not limited to immune-cell types: PBMCs, white blood cells, lymphocytes, macrophages, neutrophils, B cells, T cells, killer cells, etc. Observe cells to assess morphology and viability: Capture representative images along the length of Chip, including but not limited to inlet junctions, outlet junctions, and center of Chip. Collect samples from the back side of the Reservoirs into pre-labeled tubes or 96 well plate.

Bright-Field Imaging:

As one example of a readout for comparative purposes, for use in drug testing, etc., Image Chips at Days 0, 2, 4, 6, 8, etc.

Example 2

Exemplary Methods of Immune Cell Recruitment

The following Sections (i.e. steps) were used for providing immune cell recruitment assays on-chip using intestine on-chip. In some embodiments, inflammation is induced in a microfluidic intestine on-chip by inducing inflammation with cytokines.

Section 1: Inflammatory stimulation of Intestine-Chip: cytokine induced inflammation.

Seed Intestine-Chip following general protocol; At day 5, divide all of the chips into at least two subgroups: 1) Controls—which will not be treated with the inflammatory stimuli, and 2) Inflamed by treatment for 4-24 hours with an inflammatory stimuli such as TNF-alpha, IL-1beta or LPS. Then, aspirate the media in both output Reservoirs and input Reservoir of the Bottom Channel; Induce vascular inflammation in the Intestine-chip. In one embodiment, vascular inflammation is triggered by perfusing fresh EGM2-MV media, with an inflammatory stimuli added, through the Bottom Channel. Perfuse EGM2-MV media+/− inflammatory stimuli through the Bottom Channel of Intestine-Chip at 60 ul/h for 4-24 hours. In one preferred embodiment, stimulation is 24 hours. For the control, media without an inflammatory stimuli is used instead. In one embodiment to induce vascular inflammation in the Intestine-Chip a mix of cytokines at the clinically relevant concentrations (Cytomix: 50 pg/ml, IL-1B, 215 pg/ml, TNF-alpha and 200 pg/ml IL-6) similar to the levels observed in the blood of chronically diseased patients is used. The choice of the inflammatory stimulus, composition of Cytomix and their concentrations can be adjusted dependently on the needs of the specific application.

FIGS. 20A-B shows exemplary florescent microscope images and graphs demonstrating induction of adhesion molecule expression in intestinal endothelial cells on-chip after induction of inflammation using clinically relevant levels of cytokines. FIG. 20A ICAM-1 (pink) and nuclei (blue) stained channels (left) and under higher magnification (right) for control (upper) and inflamed (lower) channels. FIG. 20B shows a graphical comparison of relative mRNA expression for E-selectin, VCAM1, MadCAM1 and ICAM-1. Cells on-chip were treated for 24 hours with a Cytomix Formulation: TNF-alpha 10 U/ml (approximately 215 pg/ml), IL-1beta approximately 50 U/ml (approximately 50 pg/ml), IL-6 20 U/ml (approximately200 pg/ml). U=units.

In other embodiments, Intestine On-Chip responds to low levels of cytokines present in the blood of chronically diseased patients by increased expression of adhesion molecules, See Table 11.

Section 2: Preparation of Immune Cells:

Thaw the frozen vial containing PBMC's ($3 \times 10^{\wedge}6$ cells for 24 chip experiment) in the water bath. Resuspend the cells in 10 ml of media, spin down at 400×g/5 min/RT Remove the supernatant and resuspend the cells in 5 uM Cell Tracker Red CMPTX (Cat #C34552) staining solution prepared by diluting 10 ul of 5 mM stock solution in 10 ml of RPMI media (with 5% FBS). Incubate the cells at 37 C (in a water bath) for 15-20 min protected from light. Add 40 ml of RPMI media to absorb any unload dye. Incubate for additional 5 min at 37 C (in a water bath) protected from light. Spin down the cells at 400×g/5 min/RT.

In some embodiments, an inflammatory intestine on-chip prepared in Section 1 and Section 2, combined with methods in Section 4, is used for modeling inflammation. However, in part due to challenges with controlling shear forces and rates, as described herein, in addition to the discovery that a 50% Percoll liquid lowered shear in a manner allowing maximal attachment of white blood cells, as opposed to 15% and 75% Percoll liquid solutions. Therefore, a 50% Percoll solution Section (step) was added Section 3: Addition of the Percoll Solution to Immune Cells (PBMC's):

Prepare 50% Percoll solution in RPMI media by mixing stock Percoll solution and RPMI media 1:1 (vol/vol) e.g. 10 ml of Percoll with 10 ml of RPMI media; in some embodiment, degass solutions using a steri-flip. Add 50% Percoll/RPMI solution to the cells to achieve final cell concentration of 2×10^6 cells/ml.

Section 4: Recruitment Assay:

Add PBMC's as a cell suspension in 50% Percoll/RPMI into the Input Reservoir of the Bottom Channel, while in the Input Reservoir of the Top Channel add appropriate epithelial cell media (see Porotocol for Small Intestine-Chip). Perfuse the immune cell solution through the Bottom Channel at the Shear Stress of ~2 dyn/cm2 (flow rate~1200 ul/h) for 15 min. Aspirate media in both output Reservoirs. Add fresh RPMI media of Input Reservoirs of the Bottom Channel. Perfuse the Bottom Channel with RPMI media for additional 15 min at high flow rate of 1200 ul/h to remove cells that didn't adhere to the endothelial cell surface.

Section 5: Assessment of Immune Cell Rrecruitment:

Image the cells that attached to endothelial cells using Immunofluorescent or Confocal Microscope (endothelial cells can be co-stained using Wheat Germ Agglutinin (WGA), if assessment needs to be performed in the life cells or VE-cadherin or other staining specific for endothelial cells, if post-fixation assessment is preferred) Immune Cells can be co-stained for CD14 or CD3 markers in order to differentiate them into different subpopulations of monocytes and lymphocytes, respectively Cells on-chips can be lysed in order to assess endothelial or immune cells gene expression Effluents can be collected from the Top and Bottom Output Reservoirs in order to assess cytokines and chemokines released by the cells.

After assessment of immune cell recruitment chips can be terminated by the fixation with 4% PFA or can be maintained in culture under the normal flow conditions of 60 ul/h for their further assessment, including studies of immune cell translocation into the epithelial channel, contribution of immune cells to Intestine-Chip response to luminally applied stimuli etc.

FIGS. 17A-D shows exemplary florescent microscope images, focused on the endothelial plane, showing green labeled PBMC (peripheral mononuclear blood cells) (each green dot represents one cell) attachment to inflamed endothelium, under liquid flow where the liquid contained FIG. 17A 0% Percoll, FIG. 17B 25% Percoll, FIG. 17C 50% Percolland FIG. 17D 80% Percoll, demonstrating that increased media viscosity improves immune cells recruitment. Addition of Percoll increases media viscosity and improves immune cells-endothelium interaction at 50% Percoll where a clear cell attachment was seen (numerous green dots). Fifty percent (50%) Percoll also showed the highest number of immune cell recruitment to inflamed endothelium. Therefore, increased media viscosity is achieved by addition of Percoll, where Percoll consists of colloidal silica particles of 15-30 nm diameter coated with polyvinylpyrrolidone (PVP). Furthermore, an increase shear allows immune cells to interact with endothelial cells.

FIGS. 18A-C shows embodiments of an intestine on chip emulating immune cell recruitment on-Chip through providing physiological level of shear and fluid viscosity to emulate immune cell recruitment at epithelial-endothelial tissue interfaces. Embodiments of intestine on chip showing a florescent micrograph of stained cells FIG. 18A under non-physiological shear in vascular channel and non-physiological fluid viscosity. FIG. 18B under physiological shear in vascular channel and physiological fluid viscosity. PBMCs (green) and inflamed HIMEC (red). FIG. 18C shows flow directions (arrows) on a chip schematic. Scale bar=100 micrometers. Physiological levels of shear and fluid viscosity emulate immune cell recruitment at the epithelial-endothelial (tissue-tissue) interface.

FIGS. 19A-B shows that a change in the media viscosity does not affect the expression of adhesion molecules on endothelial cells (vascular compartment) on-chip. FIG. 19A chart showing relative mRNA expression between standard media (left, grey bars), viscous media (50% Percoll) (blue, middle bars) and inflammatory inducing media containing Cytomix cytokines (right, pink bars), after 24 hours of treatment. FIG. 19B showing micrographs of cells (left) corresponding to lower power micrographs of the channels (right). Stained ICAM-1 (pink) and nuclei (blue). Upper is a control intestine on-chip, middle is an inflamed intestine on-chip and lower is a chip treated with viscous media, 50% Percoll, intestine on-chip.

FIGS. 20A-B shows exemplary florescent microscope images and graphs demonstrating induction of adhesion molecule expression in intestinal endothelial cells on-chip after induction of inflammation using clinically relevant levels of cytokines. FIG. 20A ICAM-1 (pink) and nuclei (blue) stained channels (left) and under higher magnification (right) for control (upper) and inflamed (lower) channels. FIG. 20B shows a graphical comparison of relative mRNA expression for E-selectin, VCAM1, MadCAM1 and ICAM-1. Cells on-chip were treated for 24 hours with a Cytomix Formulation: TNF-alpha 10 U/ml (approximately 215 pg/ml), IL-1 beta approximately 50 U/ml (approximately 50 pg/ml), IL-6 20 U/ml (approximately200 pg/ml). U=units.

FIGS. 21A-C shows one embodiment of immune cell recruitment in a microfluidic chip contemplated for use with a fluid-modifying reagent, e.g. an inflamed intestine on-chip where PBMCs were suspended in a 50% Percoll fluid flowing through the chip. FIG. 21A shows one embodiment of a microfluidic chip where PBMCS or other white blood cell populations may be added in the lower channel (thick arrow) or added mid-channel on either side, see thin arrows). FIG. 21B shows exemplary results in a viewing area on-chip where the channel area shown is delineated by dotted lines in FIG. 21A). Far left B panel shows a control intestine on-chip with no PBMCs, hence no dots. Middle panel shows a non-inflamed intestine on-chip with PBMCs attached to the endothelium as scattered dots. Far right shows an inflamed intestine on-chip with PBMCs as numerous scattered dots attached to the endothelium (see inflammation induction methods in FIG. 20A). FIG. 21C shows a graph comparing PBMC recruitment to the endothelial layer between controls; non-inflamed and inflamed endothelium.

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A method, comprising:
a) providing i) a microfluidic device comprising a body comprising a microchannel therein, said microchannel comprising (1) a membrane disposed within at least a portion of the microchannel and configured to separate the microchannel into first and second microchannels, and (2) endothelial cells in a layer on said membrane in said first microchannel; and ii) a fluid, said fluid comprising a colloid density-modifying reagent and one or more immune cell types; and b) flowing said fluid into said first microchannel to produce a shear rate and an increased number of said immune cells that are adhered to said endothelial cells on said membrane in said microchannel in the presence of the colloid density-modifying reagent compared to in the absence of the colloid density-modifying reagent in said first microchannel.

2. The method of claim 1, wherein said flowing produces an interaction by said one or more immune cell types with said endothelial cells in said first microchannel without the use of gravity.

3. The method of claim 1, wherein the membrane is coated with at least one attachment molecule that supports adhesion of a plurality of living cells.

4. The method of claim 1, wherein the membrane is a porous membrane.

5. The method of claim 1, wherein the membrane is at least partially flexible.

6. The method of claim 1, wherein the endothelial cells are on the bottom of the membrane.

7. The method of claim 6, wherein epithelial cells are on the top of the membrane.

8. The method of claim 1, wherein said colloid is a silica-based colloid.

9. The method of claim 1, wherein the method further comprises, prior to step b), exposing said endothelial cells to an inflammatory cytokine.

10. The method of claim 1, wherein said endothelial cells are from a healthy human patient.

11. The method of claim 1, wherein said endothelial cells are from a human patient with symptoms of an inflammatory or autoimmune disorder.

* * * * *